(12) United States Patent
Yu et al.

(10) Patent No.: US 8,618,095 B2
(45) Date of Patent: Dec. 31, 2013

(54) 2, 4-PYRIMIDINEDIAMINE COMPOUNDS AND PRODRUGS THEREOF AND THEIR USES

(75) Inventors: Jiaxin Yu, Foster City, CA (US); Jeffrey Clough, Redwood City, CA (US); Rajinder Singh, Belmont, CA (US); Pingyu Ding, Foster City, CA (US); Somasekhar Bhamidipati, Foster City, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 75 days.

(21) Appl. No.: 13/086,081

(22) Filed: Apr. 13, 2011

(65) Prior Publication Data

US 2011/0251177 A1 Oct. 13, 2011

Related U.S. Application Data

(60) Provisional application No. 61/323,699, filed on Apr. 13, 2010.

(51) Int. Cl.
*C07D 498/04* (2006.01)
*A61K 31/5383* (2006.01)

(52) U.S. Cl.
USPC .......................... 514/230.5; 544/73

(58) Field of Classification Search
USPC .......................... 544/73; 514/230.5
See application file for complete search history.

(56) References Cited

U.S. PATENT DOCUMENTS

| | | | |
|---|---|---|---|
| 7,122,542 B2 | 10/2006 | Singh et al. | |
| 7,449,458 B2 | 11/2008 | Bhamidipati et al. | |
| 7,485,724 B2 | 2/2009 | Singh et al. | |
| 7,498,435 B2 | 3/2009 | Singh et al. | |
| 7,517,886 B2 | 4/2009 | Singh et al. | |
| 7,538,108 B2 | 5/2009 | Singh et al. | |
| 7,560,466 B2 * | 7/2009 | Singh et al. | 514/272 |
| 7,563,892 B1 | 7/2009 | Singh et al. | |
| 7,582,648 B2 | 9/2009 | Singh et al. | |
| 7,713,987 B2 | 5/2010 | Bhamidipati et al. | |
| 7,812,029 B1 | 10/2010 | Singh et al. | |
| 7,825,116 B2 | 11/2010 | Singh et al. | |
| 7,884,111 B2 | 2/2011 | Argade et al. | |
| 7,989,448 B2 * | 8/2011 | Singh et al. | 514/230.5 |
| 8,158,621 B2 | 4/2012 | Singh et al. | |
| 8,163,902 B2 | 4/2012 | Bhamidipati et al. | |
| 8,178,671 B2 | 5/2012 | Singh et al. | |
| 8,188,276 B2 | 5/2012 | Singh et al. | |
| 8,211,888 B2 | 7/2012 | Singh et al. | |
| 8,211,889 B2 | 7/2012 | Singh et al. | |
| 8,227,455 B2 | 7/2012 | Masuda et al. | |
| 2009/0318687 A1 | 12/2009 | Singh et al. | |
| 2011/0124599 A1 | 5/2011 | Singh et al. | |
| 2011/0190271 A1 | 8/2011 | Argade et al. | |
| 2012/0208785 A1 | 8/2012 | Bhamidipati et al. | |
| 2012/0230984 A1 | 9/2012 | Singh et al. | |
| 2012/0232036 A1 | 9/2012 | Bhamidipati et al. | |

FOREIGN PATENT DOCUMENTS

| | | |
|---|---|---|
| WO | 03063794 | 8/2003 |
| WO | 2004014382 | 2/2004 |
| WO | 2005012294 A1 | 2/2005 |
| WO | 2005016893 | 2/2005 |
| WO | 2006068770 A1 | 6/2006 |
| WO | 2008118823 A2 | 10/2008 |
| WO | 2009003136 A1 | 12/2008 |
| WO | 2010039518 A2 | 4/2010 |
| WO | 2010078369 A2 | 7/2010 |
| WO | 2011063241 A1 | 5/2011 |

* cited by examiner

*Primary Examiner* — Kahsay Habte
(74) *Attorney, Agent, or Firm* — Travis Young; McDonnell Boehnen Hulbert & Berghoff LLP

(57) ABSTRACT

The present disclosure provides biologically active 2,4-pyrimidinediamine compounds of formulae (I) and (II):

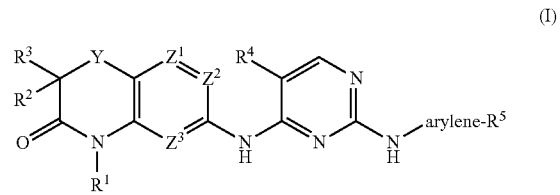

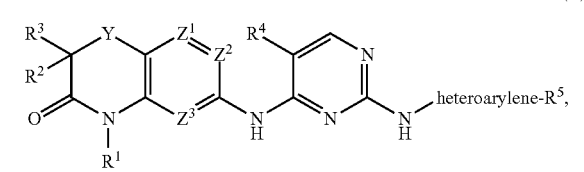

and salts thereof, compositions comprising these compounds, and methods of using these compounds in a variety of applications.

24 Claims, No Drawings

2,4-PYRIMIDINEDIAMINE COMPOUNDS AND PRODRUGS THEREOF AND THEIR USES

CROSS-REFERENCE TO RELATED APPLICATIONS

This application claims the benefit of U.S. Provisional Patent Application No. 61/323,699, filed on Apr. 13, 2010, which is hereby incorporated herein by reference in its entirety.

BACKGROUND

1. Field of the Disclosure

The present disclosure relates to biologically active 2,4-pyrimidinediamine compounds and prodrugs thereof, pharmaceutical compositions comprising these compounds, intermediates and synthetic methods of making these compounds and methods of using these compounds and compositions in a variety of contexts, such as in the treatment or prevention of various diseases.

2. Description of the Related Art

Crosslinking of Fc receptors, such as the high affinity receptor for IgE (FcϵRI) and/or the high affinity receptor for IgG (FcγRI) activates a signaling cascade in mast, basophil and other immune cells that results in the release of chemical mediators responsible for numerous adverse events. For example, such crosslinking leads to the release of preformed mediators of Type I (immediate) anaphylactic hypersensitivity reactions, such as histamine, from storage sites in granules via degranulation. It also leads to the synthesis and release of other mediators, including leukotrienes, prostaglandins and platelet-activating factors (PAFs), that play important roles in inflammatory reactions. Additional mediators that are synthesized and released upon crosslinking Fc receptors include cytokines and nitric oxide.

The signaling cascade(s) activated by crosslinking Fc receptors such as FcϵRI and/or FcγRI includes an array of cellular proteins. Among the most important intracellular signal propagators are the tyrosine kinases. One important tyrosine kinase involved in the signal transduction pathways associated with crosslinking the FcϵRI and/or FcγRI receptors, as well as other signal transduction cascades, is Syk kinase (see Valent et al., 2002, Intl. J. Hematol. 75(4):257-362 for review).

The mediators released as a result of FcϵRI and FcγRI receptor cross-linking are responsible for, or play important roles in, the manifestation of numerous adverse events. Recently, various classes of 2,4-pyrimidinediamine compounds have been discovered that inhibit the FcϵRI and/or FcγRI signaling cascades, and that have myriad therapeutic uses. See, e.g., U.S. patent application Ser. No. 10/355,543 filed Jan. 31, 2003 (US 2004/0029902A1), international patent application Serial No. PCT/US03/03022 filed Jan. 31, 2003 (WO 03/063794), U.S. patent application Ser. No. 10/631,029 filed Jul. 29, 2003 (US 2007/0060603), international patent application no. PCT/US03/24087 (WO 2004/014382), U.S. patent application Ser. No. 10/903,263 filed Jul. 30, 2004 (US2005/0234049), and international patent application no. PCT/US2004/24716 (WO 2005/016893), each of which is hereby incorporated herein by reference in its entirety. While many of these compounds exhibit good bioavailability properties, in some instances it may be desirable to tailor their solubility or other properties such that their bioavailability via specified routes of administration is optimized.

International patent application no. PCT/US03/03022 filed Jan. 31, 2003 (WO 03/063794), international patent application no. PCT/US07/85313 filed Nov. 20, 2007 (WO 2008/064274), and international patent application no. PCT/US06/01945 filed Jan. 19, 2006 (WO 2006/078846), each of which is hereby incorporated herein by reference in its entirety, disclose a class of 2,4-pyrimidinediamine compounds and prodrugs thereof as being useful in a variety of in vitro and in vivo contexts, including in the treatment and/or prevention of diseases mediated, at least in part, by the activation of Fc receptor signaling cascades. While these compounds are useful in a variety of in vitro and in vivo contexts, there remains a need for compounds with improved effects and increased duration of actions.

SUMMARY OF THE DISCLOSURE

In a broad aspect, the disclosure provides 2,4-pyrimidinediamine compounds and prodrugs thereof that have myriad biological activities, and hence therapeutic uses, compositions comprising the compounds and prodrugs, methods and intermediates useful for synthesizing the compounds and prodrugs and methods of using the compounds and prodrugs in a variety of in vitro and in vivo contexts, including in the treatment and/or prevention of diseases mediated, at least in part, by the activation of Fc receptor signaling cascades.

Thus, one aspect of the disclosure provides compounds of formula (I):

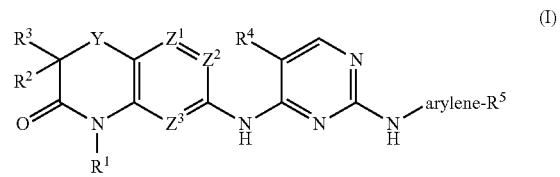

or of formula (II):

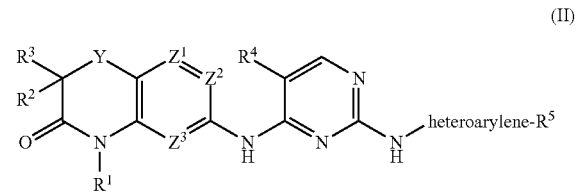

and pharmaceutically acceptable salts of each.

Another aspect of the disclosure provides pharmaceutical compositions comprising the compound and salts of the disclosure and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

Another aspect of the disclosure provides a method of inhibiting cell degranulation in a subject, comprising administering to the subject a pharmaceutically effective amount of a compound, salt or composition of the disclosure effective to inhibit degranulation.

Yet another aspect of the disclosure provides a method for treating or preventing a disease selected from an allergic disease, low grade scarring, a disease associated with tissue destruction, a disease associated with tissue inflammation, inflammation and scarring, comprising administering to the subject a pharmaceutically effective amount of a compound, salt or composition of the disclosure.

In one aspect, the disclosure provides a method of treating rheumatoid arthritis in a subject, comprising administering to a subject suffering from rheumatoid arthritis a pharmaceutically effective amount of a compound, salt or composition of the disclosure.

Another aspect of the disclosure provides a method of inhibiting an activity of a Syk kinase in a subject, comprising administering to the subject a pharmaceutically effective amount of a compound, salt or composition of the disclosure effective to inhibit the Syk kinase activity.

In another aspect, the disclosure provides a method of inhibiting an Fc receptor signal transduction cascade in a subject, comprising administering to the subject a pharmaceutically effective amount of a compound, salt or composition of the disclosure effective to inhibit the Fc receptor signal transduction cascade. Fc receptor is selected from FcαRI, FcγRI, FcγRIII and FcεRI.

Another aspect of the disclosure provides a method of treating or preventing an autoimmune disease in a subject, and/or one or more symptoms associated therewith, comprising administering to the subject a pharmaceutically effective amount of a compound, salt or composition of the disclosure effective to treat or prevent the autoimmune disease.

Another aspect of the disclosure provides a method of treating a cell proliferative disorder in a subject, comprising administering to a subject suffering from a cell proliferative disorder a pharmaceutically effective amount of a compound, salt or composition according to the disclosure.

Another aspect of the disclosure provides a method of regulating or inhibiting Syk kinase in a cell comprising contacting a Syk kinase or a cell comprising a Syk kinase with a compound or salt of the disclosure.

Another aspect of the disclosure provides a method of regulating or inhibiting the Fc receptor signaling cascade comprising contacting a cell expressing an Fc receptor with a compound or salt of the disclosure.

Another aspect of the disclosure provides a method of regulating or inhibiting degranulation of a cell comprising contacting a cell that degranulates with a compound or salt of the disclosure.

Another aspect of the disclosure provides a method of regulating or inhibiting the signal transduction cascade comprising contacting a Syk-dependent receptor or a cell expressing a Syk-dependent receptor with a compound or salt of the disclosure.

DETAILED DESCRIPTION

One aspect of the disclosure provides compounds of formula (I):

(I)

$R^3$—Y—$Z^1$=$Z^2$—$R^4$— ... —arylene-$R^5$ or of formula (II):

(II)

$R^3$—Y—$Z^1$=$Z^2$—$R^4$— ... —heteroarylene-$R^5$ or a pharmaceutically acceptable salt thereof, wherein:

Y is oxygen or sulfur;

$Z^1$, $Z^2$, and $Z^3$ are independently selected from CH and N;

$R^1$ is hydrogen, $C_1$-$C_6$ alkyl, or $R^8$;

$R^2$ and $R^3$ are independently selected from hydrogen, halogen, $C_1$-$C_6$ alkyl, and halo($C_1$-$C_6$ alkyl), or $R^2$ and $R^3$ together with the carbon to which they are attached form $C_3$-$C_6$ cycloalkyl;

$R^4$ is hydrogen, halogen, cyano, nitro, $C_1$-$C_6$ alkyl, or halo($C_1$-$C_6$ alkyl);

$R^5$ is $C_1$-$C_6$ alkyl, —N($R^7$)$_2$, aryl optionally substituted with 1, 2, 3, or 4 $R^6$ groups, heteroaryl optionally substituted with 1, 2, 3, or 4 $R^6$ groups, cycloalkyl optionally substituted with 1, 2, 3, 4, 5, 6, 7, or 8 $R^6$ groups or heterocycloalkyl optionally substituted with 1, 2, 3, 4, 5, 6, 7, or 8 $R^6$ groups, in which each $R^6$ is independently selected from deuterium, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), (($C_1$-$C_6$ alkyl)amino)($C_1$-$C_6$ alkyl), (di($C_1$-$C_6$ alkyl)amino)($C_1$-$C_6$ alkyl), —C(O)OH, —C(O)NH$_2$, $C_3$-$C_8$ cycloalkyl, aryl, heteroaryl, and heterocycloalkyl, or two $R^6$ groups form a spiro-fused $C_3$-$C_6$ cycloalkyl, a spiro-fused heterocycloalkyl, oxo, =CH$_2$, or =CH($C_1$-$C_6$ alkyl); and each $R_7$ is independently selected from hydrogen, $C_1$-$C_6$ alkyl, $C_2$-$C_6$ alkenyl, $C_2$-$C_6$ alkynyl, halo($C_1$-$C_6$ alkyl), hydroxy($C_1$-$C_6$ alkyl), ($C_1$-$C_6$ alkoxy)$C_1$-$C_6$ alkyl, aryl, heteroaryl, heterocycloalkyl, (aryl)$C_1$-$C_6$ alkyl, (heteroaryl)$C_1$-$C_6$ alkyl, and (heterocycloalkyl)$C_1$-$C_6$ alkyl; and $R^8$ is selected from —(CR$^{11}$R$^{11}$)$_k$—O—P(O)(OR$^{12}$)$_2$, —(CR$^{11}$R$^{11}$)$_n$—O—P(=O)(O—$R^{13}$)(O—CR$^{13}$)$_m$, and —(CR$^{11}$R$^{11}$)$_n$—O—P(O—$R^{13}$)(O—CR$^{13}$)$_m$, in which each $R^{11}$ is independently selected from hydrogen, $C_1$-$C_6$ alkyl, aryl, and (aryl)$C_1$-$C_6$ alkyl, in which each alkyl or aryl is optionally substituted with halogen, hydroxy, $C_1$-$C_6$ alkoxy, aryloxy, or ($C_1$-$C_6$ alkyl)aryloxy, or two $R_{11}$ groups together with the carbon to which they are attached form $C_3$-$C_6$ cycloalkyl, each $R^{12}$ is independently selected from hydrogen, $C_1$-$C_6$ alkyl, aryl, (aryl)$C_1$-$C_6$ alkyl, —$(CR^{11}R^{11})_k$—$OR^{16}$, —$(CR^{11}R^{11})_k$—O—C(O)$R^{16}$, —$(CR^{11}R^{11})_k$—O—C(O)$OR^{16}$, —$(CR^{11}R^{11})_k$—S—C(O)$R^{16}$, —$(CR^{11}R^{11})_k$—S—C(O)$OR^{16}$, —$(CR^{11}R^{11})_k$—NH—C(O)$OR^{16}$, —$(CR^{11}R^{11})_k$—NH—C(O)$OR^{16}$ and —Si$(R^{11})_3$, in which each alkyl or aryl is optionally substituted with halogen, hydroxy, $C_1$-$C_6$ alkoxy, aryloxy, or ($C_1$-$C_6$ alkyl)aryloxy, and each $R^{16}$ is independently selected from hydrogen, $C_1$-$C_6$ alkyl, aryl, and (aryl)$C_1$-$C_6$ alkyl, each $R^{13}$ is independently selected from hydrogen, $C_1$-$C_6$ alkyl, aryl, (aryl)$C_1$-$C_6$ alkyl, heteroaryl, and heterocycloalkyl, each k is 1, 2 or 3, each m is 0, 1, or 2, and each n is 1, 2 or 3;

wherein the arylene is further substituted with 0, 1, 2, 3, or 4 $R^9$, where each $R^9$ is independently selected from halogen, cyano, $C_1$-$C_6$ alkyl, halo($C_1$-$C_6$ alkyl), $C_1$-$C_6$ alkoxy, and halo($C_1$-$C_6$ alkoxy), or $R^9$ and $R^5$ together with the carbons to which they are attached form $C_5$-$C_{10}$ heterocycloalkyl; and the heteroarylene is further substituted with 0, 1, 2, 3, or 4 $R^{10}$, where each $R^{10}$ is independently selected from halogen, cyano, $C_1$-$C_6$ alkyl, halo($C_1$-$C_6$ alkyl), $C_1$-$C_6$ alkoxy, and halo($C_1$-$C_6$ alkoxy), or $R^{10}$ and $R^5$ together with the carbons to which they are attached form $C_5$-$C_{10}$ heterocycloalkyl, provided the compound is not N4-(3,4-dihydro-3-oxo-2H-pyrido[3,2-b][1,4]oxazin-6-yl)-5-fluoro-N2-(4-morpholinophenyl)-2,4-pyrimidinediamine, N4-(2,2-dimethyl-3,4-dihydro-3-oxo-2H-pyrido[3,2-b][1,4]oxazin-6-yl)-5-fluoro-N2-(4-morpholinophenyl)-2,4-pyrimidinediamine, N4-(2,2-dimethyl-3,4-dihydro-3-oxo-2H-pyrido[3,2-b][1,4]oxazin-6-yl)-5-fluoro-N2-(4-(4-methylpiperazin-1-yl)phenyl)-2,4-pyrimidinediamine, or N4-(3,4-dihydro-3-oxo-2H-pyrido[3,2-b][1,4]oxazin-6-yl)-5-fluoro-N2-(4-ethoxycarbonylpiperazin-1-yl(phenyl))-2,4-pyrimidinediamine.

In one embodiment, the disclosure provides compounds of formula (I).

In another embodiment, the disclosure provides compounds of formula (I), wherein the arylene is phenylene.

In another embodiment, the disclosure provides compounds of formula (I), wherein the arylene is phenylene, and the $R^5$ is substituted at the para position of the phenylene with respect to the pyrimidin-2-ylamine. These compounds can be represented by formula (III):

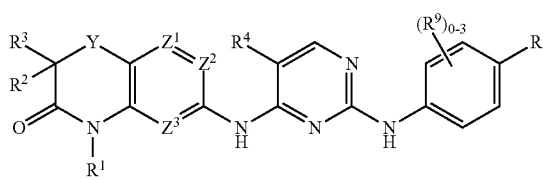

(III)

In another aspect, the present disclosure provides a compound of formula (II).

In one embodiment, the disclosure provides compounds of formula (II), wherein the heteroarylene is a monocyclic heteroarylene.

In certain embodiments, the disclosure provides compounds of formula (II), wherein the heteroarylene is pyridylene, pyrazylene, pyrimidylene, or pyridazylene.

In another embodiment, the disclosure provides compounds of formula (II), wherein the heteroarylene is pyridylene.

In yet another embodiment, the disclosure provides compounds of formula (II), wherein the heteroarylene is pyridylene, and $R^5$ is substituted at the para position of the heteroarylene with respect to the pyrimidin-2-ylamine. These compounds can be represented by formula (IV):

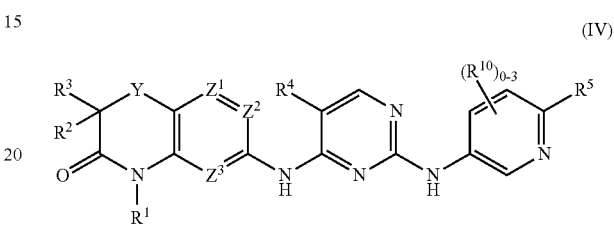

(IV)

In one embodiment, the disclosure provides compounds as described above with reference to any of formulae (I)-(IV), wherein Y is oxygen.

In another embodiment, the disclosure provides compounds as described above with reference to any of formulae (I)-(IV), wherein Y is sulfur.

In one embodiment, the disclosure provides compounds as described above with reference to any of formulae (I)-(IV), wherein $Z^1$ is carbon, $Z^2$ is carbon, and $Z^3$ is nitrogen.

In another embodiment, the disclosure provides compounds as described above with reference to any of formulae (I)-(IV), wherein $Z^1$ is nitrogen, $Z^2$ is carbon, and $Z^3$ is carbon.

In yet another embodiment, the disclosure provides compounds as described above with reference to any of formulae (I)-(IV), wherein $Z^1$ is carbon, $Z^2$ is carbon, and $Z^3$ is carbon.

In certain embodiments, the disclosure provides compounds as described above with reference to any of formulae (I)-(IV), wherein Y is oxygen, $Z^1$ is carbon, $Z^2$ is carbon, and $Z^3$ is nitrogen. These compounds can be represented by formulae (V) and (VI):

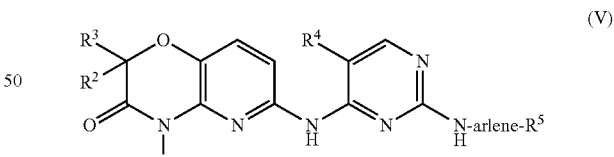

(V)

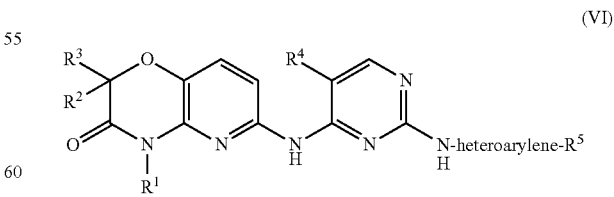

(VI)

In certain embodiments, the disclosure provides compounds as described above with reference to any of formulae (I)-(IV), wherein Y is oxygen, $Z^1$ is nitrogen, $Z^2$ is carbon, and $Z^3$ is carbon. These compounds can be represented by formulae (VII) and (VIII):

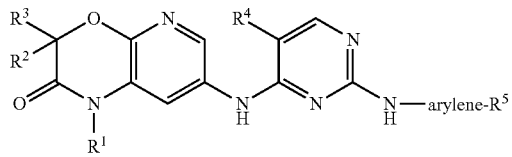

(VII)

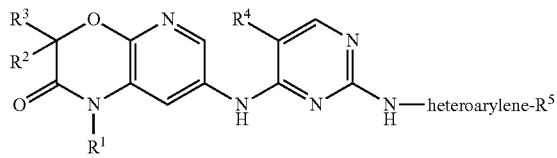

(VIII)

In certain embodiments, the disclosure provides compounds as described above with reference to any of formulae (I)-(IV), wherein Y is oxygen, $Z^1$ is carbon, $Z^2$ is carbon, and $Z^3$ is carbon. These compounds can be represented by formulae (IX) and (X):

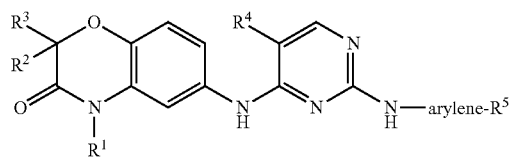

(IX)

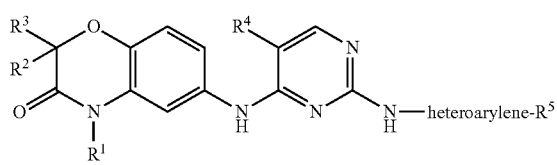

(X)

In one embodiment, the disclosure provides compounds as described above with reference to any of formulae (I)-(X), wherein $R^2$ and $R^3$ are independently selected from hydrogen and $C_1$-$C_6$ alkyl, or $R^2$ and $R^3$ together with the carbon to which they are attached form $C_3$-$C_6$ cycloalkyl.

In certain embodiments, the disclosure provides compounds as described above with reference to any of formulae (I)-(X), wherein $R^2$ and $R^3$ are independently selected from hydrogen, and $C_1$-$C_6$ alkyl. In certain embodiments, $R^2$ and $R^3$ are independently selected from hydrogen and methyl. For example, in one embodiment, both $R^2$ and $R^3$ are hydrogen. In another embodiment, $R^2$ and $R^3$ are both methyl. In another embodiment, $R^2$ is hydrogen and $R^3$ is methyl.

In yet another embodiment, the disclosure provides compounds as described above with reference to any of formulae (I)-(X), wherein $R^2$ and $R^3$ together with the carbon to which they are attached form a spiro-fused cyclobutane.

In certain embodiments, the disclosure provides compounds as described above with reference to any of formulae (I)-(X), wherein the

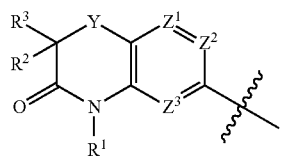

moiety is:

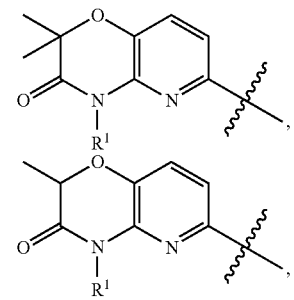

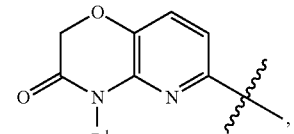

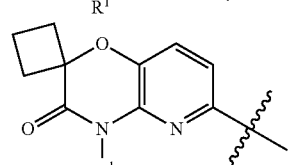

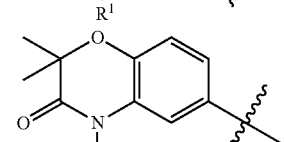

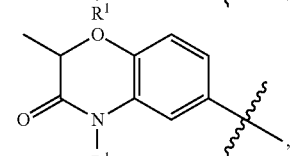

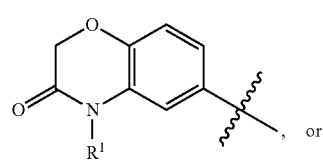, or

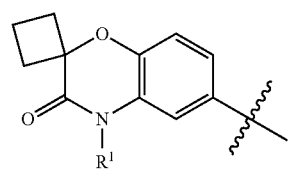.

For example, in some embodiments, the disclosure provides compounds as described above with reference to any of formulae (I)-(X), wherein the

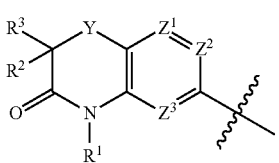

moiety is:

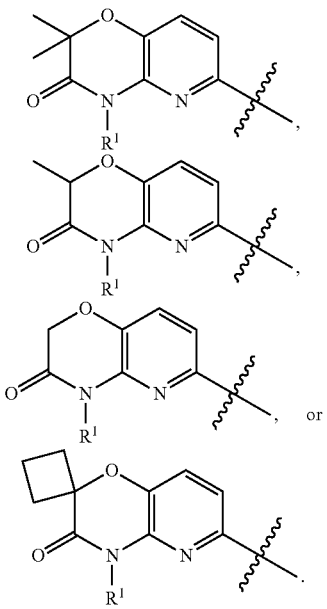

In certain embodiments, the disclosure provides compounds as described above with reference to any of formulae (I)-(X), wherein $R^1$ is hydrogen or $R^8$.

For example, in one embodiment, the disclosure provides compounds as described above with reference to any of formulae (I)-(IV), wherein $R_1$ is hydrogen.

In certain embodiments, the disclosure provides compounds as described above with reference to any of formulae (I)-(X), wherein $R^1$ is $R^8$. In certain embodiments, $R^1$ is selected from $(CR^{11}R^{11})_k$—O—P(O)(OR^{12})_2$,

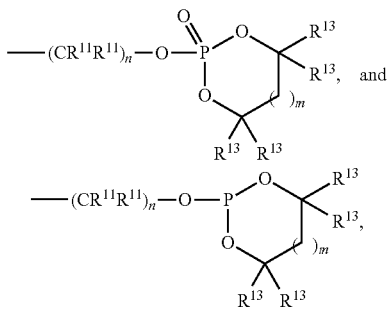

in which
each $R^{11}$ is independently selected from hydrogen and $C_1$-$C_6$ alkyl;
each $R^{12}$ is independently selected from hydrogen and $C_1$-$C_6$ alkyl;
each $R^{13}$ is independently selected from hydrogen and $C_1$-$C_6$ alkyl;

k is 1, 2 or 3;
each m is 0, 1, or 2; and
each n is 1, 2 or 3.

In certain embodiments, the disclosure provides compounds as described above with respect to any of formulae (I)-(X), wherein $R^1$ is selected from $(CR^{11}R^{11})_k$—O—P(O)(OR^{12})_2$, and

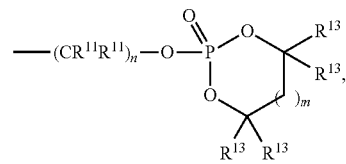

in which
each $R^{11}$ is independently selected from hydrogen and $C_1$-$C_6$ alkyl;
each $R^{12}$ is independently selected from hydrogen and $C_1$-$C_6$ alkyl;
each $R^{13}$ is independently selected from hydrogen and $C_1$-$C_6$ alkyl;
k is 1, 2 or 3;
each m is 0, 1, or 2; and
each n is 1, 2 or 3.

In another embodiment, the disclosure provides compounds as described above with respect to any of formulae (I)-(X), wherein $R^1$ is —CH$_2$—O—P(O)(OH)(OH), —CH$_2$CH$_2$—O—P(O)(OH)(OH), —CH$_2$—O—P(O)(OtBu)$_2$, or —CH$_2$CH$_2$—O—P(O)(OtBu)$_2$. In one embodiment, $R^1$ is —CH$_2$—O—P(O)(OH)(OH).

In another embodiment, $R^1$ is a cyclic phosphate ester of the formula

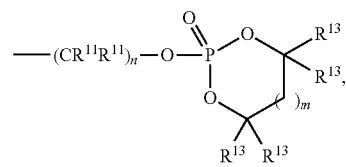

where $R^{11}$, $R^{13}$, m and n are as defined above. Specific examples of such cyclic phosphate esters include, but are not limited to, groups selected from:

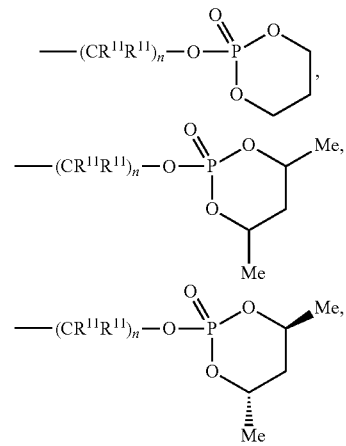

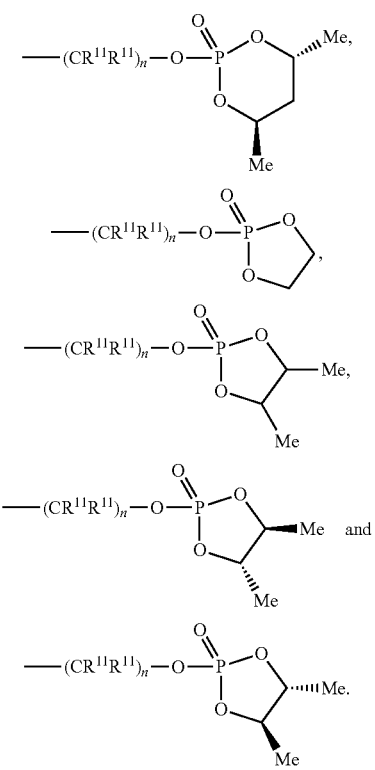
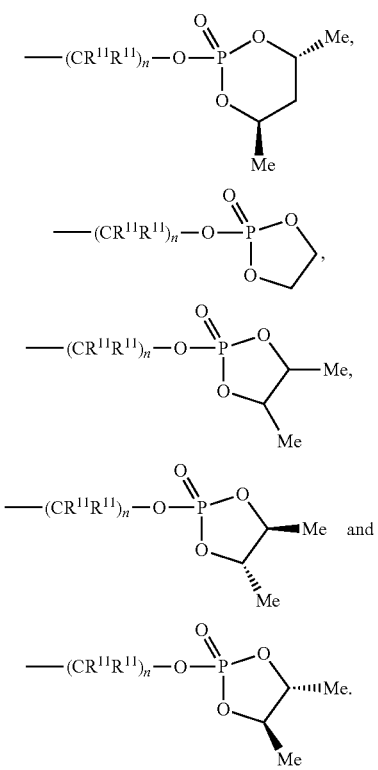
In yet another embodiment, $R^1$ is a cyclic phosphate ester of the formula
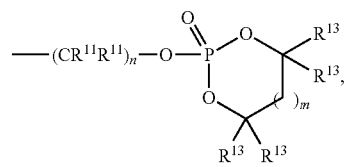
where $R^{11}$, $R^{13}$, m and n are as defined above. Specific examples of such cyclic phosphate esters include, but are not limited to, groups selected from:
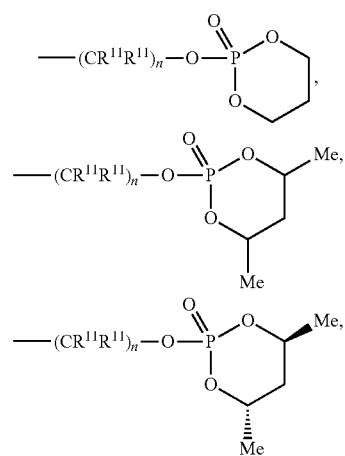
In one embodiment, the disclosure provides compounds as described above with respect to any of formulae (I)-(X), wherein the
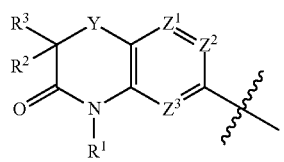
moiety is:
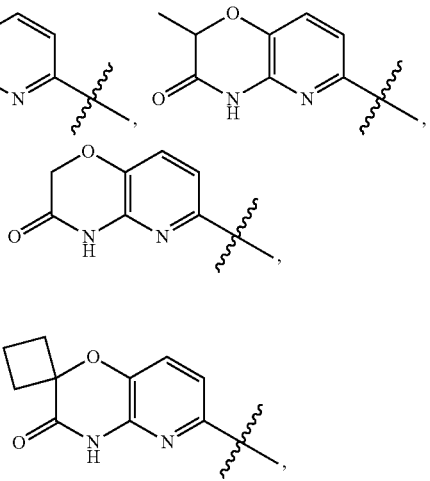

-continued

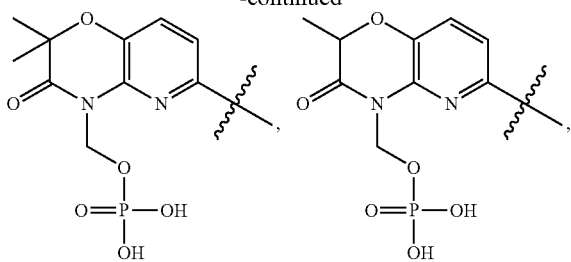
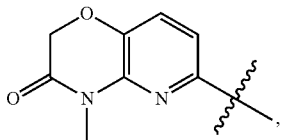
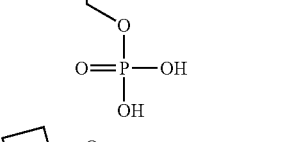
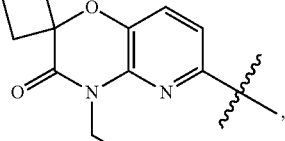
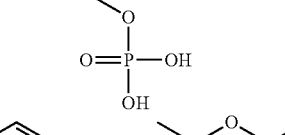
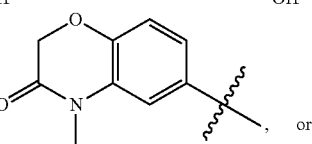
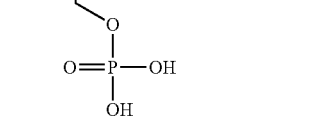, or -continued

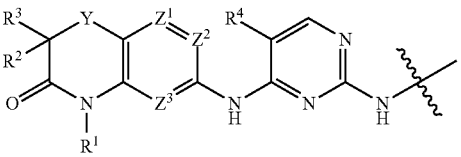

In certain embodiments, the disclosure provides compounds as described above with respect to any of formulae (I)-(X), wherein $R^4$ is hydrogen, halogen, $C_1$-$C_6$ alkyl, or halo($C_1$-$C_6$ alkyl).

In another embodiment, the disclosure provides compounds as described above with respect to any of formulae (I)-(X), wherein $R^4$ is halogen. In yet another embodiment, $R^4$ is —F.

In one embodiment, the disclosure provides compounds of formulae (I)-(IV), wherein the

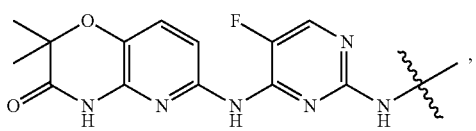

moiety is:

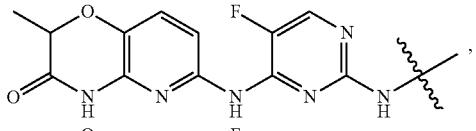
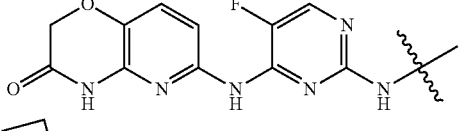
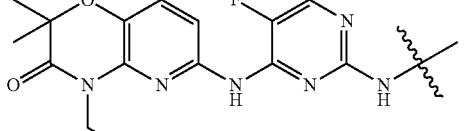
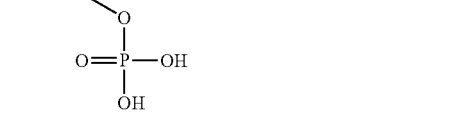

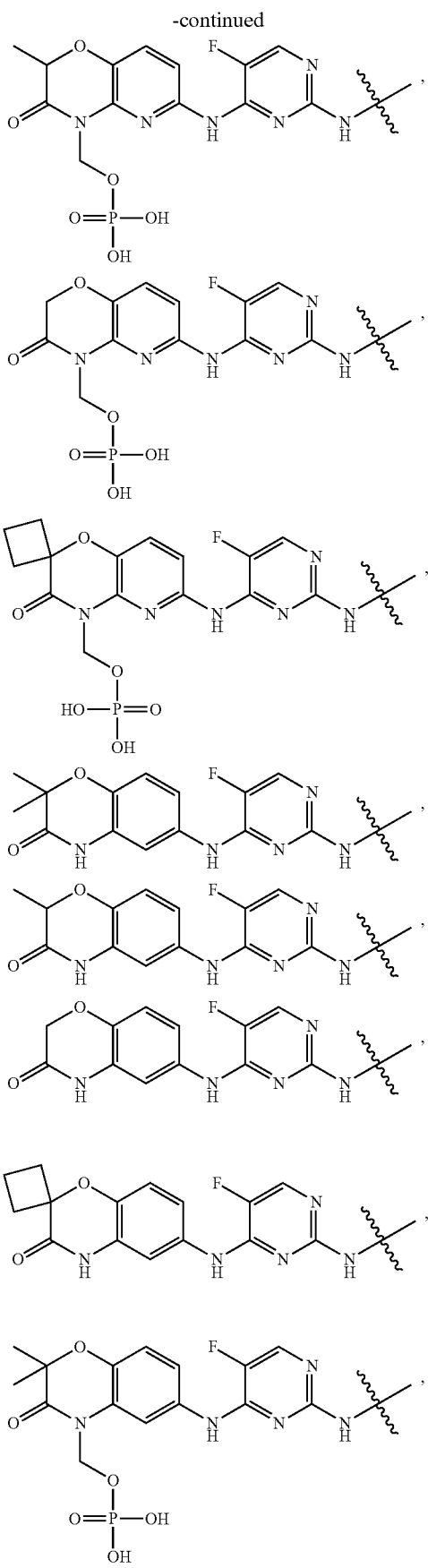
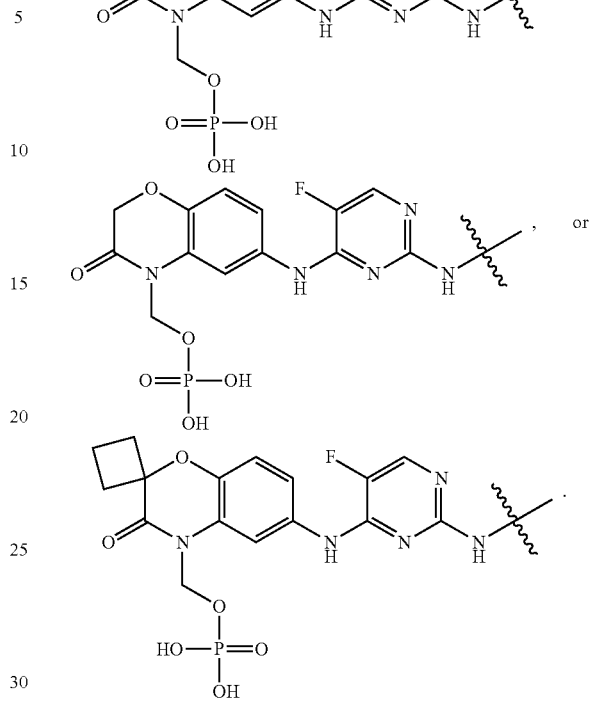

In one embodiment, the disclosure provides compounds as described above with respect to any of formulae (I)-(X), wherein the arylene or heteroarylene is unsubstituted.

In one embodiment, the disclosure provides compounds as described above with respect to any of formulae (I), (III), (V), (VII) and (IX), wherein each $R^9$ is independently selected from halogen, cyano, methyl, methoxy, isopropoxy, trifluoromethyl, and trifluoromethoxy, or as described above with respect to any of formulae (II), (IV), (VI), (VIII) and (X), wherein each $R^{10}$ is independently selected from halogen, cyano, methyl, methoxy, isopropoxy, trifluoromethyl, and trifluoromethoxy.

In one embodiment, the disclosure provides compounds as described above with respect to any of formulae (I), (III), (V), (VII) and (IX), wherein the arylene is substituted with 0, 1 or 2 $R^9$, or as described above with respect to any of formulae (II), (IV), (VI), (VIII) and (X), wherein the heteroarylene is substituted with 0, 1 or 2 $R^{10}$. For example, the arylene can be substituted with 0 or 1 $R^9$, or the heteroarylene can be substituted with 0 or 1 $R^{10}$.

In one embodiment, the disclosure provides compounds as described above with respect to any of formulae (I), (III), (V), (VII) and (IX), wherein the arylene is further substituted with one $R^9$, where each $R^9$ is halogen, methyl, methoxy, isopropoxy, trifluoromethyl, or trifluoromethoxy, or as described above with respect to any of formulae (II), (IV), (VI), (VIII) and (X), wherein the heteroarylene is substituted with one $R^{10}$, where each $R^{10}$ is halogen, methyl, methoxy, isopropoxy, trifluoromethyl, or trifluoromethoxy.

In yet another embodiment, the disclosure provides compounds as described above with respect to any of formulae (I)-(X), wherein $R^5$ is —N($R^7$)$_2$, aryl optionally substituted with 1, 2, 3, or 4 $R^6$ groups, heteroaryl optionally substituted with 1, 2, 3, or 4 $R^6$ groups, or heterocycloalkyl optionally substituted with 1, 2, 3, 4, 5, 6, 7, or 8 $R^6$ groups.

In one embodiment, the disclosure provides compounds as described above with respect to any of formulae (I)-(X), wherein each $R^6$ is independently selected from halogen, cyano, hydroxy, $C_1$-$C_6$ alkyl, halo($C_1$-$C_6$ alkyl), $C_1$-$C_6$ alkoxy, hydroxy($C_1$-$C_6$ alkyl), ($C_1$-$C_6$ alkoxy)$C_1$-$C_6$ alkyl, amino, ($C_1$-$C_6$ alkyl)amino, di($C_1$-$C_6$ alkyl)amino, —C(O)NH$_2$, and heterocycloalkyl, or two $R_6$ groups form a spiro-fused heterocycloalkyl, oxo, =CH$_2$, or =CH($C_1$-$C_6$ alkyl).

In another embodiment, the disclosure provides compounds as described above with respect to any of formulae (I)-(X), wherein each $R^6$ is independently selected from halogen, cyano, hydroxy, $C_1$-$C_6$ alkyl, halo($C_1$-$C_6$ alkyl), $C_1$-$C_6$ alkoxy, di($C_1$-$C_6$ alkyl)amino, hydroxy($C_1$-$C_6$ alkyl), ($C_1$-$C_6$ alkoxy)$C_1$-$C_6$ alkyl, amino, ($C_1$-$C_6$ alkyl)amino, di($C_1$-$C_6$ alkyl)amino, and —C(O)NH$_2$.

In yet another embodiment, the disclosure provides compounds as described above with respect to any of formulae (I)-(X), wherein each $R^6$ is independently selected from hydroxy, $C_1$-$C_6$ alkyl, halo($C_1$-$C_6$ alkyl), $C_1$-$C_6$ alkoxy, hydroxy($C_1$-$C_6$ alkyl), ($C_1$-$C_6$ alkoxy)$C_1$-$C_6$ alkyl, amino, ($C_1$-$C_6$ alkyl)amino, and di($C_1$-$C_6$ alkyl)amino.

In another embodiment, the disclosure provides compounds as described above with respect to any of formulae (I)-(X), wherein each $R^6$ is $C_1$-$C_6$ alkyl, for example, methyl. $R^5$ can, for example, be substituted with a single methyl group, geminally disubstituted with two methyl groups, or substituted with two methyl groups at two different heterocycloalkyl ring positions.

In one embodiment, the disclosure provides compounds as described above with respect to any of formulae (I)-(X), wherein $R^5$ is heterocycloalkyl optionally substituted with 1, 2, 3, 4, 5, 6, 7 or 8 $R^6$.

In another embodiment, the disclosure provides compounds as described above with respect to any of formulae (I)-(X), wherein $R^5$ is heterocycloalkyl optionally substituted with 1, 2, 3, or 4 $R^6$.

In yet another embodiment, the disclosure provides compounds as described above with respect to any of formulae (I)-(X), wherein $R^5$ is heterocycloalkyl optionally substituted with 1 or 2 $R^6$.

In yet another embodiment, the disclosure provides compounds as described above with respect to any of formulae (I)-(X), wherein $R^5$ is heterocycloalkyl optionally substituted with one $R^6$.

In another embodiment, the disclosure provides compounds as described above with respect to any of formulae (I)-(X), wherein $R^5$ is unsubstituted heterocycloalkyl.

In one embodiment, the disclosure provides compounds as described above with respect to any of formulae (I)-(X), wherein $R^5$ is cycloalkyl optionally substituted with 1, 2, 3, 4, 5, 6, 7 or 8 $R^6$.

In another embodiment, the disclosure provides compounds as described above with respect to any of formulae (I)-(X), wherein $R^5$ is cycloalkyl optionally substituted with 1, 2, 3, or 4 $R^6$.

In yet another embodiment, the disclosure provides compounds as described above with respect to any of formulae (I)-(X), wherein $R^5$ is cycloalkyl optionally substituted with 1 or 2 $R^6$.

In yet another embodiment, the disclosure provides compounds as described above with respect to any of formulae (I)-(X), wherein $R^5$ is cycloalkyl optionally substituted with one $R^6$.

In another embodiment, the disclosure provides compounds as described above with respect to any of formulae (I)-(X), wherein $R^5$ is unsubstituted cycloalkyl.

In certain embodiments, the disclosure provides compounds as described above with respect to any of formulae (I)-(X), wherein $R^5$ is morpholinyl, thiomorpholinyl, thiomorpholinyl-S,S-dioxide, piperidinyl, piperazinyl, pyrrolidinyl, oxazolidinyl, azetidinyl, tetrahydropyranyl, oxazepanyl, 2-oxa-5-azabicyclo[2.2.1]heptanyl, or 1,4-diazabicyclo[3.2.2]nonanyl. In one embodiment, heterocycloalkyl is morpholinyl, piperidinyl, piperazinyl, or pyrrolidinyl.

In another embodiment, the disclosure provides compounds as described above with respect to any of formulae (I)-(X), wherein $R^5$ is morpholinyl.

In yet another embodiment, the disclosure provides compounds as described above with respect to any of formulae (I)-(X), wherein $R^5$ is piperidinyl.

In certain embodiments, the disclosure provides compounds as described above with respect to any of formulae (I)-(X), wherein $R^5$ is a nitrogen-containing heterocycloalkyl (e.g., one of those described above), bound through one of its nitrogen atoms to the arylene or the heteroarylene.

In certain embodiments, $R^5$ has the structure

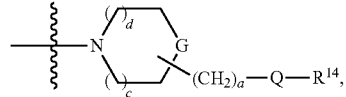

in which G is oxygen, carbon (i.e., C($R^{14}$)$_2$), sulfur (i.e., S, SO or SO$_2$) or nitrogen (i.e., NR$^{14}$); a is 0, 1, 2, or 3; c is 0 or 1; d is 0 or 1; Q is a single bond, O, S(O)$_{0-2}$, or NR$^{14}$; and each $R^{14}$ is hydrogen, methyl, ethyl or propyl. For example, in certain embodiments the —(CH$_2$)$_a$-Q-R$^{14}$ moiety can be hydroxymethyl, methoxymethyl, ethoxymethyl, 2-hydroxyethyl, 2-methyoxyethyl, or 2-ethoxyethyl. In other embodiments, the —(CH$_2$)$_a$-Q-R$^{14}$ moiety can be aminomethyl, (methylamino)methyl, (ethylamino)methyl, 2-aminoethyl, 2-(methylamino)ethyl, or 2-(ethylamino)methyl. In other embodiments, a is 0. The —(CH$_2$)$_a$-Q-R$^{14}$ moiety can, for example, be attached to the nitrogen-containing heterocycloalkyl at a ring position adjacent the G moiety. Alternatively, the —(CH$_2$)$_a$-Q-R$^{14}$ moiety can, for example, be attached to the nitrogen-containing heterocycloalkyl at a ring position adjacent the nitrogen. In other embodiments, for example, when G is nitrogen or carbon, the —(CH$_2$)$_a$-Q-R$^{14}$ moiety can be attached to the nitrogen-containing heterocycloalkyl through the G moiety. In certain embodiments, both c and d are 1. In other embodiments, c is 0 and d is 1. In additional embodiments, both c and d are 0.

In other embodiments, $R^5$ has the structure

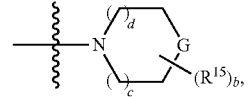

in which G is oxygen, carbon (i.e., C($R^{14}$)$_2$), sulfur (i.e., S, SO or SO$_2$) or nitrogen (i.e., NR$^{14}$); b is 1 or 2; and when b is 1, $R^{15}$ is alkyl (e.g., methyl, propyl such as isopropyl), heterocycloalkyl (e.g., morpholinyl, piperidinyl, piperazinyl, pyrolidinyl), cyano or —C(O)NHR$^{14}$, and when b is 2, both $R^{15}$ are substituted on the same carbon and are halogen, or come together to form oxo, =CHR$^{14}$ (e.g., =CH$_2$) or a spiro-fused cycloalkyl or heterocycloalkyl, in which each $R^{14}$ is hydrogen, methyl, ethyl or propyl. The $R^{15}$ moiety or moieties can, for example, be attached to the nitrogen-containing heterocycloalkyl at a ring position adjacent the G moiety. Alternatively, the $R^{15}$ moiety or moieties can, for example, be attached to the nitrogen-containing heterocycloalkyl at a ring position adjacent the nitrogen. In other embodiments, for example, when G is carbon, the $R^{15}$ moiety or moieties can be attached to the nitrogen-containing heterocycloalkyl through the G moiety. In certain embodiments, both c and d are 1. In other embodiments, c is 0 and d is 1. In additional embodiments, both c and d are 0.

In yet another embodiment, the disclosure provides compounds as described above with respect to any of formulae (I)-(X), wherein $R^5$ is tetrahydropyranyl, or tetrahydrofuranyl.

In certain embodiments, the disclosure provides compounds as described above with respect to any of formulae (I)-(X), wherein $R^5$ is cyclobutyl, cyclopentyl, cyclohexyl, cycloheptyl, bicyclo[2.2.2]octyl, bicycle[2.2.1]heptyl.

In another embodiment, the disclosure provides compounds as described above with respect to any of formulae (I)-(X), wherein $R^5$ is cyclohexyl or cyclopentyl.

In certain embodiments, the disclosure provides compounds as described above with respect to any of formulae (I)-(X), wherein $R^5$ is selected from the group consisting of:

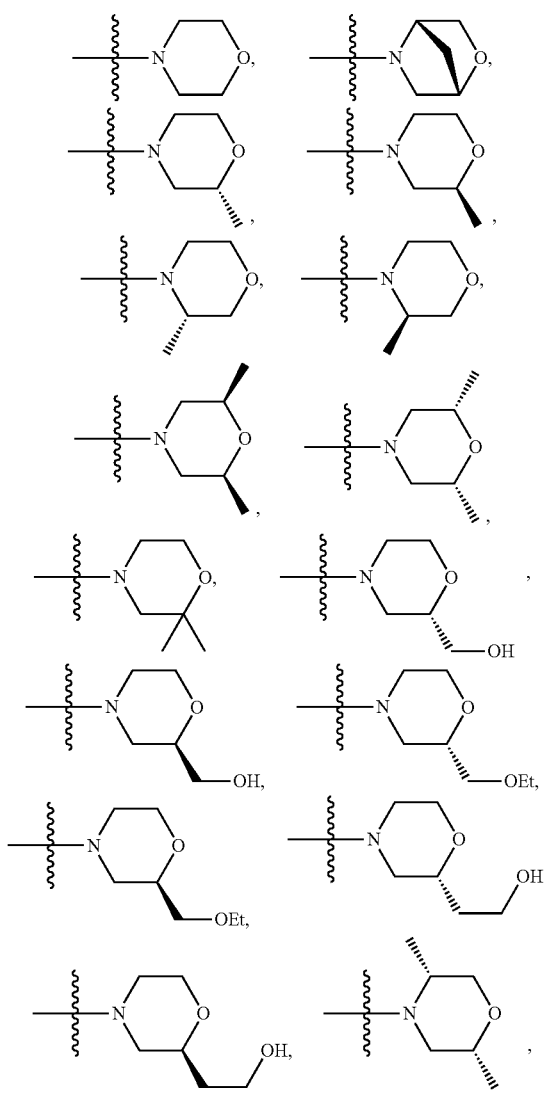

-continued

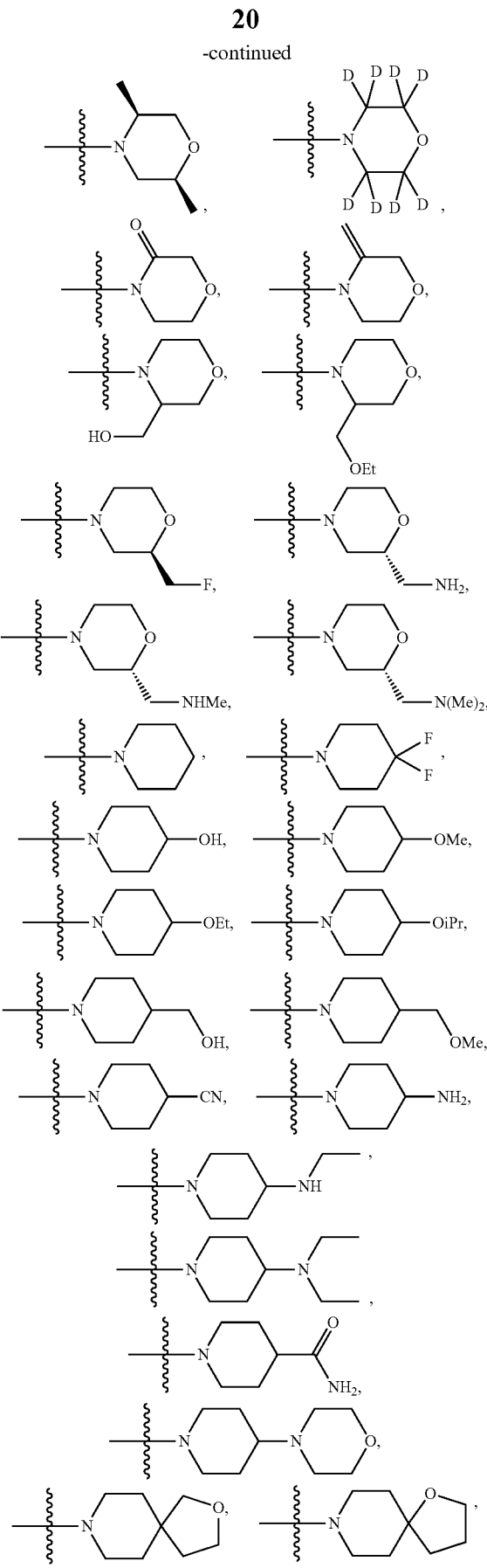

-continued

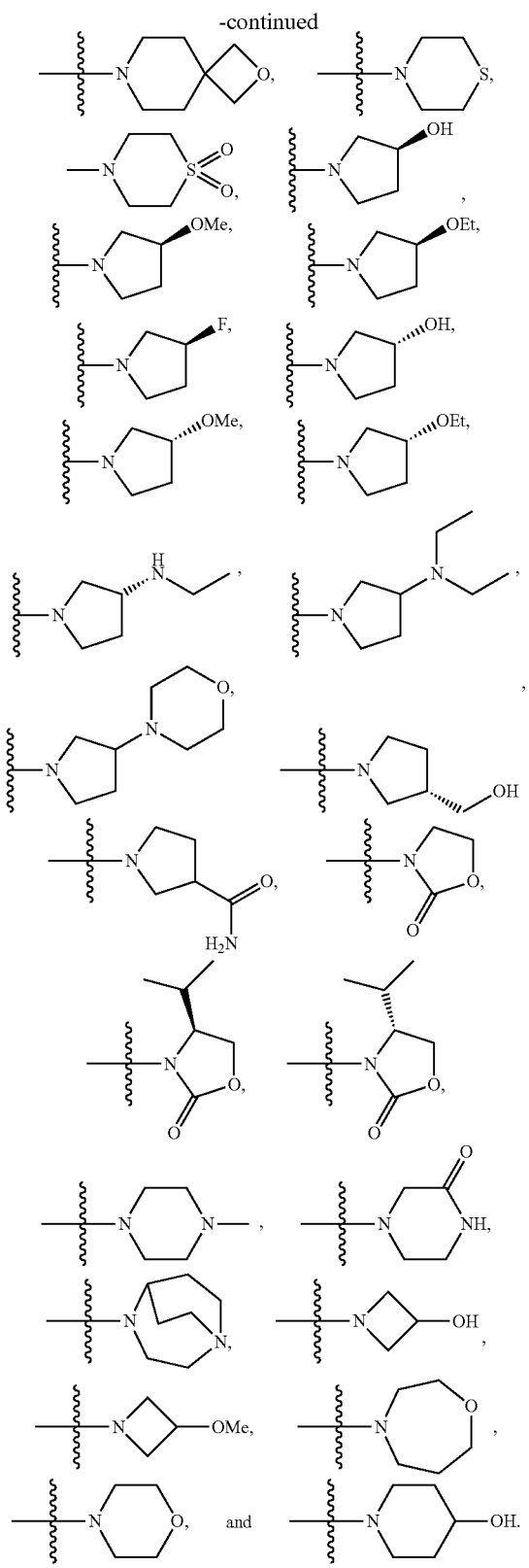

In one embodiment, the disclosure provides compounds as described above with respect to any of formulae (I)-(X), wherein $R^5$ is —$N(R^7)_2$, in which each $R^7$ is independently selected from hydrogen, $C_1$-$C_6$ alkyl, $C_2$-$C_6$ alkenyl, $C_2$-$C_6$ alkynyl, halo($C_1$-$C_6$ alkyl), hydroxy($C_1$-$C_6$ alkyl), ($C_1$-$C_6$ alkoxy)$C_1$-$C_6$ alkyl, aryl, heteroaryl, heterocycloalkyl, (aryl)$C_1$-$C_6$ alkyl, (heteroaryl)$C_1$-$C_6$ alkyl, and (heterocycloalkyl)$C_1$-$C_6$ alkyl.

In another embodiment, the disclosure provides compounds as described above with respect to any of formulae (I)-(X), wherein $R^5$ is —$N(R^7)_2$, in which each $R^7$ is independently selected from $C_1$-$C_6$ alkyl, ($C_1$-$C_6$ alkoxy)$C_1$-$C_6$ alkyl, heterocycloalkyl, and (heterocycloalkyl)$C_1$-$C_6$ alkyl.

In another embodiment, the disclosure provides compounds as described above with respect to any of formulae (I)-(X), wherein $R^5$ is —$N(C_1$-$C_6$ alkyl)$R^7$, in which $R^7$ is $C_1$-$C_6$ alkyl, ($C_1$-$C_6$ alkoxy)$C_1$-$C_6$ alkyl, heterocycloalkyl, and (heterocycloalkyl)$C_1$-$C_6$ alkyl. For example, the —$N(C_1$-$C_6$ alkyl)$R^7$ can be —$N(CH_3)R^7$.

In another embodiment, the disclosure provides compounds as described above with respect to any of formulae (I)-(X), wherein $R^5$ is —$NHR^7$, in which $R^7$ is $C_1$-$C_6$ alkyl, ($C_1$-$C_6$ alkoxy)$C_1$-$C_6$ alkyl, heterocycloalkyl, and (heterocycloalkyl)$C_1$-$C_6$ alkyl. For example, $R^7$ can be $C_1$-$C_6$ alkyl, such as methyl, ethyl or propyl.

In certain embodiments, the disclosure provides compounds as described above with respect to any of formulae (I)-(X), wherein $R^5$ is selected from the group consisting of:

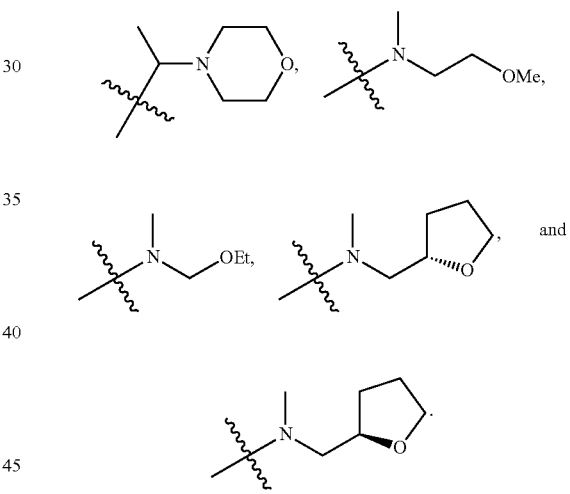

In another embodiment, the disclosure provides compounds as described above with respect to any of formulae (I)-(X), wherein $R^5$ is heteroaryl. For example, the heteroaryl can be pyridyl. In other embodiments, the heteroaryl can be selected from, for example, pyrazinyl, pyrimidinyl, furyl, oxazolyl, thiazolyl and thienyl. The heteroaryl $R^5$ moiety can be unsubstituted or can be substituted, as described above.

In another embodiment, the disclosure provides compounds as described above with respect to any of formulae (I)-(X), wherein $R^5$ is aryl. For example, the aryl can be phenyl. In other embodiments, the aryl can be naphthyl. The aryl $R^5$ moiety can be unsubstituted or can be substituted, as described above.

In another embodiment, the disclosure provides compounds as described above with respect to any of formulae (I)-(X), wherein $R^5$ is $C_1$-$C_6$ alkyl. For example, the $C_1$-$C_6$ alkyl can be methyl. In certain embodiments, no $R^9$ are substituted on the arylene or heteroarylene.

In one embodiment, the disclosure provides compounds of formula (XI):

(XI)

or a pharmaceutically acceptable salt thereof, wherein:
$R^1$ is hydrogen, $C_1$-$C_6$ alkyl, or $R^8$;
$R^2$ and $R^3$ are independently selected from hydrogen, $C_1$-$C_6$ alkyl, or $R^2$ and $R^3$ together with the carbon to which they are attached form $C_3$-$C_6$ cycloalkyl;
$R^4$ is halogen;
$R^5$ is $C_1$-$C_6$ alkyl, —$N(R^7)_2$, aryl optionally substituted with 1, 2, 3, or 4 $R^6$ groups, heteroaryl optionally substituted with 1, 2, 3, or 4 $R^6$ groups, or heterocycloalkyl optionally substituted with 1, 2, 3, 4, 5, 6, 7, or 8 $R^6$ groups, in which
each $R^6$ is independently selected from deuterium, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), (($C_1$-$C_6$ alkyl)amino)($C_1$-$C_6$ alkyl), (di($C_1$-$C_6$ alkyl)amino)($C_1$-$C_6$ alkyl), —C(O)OH, —C(O)NH$_2$, $C_3$-$C_8$ cycloalkyl, aryl, heteroaryl, and heterocycloalkyl, or two $R^6$ groups form a spiro-fused $C_3$-$C_6$ cycloalkyl, a spiro-fused heterocycloalkyl, oxo, =CH$_2$, or =CH($C_1$-$C_6$ alkyl); and
each $R_7$ is independently selected from hydrogen, $C_1$-$C_6$ alkyl, $C_2$-$C_6$ alkenyl, $C_2$-$C_6$ alkynyl, halo($C_1$-$C_6$ alkyl), hydroxy($C_1$-$C_6$ alkyl), ($C_1$-$C_6$ alkoxy)$C_1$-$C_6$ alkyl, aryl, heteroaryl, heterocycloalkyl, (aryl)$C_1$-$C_6$ alkyl, (heteroaryl)$C_1$-$C_6$ alkyl, and (heterocycloalkyl)$C_1$-$C_6$ alkyl; and
$R^8$ is selected from —$(CR^{11}R^{11})_k$—O—P(O)(OR$^{12}$)$_2$, and in which
each $R^{11}$ is independently selected from hydrogen, $C_1$-$C_6$ alkyl, aryl, and (aryl)$C_1$-$C_6$ alkyl, in which each alkyl or aryl is optionally substituted with halogen, hydroxy, $C_1$-$C_6$ alkoxy, aryloxy, or ($C_1$-$C_6$ alkyl)aryloxy, or two $R_{11}$ groups together with the carbon to which they are attached form $C_3$-$C_6$ cycloalkyl,
each $R^{12}$ is independently selected from hydrogen, $C_1$-$C_6$ alkyl, aryl, (aryl)$C_1$-$C_6$ alkyl, —$(CR^{11}R^{11})_k$—OR$^{16}$, —$(CR^{11}R^{11})_k$—O—C(O)R$^{16}$, —$(CR^{11}R^{11})_k$—O—C(O)OR$^{16}$, —$(CR^{11}R^{11})_k$—S—C(O)R$^{16}$, —$(CR^{11}R^{11})_k$—S—C(O)OR$^{16}$, —$(CR^{11}R^{11})_k$—NH—C(O)R$^{16}$, —$(CR^{11}R^{11})_k$—NH—C(O)OR$^{16}$ and —Si($R^{11}$)$_3$, in which each alkyl or aryl is optionally substituted with halogen, hydroxy, $C_1$-$C_6$ alkoxy, aryloxy, or ($C_1$-$C_6$ alkyl)aryloxy, and each $R^{16}$ is independently selected from hydrogen, $C_1$-$C_6$ alkyl, aryl, and (aryl)$C_1$-$C_6$ alkyl,
each $R^{13}$ is independently selected from hydrogen, $C_1$-$C_6$ alkyl, aryl, (aryl)$C_1$-$C_6$ alkyl, heteroaryl, and heterocycloalkyl,
each k is 1, 2 or 3,
each m is 0, 1, or 2, and
each n is 1, 2 or 3;
each $R^9$ is independently selected from halogen, cyano, $C_1$-$C_6$ alkyl, halo($C_1$-$C_6$ alkyl), $C_1$-$C_6$ alkoxy, and halo($C_1$-$C_6$ alkoxy), or $R^9$ and $R^5$ together with the carbons to which they are attached form $C_5$-$C_{10}$ heterocycloalkyl;
provided the compound is not
N4-(3,4-dihydro-3-oxo-2H-pyrido[3,2-b][1,4]oxazin-6-yl)-5-fluoro-N2-(4-morpholinophenyl)-2,4-pyrimidinediamine,
N4-(2,2-dimethyl-3,4-dihydro-3-oxo-2H-pyrido[3,2-b][1,4]oxazin-6-yl)-5-fluoro-N2-(4-morpholinophenyl)-2,4-pyrimidinediamine,
N4-(2,2-dimethyl-3,4-dihydro-3-oxo-2H-pyrido[3,2-b][1,4]oxazin-6-yl)-5-fluoro-N2-(4-(4-methylpiperazin-1-yl)phenyl)-2,4-pyrimidinediamine, or
N4-(3,4-dihydro-3-oxo-2H-pyrido[3,2-b][1,4]oxazin-6-yl)-5-fluoro-N2-(4-ethoxycarbonylpiperazin-1-yl(phenyl))-2,4-pyrimidinediamine.

In one embodiment, the disclosure provides compounds of formula (XII):

(XII)

or a pharmaceutically acceptable salt thereof, wherein:
$R^1$ is hydrogen, $C_1$-$C_6$ alkyl, or $R^8$;
$R^2$ and $R^3$ are independently selected from hydrogen, $C_1$-$C_6$ alkyl, or $R^2$ and $R^3$ together with the carbon to which they are attached form $C_3$-$C_6$ cycloalkyl;
$R^4$ is halogen;
$R^5$ is $C_1$-$C_6$ alkyl, —$N(R^7)_2$, aryl optionally substituted with 1, 2, 3, or 4 $R^6$ groups, heteroaryl optionally substituted with 1, 2, 3, or 4 $R^6$ groups, or heterocycloalkyl optionally substituted with 1, 2, 3, 4, 5, 6, 7, or 8 $R^6$ groups, in which
each $R^6$ is independently selected from deuterium, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), (($C_1$-$C_6$ alkyl)amino)($C_1$-$C_6$ alkyl), (di($C_1$-$C_6$ alkyl)amino)($C_1$-$C_6$ alkyl), —C(O)OH, —C(O)NH$_2$, $C_3$-$C_8$ cycloalkyl, aryl, heteroaryl, and heterocycloalkyl, or two $R^6$ groups form a spiro-fused $C_3$-$C_6$ cycloalkyl, a spiro-fused heterocycloalkyl, oxo, =CH$_2$, or =CH($C_1$-$C_6$ alkyl); and
each $R_7$ is independently selected from hydrogen, $C_1$-$C_6$ alkyl, $C_2$-$C_6$ alkenyl, $C_2$-$C_6$ alkynyl, halo($C_1$-$C_6$ alkyl), hydroxy($C_1$-$C_6$ alkyl), ($C_1$-$C_6$ alkoxy)$C_1$-$C_6$ alkyl, aryl, heteroaryl, heterocycloalkyl, (aryl)$C_1$-$C_6$ alkyl, (heteroaryl)$C_1$-$C_6$ alkyl, and (heterocycloalkyl)$C_1$-$C_6$ alkyl; and $R^8$ is selected from —$(CR^{11}R^{11})_k$—O—P(O)(OR$^{12}$)$_2$, and

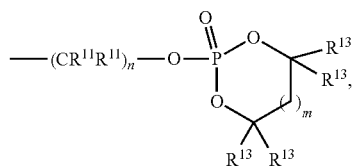

in which
  each $R^{11}$ is independently selected from hydrogen, $C_1$-$C_6$ alkyl, aryl, and (aryl)$C_1$-$C_6$ alkyl, in which each alkyl or aryl is optionally substituted with halogen, hydroxy, $C_1$-$C_6$ alkoxy, aryloxy, or ($C_1$-$C_6$ alkyl)aryloxy, or two $R_{11}$ groups together with the carbon to which they are attached form $C_3$-$C_6$ cycloalkyl,
  each $R^{12}$ is independently selected from hydrogen, $C_1$-$C_6$ alkyl, aryl, (aryl)$C_1$-$C_6$ alkyl, —$(CR^{11}R^{11})_k$—OR$^{16}$, —$(CR^{11}R^{11})_k$—O—C(O)R$^{16}$, —$(CR^{11}R^{11})_k$—O—C(O)OR$^{16}$, —$(CR^{11}R^{11})_k$—S—C(O)R$^{16}$, —$(CR^{11}R^{11})_k$—S—C(O)OR$^{16}$, —$(CR^{11}R^{11})_k$—NH—C(O)R$^{16}$, —$(CR^{11}R^{11})_k$—NH—C(O)OR$^{16}$ and —Si(R$^{11}$)$_3$, in which each alkyl or aryl is optionally substituted with halogen, hydroxy, $C_1$-$C_6$ alkoxy, aryloxy, or ($C_1$-$C_6$ alkyl)aryloxy, and each R$^{16}$ is independently selected from hydrogen, $C_1$-$C_6$ alkyl, aryl, and (aryl)$C_1$-$C_6$ alkyl,
  each $R^{13}$ is independently selected from hydrogen, $C_1$-$C_6$ alkyl, aryl, (aryl)$C_1$-$C_6$ alkyl, heteroaryl, and heterocycloalkyl,
  each k is 1, 2 or 3,
  each m is 0, 1, or 2, and
  each n is 1, 2 or 3; and
each $R^{10}$ is independently selected from halogen, cyano, $C_1$-$C_6$ alkyl, halo($C_1$-$C_6$ alkyl), $C_1$-$C_6$ alkoxy, and halo($C_1$-$C_6$ alkoxy), or $R^{10}$ and $R^5$ together with the carbons to which they are attached form $C_5$-$C_{10}$ heterocycloalkyl.

The various substituents and substitutions of compounds of formulae (XI) and (XII) can be further defined as described above with reference to any of formulae (I)-(X).

In certain embodiments, the compounds as described above with respect to any of formulae (I)-(XII) are substituted with a progroup $R^8$ that metabolizes or otherwise transforms under conditions of use to yield the active 2,4-pyrimidinediamine compounds. The progroups $R^8$ include phosphate moieties that can be cleaved in vitro by enzymes such as esterases, lipases and/or phosphatases. Such enzymes are prevalent throughout the body, residing in, for example, the stomach and digestive tract, blood and/or serum, and in virtually all tissues and organs. Such phosphate-containing $R^8$ will generally increase the water-solubility of the underlying active 2,4-pyrimidinediamine compound, making such phosphate-containing compounds suitable for modes of administration where water-solubility is desirable, such as, for example, oral, buccal, intravenous, intramuscular and ocular modes of administration.

In one embodiment of the disclosure, incorporation of a heavy atom, particularly substitution of hydrogen with deuterium, into the compounds as described above with respect to any of formulae (I)-(XII) can give rise to an isotope effect that can alter the pharmacokinetics of the compound. Stable isotope labeling of the compound of the disclosure can alter its physicochemical properties such as pKa and lipid solubility. These changes may influence the fate of the compound at different steps along its passage through the body. Absorption, distribution, metabolism or excretion can be changed.

The deuterated compound can have an increased effect and an increased duration of action on mammals at lower concentration than the undeuterated compound.

Deuterium has a natural abundance of about 0.015%. Accordingly, for approximately every 6,500 hydrogen atoms occurring in nature, there is one deuterium atom. Disclosed herein are compounds enriched in deuterium at one or more positions. Thus, deuterium containing compounds of the disclosure have deuterium at one or more positions (as the case may be) in an abundance of greater than 0.015%.

In one embodiment, a compound as described above with respect to any of formulae (I)-(XII), at a position designated as having deuterium, has a minimum isotopic enrichment factor of at least 2000 (30% deuterium incorporation) at each atom designated as deuterium in the compound, or at least 3000 (45% deuterium incorporation).

In other embodiments, a compound as described above with respect to any of formulae (I)-(XII) has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In one embodiment, the disclosure provides N4-(2,2-dimethyl-3,4-dihydro-4-[(dihydrogen phosphonoxy)methyl]-3-oxo-2H-pyrido[3,2-b][1,4]oxazin-6-yl)-5-fluoro-N2-(4-morpholinophenyl)-2,4-pyrimidinediamine, or a pharmaceutically acceptable salt thereof. This compound has formula (XIII):

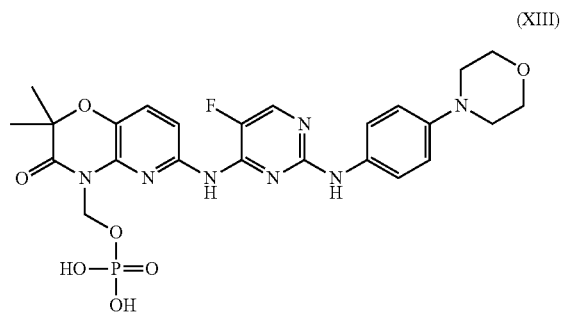 [SMILES: CC1(C)Oc2ccc(Nc3nc(Nc4ccc(N5CCOCC5)cc4)ncc3F)nc2N(COP(=O)(O)O)C1=O]

(XIII)

In another embodiment, the disclosure provides N4-(2,2-dimethyl-3,4-dihydro-3-oxo-2H-pyrido[3,2-b][1,4]oxazin-6-yl)-5-fluoro-N2-(6-morpholinopyrid-3-yl)-2,4-pyrimidinediamine, or a pharmaceutically acceptable salt thereof. This compound has formula (XIV):

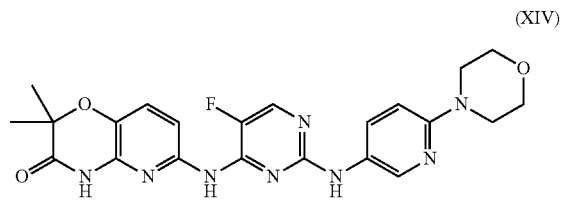 [SMILES: CC1(C)Oc2ccc(Nc3nc(Nc4ccc(N5CCOCC5)nc4)ncc3F)nc2NC1=O]

(XIV)

In yet another embodiment, the disclosure provides N4-(2,2-dimethyl-3,4-dihydro-4-[(dihydrogen phosphonoxy)methyl]-3-oxo-2H-pyrido[3,2-b][1,4]oxazin-6-yl)-5-fluoro-N2-(6-morpholinopyrid-3-yl)-2,4-pyrimidinediamine, or a pharmaceutically acceptable salt thereof. This compound has formula (XV):

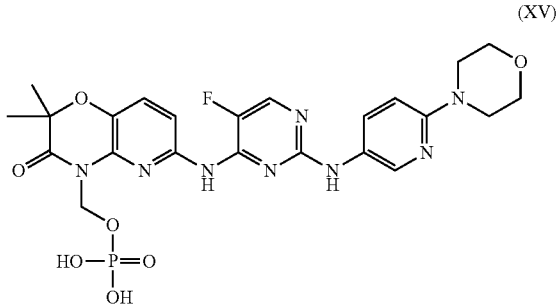 [SMILES: CC1(C)Oc2ccc(Nc3nc(Nc4ccc(N5CCOCC5)nc4)ncc3F)nc2N(COP(=O)(O)O)C1=O]

(XV)

In certain embodiments as described above with respect to any of formulae (I)-(XII), however, the compound is not N4-(2,2-dimethyl-3,4-dihydro-4-[(dihydrogen phosphonoxy)methyl]-3-oxo-2H-pyrido[3,2-b][1,4]oxazin-6-yl)-5-fluoro-N2-(4-morpholinophenyl)-2,4-pyrimidinediamine, N4-(2,2-dimethyl-3,4-dihydro-3-oxo-2H-pyrido[3,2-b][1,4] oxazin-6-yl)-5-fluoro-N2-(6-morpholinopyrid-3-yl)-2,4-pyrimidine diamine, or N4-(2,2-dimethyl-3,4-dihydro-4-[(dihydrogen phosphonoxy)methyl]-3-oxo-2H-pyrido[3,2-b][1,4]oxazin-6-yl)-5-fluoro-N2-(6-morpholinopyrid-3-yl)-2,4-pyrimidinediamine.

In another embodiment, the disclosure provides pharmaceutically acceptable salts of compounds as described above with respect to any of formulae (I)-(XV). Generally, pharmaceutically acceptable salts are those salts that retain substantially one or more of the desired pharmacological activities of the parent compound and which are suitable for administration to humans. Pharmaceutically acceptable salts include acid addition salts formed with inorganic acids or organic acids. Inorganic acids suitable for forming pharmaceutically acceptable acid addition salts include, by way of example and not limitation, hydrohalide acids (e.g., hydrochloric acid, hydrobromic acid, hydriodic, etc.), sulfuric acid, nitric acid, phosphoric acid, and the like. Organic acids suitable for forming pharmaceutically acceptable acid addition salts include, by way of example and not limitation, acetic acid, monofluoroacetic acid, difluoroacetic acid, trifluoroacetic acid, propionic acid, hexanoic acid, cyclopentanepropionic acid, glycolic acid, oxalic acid, pyruvic acid, lactic acid, malonic acid, succinic acid, malic acid, maleic acid, fumaric acid, tartaric acid, citric acid, palmitic acid, benzoic acid, 3-(4-hydroxybenzoyl)benzoic acid, cinnamic acid, mandelic acid, alkylsulfonic acids (e.g., methanesulfonic acid, ethanesulfonic acid, 1,2-ethane-disulfonic acid, 2-hydroxyethanesulfonic acid, etc.), arylsulfonic acids (e.g., benzenesulfonic acid, 4-chlorobenzenesulfonic acid, 2-naphthalenesulfonic acid, 4-toluenesulfonic acid, camphorsulfonic acid, etc.), 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. For example, in one embodiment, the salt is or di-trifluoroacetic acid salt, methanesulfonic acid salt, p-toluenesulfonic acid salt, hydrochloride salt, benzenesulfonic acid salt, or a ethanesulfonic acid salt.

Pharmaceutically acceptable salts also include salts formed when an acidic proton present in the parent compound is either replaced by an inorganic ion (e.g., an alkali metal ion such as $Na^+$, $K^+$ or $Li^+$, an alkaline earth ion such as $Ca^{2+}$ or $Mg^{2+}$, an aluminum ion, or an ammonium ion) or coordinates with an organic base (e.g., ethanolamine, diethanolamine, triethanolamine, N-methylglucamine, morpholine, piperidine, dimethylamine, diethylamine, etc.).

Specific exemplary salts include, but are not limited to, mono- and di-sodium salts, mono- and di-potassium salts, mono- and di-lithium salts, mono- and di-alkylamino salts, mono- and di-ammonium salts, mono-magnesium salts, mono-calcium salts. Such salts can be especially useful when the compound includes a free phosphate (i.e., —$P(O)(OH)_2$).

The compounds described herein, as well as the salts thereof, may also be in the form of hydrates, solvates and N-oxides, as are well-known in the art.

Many of the compounds described herein, and in particular compounds as described above with respect to any of formulae (I)-(XV), are potent inhibitors of degranulation of immune cells, such as mast, basophil, neutrophil and/or eosinophil cells or metabolize to yield 2,4-pyrimidinediamine compounds that potent inhibitors of degranulation of immune cells, such as mast, basophil, neutrophil and/or eosinophil cells. Thus, in still another aspect, the present disclosure provides methods of regulating, and in particular inhibiting, degranulation of such cells. The method generally involves contacting a cell that degranulates with an amount of a suitable compound described herein, or an acceptable salt thereof, effective to regulate or inhibit degranulation of the cell. The method may be practiced in in vitro contexts or in in vivo contexts as a therapeutic approach towards the treatment or prevention of diseases characterized by, caused by or associated with cellular degranulation.

While not intending to be bound by any theory of operation, biochemical data confirm that many 2,4-pyrimidinediamine compounds exert their degranulation inhibitory effect, at least in part, by blocking or inhibiting the signal transduction cascade(s) initiated by crosslinking of the high affinity Fc receptors for IgE ("FcεRI") and/or IgG ("FcγRI") (see, e.g., U.S. patent application Ser. No. 10/631,029 filed Jul. 29, 2003 (US 2007/0060603), international patent application no. PCT/US03/24087 (WO2004/014382), U.S. patent application Ser. No. 10/903,263 filed Jul. 30, 2004 (US2005/0234049), and international patent application no. PCT/US2004/24716 (WO 2005/016893), the disclosures of which are hereby incorporated herein by reference in their entireties.) Indeed, these active 2,4-pyrimidinediamine compounds are potent inhibitors of both FcεRI-mediated and FcγRI-mediated degranulation. As a consequence, the compounds described herein may be used to inhibit these Fc receptor signaling cascades in any cell type expressing such FcεRI and/or FcγRI receptors including but not limited to macrophages, mast, basophil, neutrophil and/or eosinophil cells.

The methods also permit the regulation of, and in particular the inhibition of, downstream processes that result as a consequence of activating such Fc receptor signaling cascade(s). Such downstream processes include, but are not limited to, FcεRI-mediated and/or FcγRI-mediated degranulation, cytokine production and/or the production and/or release of lipid mediators such as leukotrienes and prostaglandins. The method generally involves contacting a cell expressing an Fc receptor, such as one of the cell types discussed above, with an amount of a compound described herein, or an acceptable salt thereof, effective to regulate or inhibit the Fc receptor signaling cascade and/or a downstream process effected by the activation of this signaling cascade. The method may be practiced in in vitro contexts or in in vivo contexts as a therapeutic approach towards the treatment or prevention of diseases characterized by, caused by or associated with the Fc receptor signaling cascade, such as diseases effected by the release of granule specific chemical mediators upon degranulation, the release and/or synthesis of cytokines and/or the release and/or synthesis of lipid mediators such as leukotrienes and prostaglandins.

In yet another aspect, the present disclosure provides methods of treating and/or preventing diseases characterized by, caused by or associated with the release of chemical mediators as a consequence of activating Fc receptor signaling cascades, such as FcεRI and/or FcγRI-signaling cascades. The methods may be practiced in animals in veterinary contexts or in humans. The methods generally involve administering to an animal subject or a human an amount of a compound as described above with respect to any of formulae (I)-(XV), or an acceptable salt thereof, effective to treat or prevent the disease. As discussed previously, activation of the FcεRI or FcγRI receptor signaling cascade in certain immune cells leads to the release and/or synthesis of a variety of chemical substances that are pharmacological mediators of a wide variety of diseases. Any of these diseases may be treated or prevented according to the methods described herein.

Many of the compounds of the disclosure are also potent inhibitors of the tyrosine kinase Syk kinase. Thus, in still another aspect, the present disclosure provides methods of regulating, and in particular inhibiting, Syk kinase activity. The method generally involves contacting a Syk kinase or a cell comprising a Syk kinase with an amount of a suitable compound as described above with respect to any of formulae (I)-(XV), or an acceptable salt thereof, effective to regulate or inhibit Syk kinase activity. In one embodiment, the Syk kinase is an isolated or recombinant Syk kinase. In another embodiment, the Syk kinase is an endogenous or recombinant Syk kinase expressed by a cell, for example a mast cell or a basophil cell. The method may be practiced in in vitro contexts or in in vivo contexts as a therapeutic approach towards the treatment or prevention of diseases characterized by, caused by or associated with Syk kinase activity.

While not intending to be bound by any particular theory of operation, it is believed that such active 2,4-pyrimidinediamine compounds inhibit cellular degranulation and/or the release of other chemical mediators primarily by inhibiting Syk kinase that gets activated through the gamma chain homodimer of FcεRI. This gamma chain homodimer is shared by other Fc receptors, including FcγRI, FcγRIII and FcαRI. For all of these receptors, intracellular signal transduction is mediated by the common gamma chain homodimer. Binding and aggregation of those receptors results in the recruitment and activation of tyrosine kinases such as Syk kinase. As a consequence of these common signaling activities, compounds as described above with respect to any of formulae (I)-(XV) may be used to regulate, and in particular inhibit, the signaling cascades of Fc receptors having this gamma chain homodimer, such as FcεRI, FcγRI, FcγRIII and FcαRI, as well as the cellular responses elicited through these receptors.

Syk kinase is known to play a critical role in other signaling cascades. For example, Syk kinase is an effector of B-cell receptor (BCR) signaling and is an essential component of integrin beta(1), beta(2) and beta(3) signaling in neutrophils. Active 2,4-pyrimidinediamine compounds that are potent inhibitors of Syk kinase can be used to regulate, and in particular inhibit, any signaling cascade where Syk plays a role, such as, fore example, the Fc receptor, BCR and integrin signaling cascades, as well as the cellular responses elicited through these signaling cascades. Thus, compounds as described above with respect to any of formulae (I)-(XV) can be used to regulate such activities. The particular cellular response regulated or inhibited will depend, in part, on the specific cell type and receptor signaling cascade, as is well known in the art. Non-limiting examples of cellular responses that may be regulated or inhibited with such compounds include a respiratory burst, cellular adhesion, cellular degranulation, cell spreading, cell migration, phagocytosis (e.g., in macrophages), calcium ion flux (e.g., in mast, basophil, neutrophil, eosinophil and B-cells), platelet aggregation, and cell maturation (e.g., in B-cells).

Thus, in another aspect, the present disclosure provides methods of regulating, and in particular inhibiting, signal transduction cascades in which Syk plays a role. The method generally involves contacting a Syk-dependent receptor or a cell expressing a Syk-dependent receptor with an amount of a suitable compound described herein, or an acceptable salt thereof, effective to regulate or inhibit the signal transduction cascade. The methods may also be used to regulate, and in particular inhibit, downstream processes or cellular responses elicited by activation of the particular Syk-dependent signal transduction cascade. The methods may be practiced to regulate any signal transduction cascade where Syk is now known or later discovered to play a role. The methods may be practiced in in vitro contexts or in in vivo contexts as a therapeutic approach towards the treatment or prevention of diseases characterized by, caused by or associated with activation of the Syk-dependent signal transduction cascade. Non-limited examples of such diseases include those previously discussed.

Recent studies have shown that activation of platelets by collagen is mediated through the same pathway used by immune receptors, with an immunoreceptor tyrosine kinase motif on the FcRγ playing a pivotal role, and also that FcRγ plays a pivotal role in the generation of neointimal hyperplasia following balloon injury in mice, most likely through collagen-induced activation of platelets and leukocyte recruitment. Thus, the compounds described herein can also be used to inhibit collagen-induced platelet activation and to treat or prevent diseases associated with or caused by such platelet activation, such as, for example, intimal hyperplasia and restenosis following vascular injury.

Therapeutic Applications

Compounds as described above with respect to any of formulae (I)-(XV) are useful for treating a disease or disorder that is mediated through, or exacerbated by, the activity of a Syk in a subject in need of treatment. The present disclosure provides methods of treating conditions such as inflammatory conditions or diseases, autoimmune diseases, cell proliferative disorders, and degenerative bone disorders in a subject by administering an effective amount of a compound as described above with respect to any of formulae (I)-(XV), including a salt or solvate or stereoisomer thereof.

Inflammatory Conditions

Accordingly, the present disclosure provides methods of treating an inflammatory condition or disease in a subject by administering an effective amount of a subject compound, including a salt or solvate or stereoisomer thereof. Inflammatory conditions contemplated for therapy include acute and chronic inflammation mediated or exacerbated by Syk activity.

The subject compounds can be used to treat a variety of inflammatory conditions or diseases in which an inflammatory response is associated with the condition or disease. Diagnosis and clinical indications of such diseases and conditions will be well known to the skilled artisan, and guidance is provided in various reference works, such as The Merck Manual of Diagnosis and Therapy, 1999, 17$^{th}$ Ed., John Wiley & Sons; and International Classification of Disease and Related Health Problems (ICD 10), 2003, World Health Organization.

The disclosure provides methods of regulating or inhibiting signal transduction cascades in which Syk plays a role. The method generally involves contacting a Syk-dependent receptor or a cell expressing a Syk-dependent receptor with an amount of a subject compound effective to regulate or inhibit the signal transduction cascade. The methods may also be used to regulate or inhibit downstream processes or cellular responses elicited by activation of the particular Syk-dependent signal transduction cascade. The methods may be practiced in in vitro contexts or in in vivo contexts as a therapeutic approach towards the treatment or prevention of diseases characterized by, caused by or associated with activation of the Syk-dependent signal transduction cascade.

Syk is involved in release of preformed mediators of atopic and/or Type I hypersensitivity reactions (e.g., histamine, proteases such as tryptase, etc.) via the degranulation process in mast cells and basophil cells. Such atopic or Type I hypersensitivity reactions include, but are not limited to, anaphylactic reactions to environmental and other allergens (e.g., pollens, insect and/or animal venoms, foods, drugs, contrast dyes, etc.), anaphylactoid reactions, hay fever, allergic conjunctivitis, allergic rhinitis, allergic asthma, atopic dermatitis, eczema, urticaria, mucosal disorders, tissue disorders, and certain gastrointestinal disorders.

The immediate release of the preformed mediators via degranulation is followed by the release and/or synthesis of a variety of other chemical mediators, including, but not limited to, platelet activating factor (PAF), prostaglandins and leukotrienes (e.g., LTC4) and the de novo synthesis and release of cytokines such as TNFα, IL-4, IL-5, IL-6, IL-13, etc. These "late stage" mediators can be responsible for the chronic symptoms of the above-listed atopic and Type I hypersensitivity reactions, and in addition are chemical mediators of inflammation and inflammatory conditions, including, but not limited to, osteoarthritis, inflammatory bowel disease, ulcerative colitis, Crohn's disease, idiopathic inflammatory bowel disease, irritable bowel syndrome, spastic colon, low grade scarring, scleroderma, increased fibrosis, keloids, post-surgical scars, pulmonary fibrosis, vascular spasms, migraine, reperfusion injury, post myocardial infarction, and sicca complex or syndrome. All of these diseases may be treated or prevented according to the methods described herein.

Additional diseases which can be treated or prevented according to the subject methods include diseases associated with basophil cell and/or mast cell pathology. Examples of such diseases include, but are not limited to, diseases of the skin such as scleroderma, cardiac diseases such as post myocardial infarction, pulmonary diseases such as pulmonary muscle changes or remodeling and chronic obstructive pulmonary disease (COPD, and diseases of the gut such as inflammatory bowel syndrome (spastic colon).

Certain inflammatory diseases or disorders that can be treated using the subject compound include, but not limited to, asthma, COPD, lung inflammation, chronic granulomatous diseases such as tuberculosis, leprosy, sarcoidosis, and silicosis, nephritis, amyloidosis, rheumatoid arthritis, ankylosing spondylitis, chronic bronchitis, scleroderma, lupus, polymyositis, appendicitis, inflammatory bowel disease, Crohn's disease, ulcerative colitis, psoriasis, pelvic inflammatory disease, irritable bowel syndrome, orbital inflammatory disease, thrombotic disease, and inappropriate allergic responses to environmental stimuli such as poison ivy, pollen, insect stings and certain foods, including atopic dermatitis and contact dermatitis.

Because the exemplary compounds inhibit the FcεRI and/or FcγR signal cascades that lead to degranulation of immune cells such as mast cells, such compounds can be used to inhibit the development and progression of atherosclerosis and associated symptoms. For example, activation of the IgE receptor signal transduction pathway leads to degranulation of the cells and consequent release and/or synthesis of a host of chemical mediators, including histamine, proteases (e.g., tryptase and chymase), lipid mediators such as leukotrienes (e.g., LTC4), platelet-activating factor (PAP) and prostaglandins (e.g., PGD2) and a series of cytokines, including TNF-a, IL-4, IL-13, IL-5, IL-6, IL-8, GMCSF, VEGF and TGF-β. The release and/or synthesis of these mediators from mast cells can lead to degradation of the extracellular matrix, deposition of fatty streaks in the vasculature and rupture of existing atherosclerotic plaques. Accordingly, inhibition of mast cell degranulation using the presently disclosed compounds can be used to treat atherosclerosis.

The subject compounds can be used, either independently or in combination with other anti-inflammatory compositions, as discussed below.

Autoimmune Diseases

The present disclosure provides methods of treating an autoimmune disease in a subject by administering an effective amount of a subject compound, including a salt or solvate or stereoisomer thereof.

The subject compounds can also be used to treat or prevent autoimmune diseases and/or symptoms of such diseases. Autoimmune diseases that can be treated or prevented with the subject compounds include those diseases that are commonly associated with nonanaphylactic hypersensitivity reactions (Type II, Type III and/or Type IV hypersensitivity reactions) and/or those diseases that are mediated, at least in part, by activation of the FcγR signaling cascade in monocyte cells. Such autoimmune disease include autoimmune diseases that are frequently designated as single organ or single cell-type autoimmune disorders and autoimmune disease that are frequently designated as involving systemic autoimmune disorder. Non-limiting examples of diseases frequently designated as single organ or single cell-type autoimmune disorders include: Hashimoto's thyroiditis, autoimmune hemolytic anemia, autoimmune atrophic gastritis of pernicious anemia, autoimmune encephalomyelitis, autoimmune orchitis, Goodpasture's disease, autoimmune thrombocytopenia, sympathetic ophthalmia, myasthenia gravis, Graves' disease, primary biliary cirrhosis, chronic aggressive hepatitis, ulcerative colitis, glomerulonephritis and membranous glomerulopathy. Non-limiting examples of diseases often designated as involving systemic autoimmune disorder include: systemic lupus erythematosis, rheumatoid arthritis, Sjogren's syndrome, Reiter's syndrome, polymyositis-dermatomyositis, systemic sclerosis, polyarteritis nodosa, multiple sclerosis and bullous pemphigoid.

As a certain example of a treatment, rheumatoid arthritis is thought to be an autoimmune disease that commonly affects the joints in a polyarticular manner (polyarthritis). The disease is characterized by chronically inflamed synovium that is densely crowded with lymphocytes. Chronic inflammatory condition arising from an autoimmune reaction can lead to led to erosion and destruction of the joint surface, which impairs the range of joint movement and leads to deformity. The subject compounds can be used to treat or ameliorate any one, several or all of these symptoms of rheumatoid arthritis.

The subject compounds can be used, either independently or in combination with other anti-inflammatory compositions, as discussed below.

Cellular Proliferation Disorders

Although the art suggests that Syk may act as a tumor suppressor, the present disclosure is based on indications that Syk functions contrary to that posited role. For instance, forced expression of Syk kinase in tumor cells does not appear to reverse the transformed phenotype of tumor cells. To the contrary, it is suggested herein that Syk acts in an oncogenic capacity to promote and/or maintain cell proliferation. With this perspective on the role of Syk, the present disclosure provides methods of treating a cell proliferative disorder in a subject by administering an effective amount of a subject compound, including a salt or solvate or stereoisomer thereof.

Generally, cell proliferative disorders treatable with the subject compound disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, but not limited to, breast cancer, ovarian cancer, renal cancer, gastrointestinal cancer, kidney cancer, bladder cancer, pancreatic cancer, lung squamous carcinoma, and adenocarcinoma.

In certain instances, the cell proliferative disorder treated is a hematopoietic neoplasm, which is aberrant growth of cells of the hematopoietic system.

In certain instances, the hematopoietic neoplasm is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Certain B-cell neoplasms are precursor B-lymphoblastic leukemia/lymphoma (precursor B-cell acute lymphoblastic leukemia) while certain mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms can be further subdivided into precursor T-cell neoplasm and mature (peripheral) T-cell neoplasms. A certain precursor T-cell neoplasm is precursor T-lymphoblastic lymphoma/leukemia (precursor T-cell acute lymphoblastic leukemia) while certain mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, mycosis fungoides/Sezary syndrome, anaplastic large-cell lymphoma, T/null cell, primary cutaneous type, peripheral T-cell lymphoma, not otherwise characterized, angioimmunoblastic T-cell lymphoma, anaplastic large-cell lymphoma, T/null cell, primary systemic type. Another member of lymphoid neoplasms is Hodgkin's lymphoma, also referred to as Hodgkin's disease. Certain diagnoses of this class that include, among others, nodular lymphocyte-predominant Hodgkin's lymphoma, and various classical forms of Hodgkin's disease, certain members of which are nodular sclerosis Hodgkin's lymphoma (grades 1 and 2), lymphocyte-rich classical Hodgkin's lymphoma, mixed cellularity Hodgkin's lymphoma, and lymphocyte depletion Hodgkin's lymphoma.

In certain instances, the hematopoietic neoplasm is a myeloid neoplasm. This group includes a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Certain myeloproliferative diseases include chronic myelogenous leukemia (e.g., Philadelphia chromosome positive (t(9;22)(qq34;q11)), chronic neutrophilic leukemia, chronic eosinophilic leukemialhypereosinophilic syndrome, chronic idiopathic myelofibrosis, polycythemia vera, and essential thrombocythemia. Certain myelodysplastic/myeloproliferative diseases include chronic myelomonocytic leukemia, atypical chronic myelogenous leukemia, and juvenile myelomonocytic leukemia. Certain myelodysplastic syndromes include refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome with t(9;12)(q22;p12) (TEL-Syk fusion).

In certain instances, the composition can be used to treat acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Certain AMLs with recurrent cytogenetic translocations include, among others, AML with t(8;21)(q22;q22), AML1 (CBF-alpha)/ETO, acute promyelocytic leukemia (AML with t(15;17)(q22;q11-12) and variants, PML/RAR-alpha), AML with abnormal bone marrow eosinophils (inv(16)(p13q22) or t(16;16)(p13;q11), CBFb/MYH11X), and AML with 11q23 (MLL) abnormalities. Certain AML with multilineage dysplasia are those that are associated with or without prior myelodysplastic syndrome. Other acute myeloid leukemias not classified within any definable group include, AML minimally differentiated, AML without maturation, AML with maturation, acute myelomonocytic leukemia, acute monocytic leukemia, acute erythroid leukemia, acute megakaryocytic leukemia, acute basophilic leukemia, and acute panmyelosis with myelofibrosis.

In certain instances, cell proliferative disorders include virally mediated tumors. These can arise from infection of cells by an oncogenic virus that has a capability of transforming a normal cell into a tumor cell.

In certain instances, the virally mediated tumor can be associated with any virus that encodes an immunoreceptor tyrosine-based activation motif (ITAM) capable of modulating Syk activity. This motif can refer to a conserved amino acid sequence motif that functions by interacting with and activating nonreceptor tyrosine kinases. ITAM motifs are found in, among others, the p and y chains of FcεRI, the ε subunit of the T cell receptor, and immunoglobulin β (Igβ) and Igα of the B cell receptor. The canonical sequence motif is typically $Yxx(L/I)x_{6-8}Yxx(L/I)$, where x represents any amino acid.

Accordingly, in certain instances, the virally mediated tumor can be associated with Kaposi's sarcoma (KS) associated herpes virus, a lymphotropic virus implicated in Kaposi's sarcoma. The KS associated herpes virus encodes a transmembrane protein termed KI having an immunoreceptor tyrosine-based activation motif (ITAM)-like sequence.

In certain instances, the virally mediated tumor can be associated with Epstein Barr Virus (EBV). Epstein Barr Virus is a member of the Herpesviridae family that, following primary infection, replicates in the epithelial cells of the oropharynx and infect recirculating B lymphocytes. EBV infection can be associated with Burkitt's lymphoma, Hodgkin's lymphoma, and adult T cell leukemia.

In certain instances, the virally mediated tumor can be associated with Human T-cell Lymphotropic Virus (HTLV-1 virus), a retrovirus in the same class of virus as HIV-1.

In certain instances, the virally mediated tumor can be associated with mammary tumor virus (MTV). ITAM sequences can be found within the Env gene of murine mammary tumor virus (MMTV), a B type retrovirus identified as an etiological agent for breast cancer in mice. Murine mammary tumor virus-like sequences can be present in human cancers, such as breast cancer and T cell lymphomas.

It is to be understood that use of subject composition for treating virally mediated tumors is not limited to tumors associated with the viruses specified above. As noted, any tumors associated with an oncogenic virus in which Syk is activated as part of its oncogenic mechanism, whether or not it involves ITAM sequences, can be targeted using the subject compounds.

In certain instances, the subject compounds can be used for the treatment of tumor metastasis. Metastasis is a characteristic of malignant tumor cells whereby tumor cells detach from its site of origin and then spread to colonize at other sites. These secondary tumors can form in tissues unrelated to the cells from which the tumor cells originate.

Various tumor types capable of metastasis can be treated with the subject compounds. Such tumors include, but not limited to, breast cancer, ovarian cancer, renal cancer, gastrointestinal cancer, kidney cancer, bladder cancer, pancreatic cancer, lung squamous carcinoma, and adenocarcinoma. Therapeutic treatment to attenuate the metastasis of established tumors can follow a diagnosis of metastasis. If no diagnosis of metastasis has been made, the subject compounds can be administered prophylactically to reduce the probability of metastasis.

The subject compounds can be used, either independently or in combination with other chemotherapeutic compositions, as recognized in the art.

Degenerative Bone Disorders

The present disclosure provides methods of treating a degenerative bone disorder in a subject by administering an effective amount of a subject compound, including a salt or solvate or stereoisomer thereof.

The subject compounds can be used for treating degenerative bone disorders as well as prophylactic approaches for preventing bone loss that can lead to increased fracture risk. These treatments are based on the use of Syk inhibitors to attenuate or inhibit osteoclastogenesis and osteoclast activity, thereby decreasing or inhibiting the excessive bone loss associated with abnormal activity of osteoclasts. In addition, in those degenerative bone disorders where inappropriate remodeling results in compromised bone integrity but without significant bone loss, an increase in bone mass resulting from inhibition of bone resorption can increase bone strength sufficiently to decrease the fracture risk. The subject compounds can be used independently or in combination with other modulators of bone remodeling (i.e., antiresorptive agents and osteo-anabolic agents), for treatment as well as prophylaxis.

The diagnosis of a particular disorder can be based on clinical presentations typically used by those skilled in the art to diagnose the disorder. As further discussed herein, other diagnostic criteria such as the presence of biochemical and molecular markers of the disease, can be used independently or as a supplement to the examination of the clinical presentations. Standard diagnostic criteria can be found in various references, including, by way of example and not limitation, the World Health Organization's International Classification of Diseases, Tenth Revision (1CD-i 0); Resnick, D., Diagnosis of Bone and Joint Disorders, 4th Ed., W.B. Saunders Company (2002); and AACE Medical Guidelines for Clinical Practice for the Prevention and Treatment of Postmenopausal Osteoporosis: 2001 Edition, with Selected Updates for 2003.

In certain instances, the subject compounds can be used to treat primary osteoporosis, which is a loss of bone mass unrelated to any other underlying disease or illness. There are general types of primary osteoporosis. Type I, also referred to as high turnover or postmenopausal osteoporosis, is correlated with a decrease in hormone levels secreted by the ovaries in the postmenopausal period. Type II, also referred to as low turnover or senile osteoporosis, can arise when the processes of bone resorption and bone formation are not coordinated such that there is a net excess of bone resorption over bone formation.

Other forms of primary osteoporosis are idiopathic osteoporosis, an osteoporotic condition where there is no identifiable cause for the bone loss. Idiopathic osteoporosis can affect children and adults. Juvenile osteoporosis is osteoporosis occurring in children between the ages of about 8 and about 14 years of age.

In certain instances, the subject compounds can be used to treat osteodystrophy, a degeneration of bone resulting from compromised kidney function. Clinical presentations of osteodystrophy can be in the form of osteoporosis, osteomalacia, osteitis fibrosa, osteoscierosis, osteomalacia, and secondary hyperparathyroidism.

In certain instances, the subject compounds can be used to treat Paget's Disease, also known as osteitis deformans.

In certain instances, the subject compounds can be used to treat periodontal disease.

In certain instances, the subject compounds can be used to treat degenerative bone disorders arising from a secondary condition, where the bone degeneration is a consequence of the underlying medical condition or disease. Thus, subject compounds can be administered to subjects with the secondary condition to treat or prevent degenerative bone disorder associated with the secondary condition.

A certain secondary condition is encrinopathy, which is a condition characterized by abnormal hormone secretion. Abnormal hormone secretion can be either an increase or reduction in hormone levels. Various hormones can affect bone metabolism, including but not limited to, estrogen, testosterone, growth hormone, calcitonin, parathyroid hormone, parathyroid hormone related protein, glucocorticoids, and calcitriol. Various forms of endocrinopathies are associated with loss of bone mass and corresponding bone degeneration. In certain instances, the subject compounds can be used to treat bone degeneration arising from hypercorticolism or an abnormal increase in the production of glucocorticoids by the adrenal glands (e.g., Cushing's syndrome). In certain instances, the subject compounds can be used to treat bone degeneration arising from hypogonadism. In certain instances, the bone degeneration treatable with the subject compounds can be bone loss associated with destruction of one or both of the gonads, such as by surgery (i.e., ovariectomy or oophorectomy). In certain instances, the subject compounds can be used to treat bone degeneration arising from hyperparathyroidism.

In certain instances, the methods can be directed to use of the subject compounds to treat bone degeneration associated with heritable genetic disorders. Thus, subject compounds can be administered to subjects with a heritable genetic disorder to treat or prevent degenerative bone disorder associated with the heritable genetic disorder Inherited genetic disorders can arise from, among others, single gene inheritance, multifactorial or polygenic inheritance, chromosome abnormalities, and parental imprinting abnormalities. Various inherited genetic abnormalities affecting bone metabolism have been identified, including, osteogenesis imperfecta, homocystinurea, gonadal dysgenesis, and hypophosphatasia.

It is to be understood that the use of Syk inhibitors are not limited to the degenerative bone disorders described herein, but may be applied to degenerative bone disorder characterized by a net excess of bone resorption over bone formation. This condition may arise from increased osteoclastogenesis, increased osteoclast activation, decreased osteoblastogeneis, decreased osteoblast activity, or a combination of increased osteclastogenesis and decreased osteoblastogenesis. Thus, the methods herein encompass treatments for degenerative bone disorders generally in which there is an imbalance of bone resorption over bone formation.

The subject compounds can be used, either independently or in combination with other bone modulating agents, as recognized in the art. In addition to the treatment of degenerative bone disorders, the subject compounds can be used, either independently or in combination with bone modulating agents, as prophylaxis to prevent bone loss in subjects at risk of bone loss and increased fracture risk.

Combination Therapy

The subject compounds may be administered individually or as compatible combinations along with an anti-inflammatory agent. Different combinations of the subject compounds may be used to adjust bioavailability, duration of effect, and efficacy for the particular inflammatory condition. Identifying appropriate combinations for the purposes herein are within the skill of those in the art.

Steroidal Anti-Inflammatory Agents

For treating inflammatory disorders, the subject compounds can be administered in combination with an additional chemotherapeutic agent, such as an anti-inflammatory agent. In certain instances, the anti-inflammatory agent for use in combination with the presently disclosed compounds is a steroidal anti-inflammatory agent. As used herein, "steroidal anti-inflammatory agent" or "anti-inflammatory steroid" is a compound or composition based on a structure with a steroid nucleus and having anti-inflammatory activity, either alone or in combination with other agents. With the exception of vitamin D compounds, steroid compounds are derived from a steroid nucleus based on a saturated tetracyclic hydrocarbon, 1,2-cyclopentanoperhydrophenanthrene, also referred to as sterane or gonane. Steroidal compounds include both naturally occurring and synthetically produced steroidal compounds. Different groups of steroid compounds include, among others, adrenocorticosteroids, estrogens/progestins, and androgens.

In certain instances, the steroidal anti-inflammatory agents are adrenocorticosteroids, which refer to steroidal compounds that are released from the adrenal cortex. These steroid compounds include the groups of glucocorticosteroids and mineralocorticosteoids. As used herein, adrenocorticosteroids also include various synthetic analogs that display the biological properties displayed by the naturally occurring steroids. Certain structural features may enhance anti-inflammatory activities of steroids, such as all trans steroid skeleton, presence of $\Delta^4$-3-keto, 11β-OH, 17β-OH, and substitutions at 9α-, 6α-, 16α-positions, with F>Cl>Br>I.

In certain instances, the anti-inflammatory steroidal agent is a glucocorticosteroid (synonymously "glucocorticoid"). Various anti-inflammatory glucocorticoids can be used. These include, by way of example and not limitation, natural and synthetic steroidal compounds such as 21-acetoxypregnenolone, alclometasone, algestone, amcinonide, beclomethasone, budesonide, chloroprednisone, ciclesonide, clobetasol, clobetasone, clocortolone, cloprednol, corticosterone, cortisone, contrivazol, deflazacort, desonide, desoximetasone, dexamethansone, diflorasone, diflucortolone, diflupredate, enoxolone, fluazacort, flurandrenolone acetonide, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinode, halobetasol propionate, halometasone, halopredone acetate, hydrocortamate, hydrocortisone, hydrocortisone 17-butyrate, hydrocortisone 17-valerate, loteprednol etabonate, maziprednone, medrysone, meprednisone, methylprednisolone, mometasone furoate, paramethasone, prednicarbate, prednisolone, prednisolone 21-dimethylaminoacetate, prenisolone sodium phosphate, prednisone, prednival, prednylidene, rimexolone, tixocortol, triamcinolone, triamcinolone acetonide, triamcinolone benetonide, and triamcinolone hexacetonide. Other glucocorticosteroids will be apparent to the skilled artisan.

In certain instances, the anti-inflammatory steroid is a mineralocorticosteroid (synonymously "mineralocorticoid"). Various mineralocorticoids include, among others, aldosterone, deoxycorticosterone, deoxycorticosterone acetate, and fludrocortisone. It is to be understood, however, that the characterization of a steroid as a glucocorticosteroid or mineralocorticosteroid are used for descriptive purposes and is not meant to be exclusionary. Glucocorticoids display some mineralocorticosteroid activity while some mineralocorticoids display some glucocorticoid activity. For the purposes herein, a mineralocorticoid with anti-inflammatory properties may be used. Generally, mineralocorticosteroids with some glucocorticosteroid activity appears to have anti-inflammatory effects. A certain anti-inflammatory mineralocorticoid is fludrocortisone.

In certain instances, the anti-inflammatory steroidal agents have varying biologic effect half-life, and can be divided into short acting, intermediate acting, or long acting steroidal compounds. Certain short-acting steroidal compounds include, by way of example and not limitation, cortisol and cortisone. Certain intermediate-acting steroidal compounds include, by way of example and not limitation, prednisone, prednisolone, triamcinolone, and methylprednisolone. Certain long-acting steroidal compounds include, by way of example and not limitation, dexamethasone, betamethasone, and budesonide.

In certain instances, the anti-inflammatory steroid is a nitro-steroidal compound. As used herein a "nitro-steroidal" compound is steroid having NO-releasing activity (the nitrosterols), and include NO-releasing forms of prednisolone, flunisolide and hydrocortisone.

In certain instances, the steroidal anti-inflammatory agent can be an inhaled steroidal agent, which is useful for nasal administration and/or absorption through the lungs. These forms are effective agents for treating asthma and reaction to inhaled allergens. Various forms of steroidal anti-inflammatory compounds formulated as inhalants include, among others, beclomethasone, bedesonide, dexamethasone, flunisolide, triamcinolone acetonide, and antedrugs noted above.

In certain instances, the steroidal anti-inflammatory agent is an estrogen or a synthetic estrogen analog. Various estrogen and estrogen analogs that may be used include, by way of example and not limitation, estrogen, 17β-estradiol, estrogen conjugates, medroxyprogesterone, 2-methoxyestradiol (estrogen metabolite), diethystilbesterol, reveratrol, phytoestrogens (e.g., genestein), and tamoxifen.

In certain instances, the steroidal anti-inflammatory compound is vitamin D or an analog thereof. Various anti-inflammatory agents of this group include, by way of example and not limitation, 7-dehydrocholesterol, cholecaciferol, ergosterol, 1,25-dihydroxyvitamin D3, and 22-ene-25-oxa-vitamin D. Other vitamin D analogs are described in U.S. Pat. Nos. 6,924,400; 6,858,595; 6,689,922; and 6,573,256.

Non-Steroidal Anti-Inflammatory Agents

In certain instances, the anti-inflammatory agent is a non-steroidal anti-inflammatory agent (NSAID). This class of agents includes a heterogeneous group of compounds with varying structures but which act through common therapeutic targets. NSAIDs are classified based on their chemical structures and biological activities. In certain instances, the NSAIDs useful with the subject compounds are non-selective COX-2 inhibitors, which inhibit the activity of both COX-1 and COX-2 isoforms. A certain non-selective COX inhibitor is salicylic acid and derivatives thereof. Certain compounds of this class include, by way of example and not limitation, acetylsalicylic acid, sodium salicylate, choline magnesium trisalicylate, salsalate, diflunisal, sulfasalazine, olsalazine, and mesalamine.

In certain instances, a class of non-selective COX inhibitors is indole and indene acetic acids. Certain compounds of this class include, among others, indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac.

In certain instances, a class of non-selective COX inhibitors is heteroaryl acetic acids. Certain compounds of this class include, among others, tolmetin, diclofenac, and ketorolac.

In certain instances, a class of non-selective COX inhibitors is arylpropionic acids or propionic acid derivatives (profens). Certain compounds of this class include among others, alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen.

In certain instances, a class of non-selective COX inhibitors is anthranilic acids (fenamates). Certain compounds of this class include, among others, flufenamic acid, meclofenamic acid, mefenamic acid, niflumic acid and tolfenamic acid.

In certain instances, a class of non-selective COX inhibitors is enolic acids (e.g., oxicams). Certain compounds of this class include, among others, piroxicam and meloxicam, isoxicam, and sudoxicam and tenoxican.

In certain instances, a class of non-selective COX inhibitors is phenylpyrazolones. Certain compounds of this class include, among others, phenylbutazone, apazone, bezpiperylon, feprazone, mofebutazone, oxyphenbutazone.

In certain instances, a class of non-selective COX inhibitors is biphenylcarboxylic acid derivatives. Certain compounds of this class include, among others, diflunisal and flufenisal.

In certain instances, the NSAIDs are selective COX-2 inhibitors. As used herein, a selective COX-2 inhibitor preferably inhibits the activity of COX-2 isozyme as compared to the inhibition of the COX-1 isozyme. A selective COX-2 inhibitor can have a selectivity (i.e., inhibition of COX-2/COX-1) of about 10, of about 20 of about 50, of about 100, of about 200, of about 500, and of about 1000 or more. Selectivity is based on assay typically used to measure COX activity.

In certain instances, a class of selective COX-2 inhibitors is diaryl-substituted furanones. A certain compound of this class includes, among others, refocoxib, available under the tradename Vioxx™.

In certain instances, a class of selective COX-2 inhibitors is diaryl-substituted pyrazoles. A certain compound of this class includes, among others, celecoxib, available under the tradename Celebrex™.

In certain instances, a class of selective COX-2 inhibitors is indole acetic acids. A certain compound of this class includes, among others, etodolac, available under the tradename Lodine™.

In certain instances, a class of selective COX-2 inhibitors is sulfonanilides. A certain compound of this class includes, among others, nimesulide.

Lipoxygenase and 5-Lipoxygenase Activating Protein (FLAP) Antagonists

In certain instances, the non-steroidal anti-inflammatory agent that can be used with the subject compounds is a lipoxygenase or a 5-lipoxygenase activating protein (FLAP) antagonist.

In certain instances, various antagonists of lipoxygenase may be used to ameliorate the inflammatory response mediated by the leukotrienes. Classes of lipoxygenase inhibitors include, among others, N-hydroxyurea derivatives, redox inhibitors, and non-redox inhibitors. Certain N-hydroxyurea derived inhibitors include, by way of example and not limitation, 1-(1-benzothiophen-2-ylethyl)-1-hydroxy-urea (leutrol), 1-[4-[5-(4-fluorophenoxy)-2-furyl]but-3-yn-2-yl]-1-hydroxy-urea; 1-[(2R)-4-[5-[(4-fluorophenyl)methyl] thiophen-2-yl]but-3-yn-2-yl]-1-hydro-xy-urea (atreleuton); 3-(1-benzothiophen-2-ylethyl)-1-hydroxy-urea. A certain redox inhibitor includes, by way of example and not limitation, 2-(12-hydroxydodeca-5,10-diynyl)-3,5,6-trimethyl-cyclohexa-2,5-diene-1,4-dione (docebenone). A certain non-redox inhibitor includes, by way of example and not limitation, 6-[[3-fluoro-5-(4-methoxyoxan-4-yl)phenoxy] methyl]-1-methyl-quinolin-2-one (i.e., ZD2138).

In certain instances, a FLAP antagonist may be used as the anti-inflammatory agent. FLAP antagonists include, among others, indole derivatives and quinoline derivatives. Certain indole derivatives with FLAP inhibitory activity include, by way of example and not limitation, 3-[3-butylsulfanyl-1-[(4-chlorophenyl)methyl]-5-propan-2-yl-indol-2-yl]-2-, 2-dimethyl-propanoic acid (i.e., MK-866) and 3-[1-[(4-chlorophenyl)methyl]-5-(quinolin-2-ylmethoxy)-3-tert-butylsulfanyl-indol-2-yl]-2,2-dimethyl-propanoic acid (i.e., MK0591 or quiflapon). Certain quinoline derivatives include, by way of example and not limitation, (2R)-2-cyclopentyl-2-[4-(quinolin-2-ylmethoxy)phenyl]acetic acid (i.e., BAY-X1005 and veliflapon).

Anti-Histamines

In certain instances, the subject compounds are used in combination with anti-histamines, which are generally H1-receptor antagonists. Certain H1 receptor antagonists include, among others, doxepin, cabinoxamine, clemastine, diphenylhydramine, dimenhydrinate, pyrilamine, tripelennamine, chlorpheniramine, bromopheniramine, hydroxyzine, cyclizine, meclizine, promethazine, cyproheptadine, phenindamine, acrivastine, citirizine, azelastine, levocabastine, loratadine, fexofenadine, and various salts, hydrates, N-oxides, and prodrugs thereof.

Beta-Agonists

In certain instances, the subject compounds are used in combination with β-adrenergic receptor agonists (synonymously "β-agonists" or "β-adrenergic agonists"), which includes non-selective β-adrenergic agonists as well as $β_2$-selective adrenergic agonists. There are generally two types of β-agonists, short-acting β-agonists and long-acting β-adrenergic agonists.

Certain short acting β-adrenergic agonists include, by way of example and not limitation, albuterol (salbutamol), isotharine, fenoterol, levalbuterol, metaproterenol (orciprenaline), procaterol, terbutaline, and pirbuterol. Certain long-acting β-adrenergic agonists include, by way of example and not limitation, salmeterol xinafoate, formoterol, and bitolterol. Certain non-selective β-agonists include, by way of example and not limitation, isoproterenol and dobutamine.

Anti-Metabolite Anti-Inflammatory Agents

In certain instances, the anti-inflammatory agent is an anti-metabolite that attenuates or inhibits the activation and/or proliferation of cells involved in inflammation. Anti-metabolites may have cytostatic or cytotoxic effects and thus generally display immunosuppressive characteristics.

Various anti-inflammatory anti-metabolites may be used in combination with the subject compounds. In certain instances, the anti-proliferative agent is methotrexate.

In certain instances, the anti-proliferative anti-metabolite includes an inhibitor of inosine monophosphate dehydrogenase (IMPDH), the enzyme acting in the salvage pathway for the synthesis of guanosine monophosphate (GMP) from inosine. IMPDH inhibitors useful as anti-inflammatory agents include, among others, mycophenolic acid, mycophenolate mofetil, ribavirin, taizofurin, selenazofurin, benzamide adenine dinucleotide, and benzamide riboside.

Other anti-metabolites include azathioprine, 6-mercaptopurine (6-MP), leflunomide, and malononitriloamides.

Another anti-metabolite is methotrexate (amethopterin or (2S)-2-[(4-{[(2,4-diamino-7,8-dihydropteridin-6-yl)methyl](methyl)amino}phenyl)formamido]pentanedioic acid).

Anti-TNF-Alpha Agents

It is to be understood that anti-inflammatory agents other than those described above may be used in combination with the subject compounds. These include various agents directed against the cellular factors thought to be involved in promoting the inflammatory response. In certain instances, the anti-inflammatory agent is an agent that blocks the action of TNFα, the major cytokine implicated in inflammatory disorders. In certain instances, the anti-TNF is an antibody that blocks the action of TNFα. A certain anti-TNF antibody is infliximab, available under the tradename Remicade™.

In certain instances, the anti-TNFα agent is a receptor construct that binds TNFα and prevents its interaction with TNF receptors on present on cells. A certain anti-inflammatory agent based on TNFα receptor is entanercept, available under the tradename Enbrel™.

Statins

In certain instances, the subject compounds are used in combination with statins. Statins are a class of drugs that can lower cholesterol and act as HMG-CoA reductase inhibitor. Examples of statins include atorvastatin, cerivastatin, fluvastatin, lovastatin, mevastatin, pitastatin, pravastatin, rosuvastatin, and simvastatin. A certain statin is atorvastatin, available under the tradename Lipitor™. Another statin is simvastatin, available under the tradename Zocor™.

Also provided is a method comprising administering a Syk inhibitory 2,4-pyrimidinediamine compound and an anti-hypertensive agent to a patient having an inflammatory disorder, thereby treating the inflammatory disorder. In this method, the anti-hypertensive agent may be selected from the group consisting of: a diuretic, an adrenergic blocker, an angiotensin converting enzyme (ACE) inhibitor, an angiotensin II receptor antagonist, a calcium channel blocker, a direct vasodilator, and a neutral endopeptidase inhibitor. Diuretics cause the reduction of water and sodium, or block sodium transport, resulting in a reduction in blood pressure. Adrenergic blockers include alpha-blockers, beta-blockers and the alpha/beta blocker labetalol, that block the effects of the sympathetic nervous system, which responds to stress by raising blood pressure. Angiotensin converting enzyme (ACE) inhibitors lower blood pressure by dilating arteries by blocking the effects of the angiotensin-renin-aldosterone system. Angiotensin II receptor antagonists lower blood pressure by blocking the angiotensin II receptor. Calcium channel blockers and direct vasodilators reduce blood pressure by causing blood vessel dilation. Neutral endopeptidase inhibitors produce higher levels of atrial natiuretic peptide, which opens blood vessels. Exemplary anti-hypertensive agents are described in U.S. patent application publications US20060160834 and US20070092888 and are discussed in greater detail below.

In one embodiment, the anti-hypertensive agent may be an ACE inhibitor. ACE inhibitors help relax blood vessels by blocking the cyclization of angiotensin as well as degrading bradykinin, which both cause vasoconstriction. There are different classes of ACE inhibitors. Certain examples of non-peptide inhibitors chelate zinc and heavy metal ions needed for enzymatic activity, and thereby create a catalytically defective enzyme. A second class of inhibitors includes peptides and peptidomimetics that interact with ACE similarly to endogenous substrates. Examples of ACE inhibitors include benazepril, captopril, cilazapril, delapril, enalapril, fosinopril, imidapril, losinopril, moexipril, quinapril, quinaprilat, ramipril, perindopril, perindropril, quanipril, spirapril, tenocapril, trandolapril, and zofenopril, and pharmaceutically acceptable salts or esters thereof, suitable dosages for which are known to those of skill in the art.

In another embodiment, the anti-hypertensive agent may be an angiotensin II receptor antagonist. Such agents help relax blood vessels by blocking the angiotensin II receptor (a GPCR), which binds free angiotensin II and initiates the biochemical signal pathways that lead to many downstream physiological effects, including vasoconstruction. Candesartan, eprosartan, irbesartan, losartan (2-butyl-4-chloro-1-[p-(o-1H-tetrazol-5-ylphenyl)benzyl]imidazole-5-methanol), pratosartan, tasosartan, telmisartan, valsartan, and EXP-3137, FI6828K, and RNH6270, and pharmaceutically acceptable salts or esters thereof are examples of angiotension II receptor antagonists.

In another embodiment, the anti-hypertensive agent may be a calcium channel blocker. $Ca^{2+}$ acts as an intracellular messenger. $Ca^{2+}$-binding proteins sense increases in $Ca^{2+}$ concentration and trigger cellular processes such as muscle contraction. A calcium channel blocker may target CaV1 channels, specifically CaV1.2 channels that are highly expressed in cardiac and smooth muscle. The three most commonly employed calcium channel blocker classes are phenylalkylamines (PAA; e.g., verapamil), benzothiazepines (e.g., diltiazem), and dihydropyridines (DHP; e.g., nifedipine or amlodipine). Each drug class binds to distinct sites on the $\alpha_1$ subunit that mediate blocking Examples of calcium channel blockers include amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and pharmaceutically acceptable salts or esters thereof.

In another embodiment, the anti-hypertensive agent is a beta blocker, which agents block sympathetic effects on the heart and are generally effective in reducing cardiac output and in lowering arterial pressure when there is increased cardiac sympathetic nerve activity. In addition, these agents block the adrenergic nerve-mediated release of renin from the renal juxtaglomerular cells. Examples of this group of drugs include, but are not limited to, chemical agents such as acebutolol, atenolol, betaxolol, bevantolol, bisoprolol, bopindolol, carteoiol, carvedilol, celiprolol, esmolol, indenolol, metaprolol, nadolol, nebivolol, penbutolol, pindolol, propanolol, sotalol, tertatolol, tilisolol, and timolol, and pharmaceutically acceptable salts or esters thereof. The nonselective beta-blockers, including propranolol, oxprenolol, pindolol, nadolol, timolol and labetalol, which each antagonize both $\beta_1$- and $\beta_2$-adrenergic receptors. For the selective antagonists, including metoprolol, atenolol, esmolol, and acebutolol, each has much greater binding affinity for the $\beta_1$ adrenergic receptor. The selective beta-blockers are normally indicated for patients in whom $\beta_2$-receptor antagonism might be associated with an increased risk of adverse effects. Such patients include those with asthma or diabetes, or patients with peripheral vascular disease or Raynaud's disease.

In another embodiment, the anti-hypertensive agent is a diuretic, i.e., an agent that affects sodium diuresis and volume depletion in a patent. Diuretic antihypertensives include thiazides (such as hydrochlorothiazide, chlorothiazide, and chlorthalidone), metolazone, loop diuretics (such as furosemide, bumetanide, ethacrynic acid, piretanide and torsemide), and aldosterone antagonists (such as spironolactone, triamterene, and amiloride).

Other anti-hypertensive agents include renin inhibitors (e.g., aliskiren and tekturna, which slow down the production of renin), alpha-blockers (e.g, alpha 2a agonists such as lofexidine, tiamenidine, moxonidine, rilmenidine and guanobenz and alpha 1 blockers such as terazosin, urapidil, prazosin, bunazosin, trimazosin, doxazosin, naftopidil, indoramin, WHIP 164, and XEN010, and pharmaceutically acceptable salts or esters thereof), alpha-beta blockers (e.g., nipradilol, arotinolol and amosulalol, and pharmaceutically acceptable salts or esters thereof), central-acting agents (which prevent the brain from signaling the nervous system to increase heart rate and narrow blood vessels), vasodilators, e.g., hydralazine (apresoline), clonidine (catapres), minoxidil (loniten), and nicotinyl alcohol (roniacol); and pharmaceutically acceptable salts or esters thereof) and endothelin antagonists (e.g., tezosentan, A308165, and YM62899, and pharmaceutically acceptable salts or esters thereof).

Pharmaceutical Compositions

In another aspect, the present disclosure provides compositions comprising one or more compounds or salts as described above with respect to any of formulae (I)-(XV) and an appropriate carrier, excipient or diluent. The exact nature of the carrier, excipient or diluent will depend upon the desired use for the composition, and may range from being suitable or acceptable for veterinary uses to being suitable or acceptable for human use. The composition may optionally include one or more additional compounds.

When used to treat or prevent such diseases, the compounds described herein may be administered singly, as mixtures of one or more compounds or in mixture or combination with other agents useful for treating such diseases and/or the symptoms associated with such diseases. The compounds may also be administered in mixture or in combination with agents useful to treat other disorders or maladies, such as steroids, membrane stabilizers, 5LO inhibitors, leukotriene synthesis and receptor inhibitors, inhibitors of IgE isotype switching or IgE synthesis, IgG isotype switching or IgG synthesis, $\beta$-agonists, tryptase inhibitors, aspirin, COX inhibitors, methotrexate, anti-TNF drugs, retuxin, PD4 inhibitors, p38 inhibitors, PDE4 inhibitors, and antihistamines, to name a few. The compounds may be administered in the form of compounds per se, or as pharmaceutical compositions comprising a compound.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known.

For buccal administration, the compositions may take the form of tablets or lozenges formulated in conventional manner.

For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethylsulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. The compound(s) may be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack, or a reduction in the frequency or severity of asthmatic episodes. Therapeutic benefit in the context of rheumatoid arthritis also includes the ACR20, or ACR50 or ACR70, as previously described. Therapeutic benefit also generally includes halting or slowing the progression of the disease, regardless of whether improvement is realized.

For prophylactic administration, the compound(s) may be administered to a patient at risk of developing one of the previously described diseases. For example, if it is unknown whether a patient is allergic to a particular drug, the compound(s) may be administered prior to administration of the drug to avoid or ameliorate an allergic response to the drug. Alternatively, prophylactic administration may be applied to avoid the onset of symptoms in a patient diagnosed with the underlying disorder. For example, the compound(s) may be administered to an allergy sufferer prior to expected exposure to the allergen. Compound(s) may also be administered prophylactically to healthy individuals who are repeatedly exposed to agents known to one of the above-described maladies to prevent the onset of the disorder. For example, compound(s) may be administered to a healthy individual who is repeatedly exposed to an allergen known to induce allergies, such as latex, in an effort to prevent the individual from developing an allergy. Alternatively, compound(s) may be administered to a patient suffering from asthma prior to partaking in activities which trigger asthma attacks to lessen the severity of, or avoid altogether, an asthmatic episode.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an $IC_{50}$ of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active metabolite compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective local dosages without undue experimentation.

DEFINITIONS

As used herein, the following terms are intended to have the following meanings:

"Alkyl" includes those alkyl groups containing from 1 to 10, preferably 1 to 6, carbon atoms. Alkyl groups may be straight, or branched. Examples of "alkyl" include methyl, ethyl, n-propyl, iso-propyl, n-butyl, iso-, sec- and tert-butyl, n-pentyl, iso-penyl, neopentyl, n-hexyl, 3-methylhexyl, 2,2-dimethylpentyl, 2,3-dimethylpentyl, n-heptyl, 3-ethylbutyl, n-octyl, n-nonyl, n-decyl and the like. Alkyl groups described without specifying branching encompass all possible isomers. For example, "propyl" includes n-propyl and iso-propyl, and "butyl" includes n-butyl, iso-butyl, sec-butyl and tert-butyl.

The term "alkenyl" as used herein, means a straight or branched chain hydrocarbon containing from 2 to 10, preferably 2 to 6, carbons, and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl" as used herein, means a straight or branched chain hydrocarbon group containing from 2 to 10, preferably 2 to 6, carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "aryl" refers to an aromatic hydrocarbon ring system containing at least one aromatic ring. The aromatic ring may optionally be fused or otherwise attached to other aromatic hydrocarbon rings or non-aromatic hydrocarbon rings. Representative examples of aryl groups include phenyl, naphthyl, anthracenyl 1,2,3,4-tetrahydronaphthalene, indenyl, 2,3-dihydroindenyl, and biphenyl. Preferred examples of aryl groups are phenyl and naphthyl. Most preferred is phenyl.

The term "arylene" as used herein refers to a bivalent aromatic hydrocarbon ring system containing at least one aromatic ring. The aromatic ring may optionally be fused or otherwise attached to other aromatic hydrocarbon rings or non-aromatic hydrocarbon rings. Representative examples of arylene groups include 1,2-, 1,3- and 1,4-phenylene.

The term "aryloxy" as used herein, means an aryl group, as defined herein, appended to the parent molecular moiety through an oxygen atom.

The term "cycloalkyl" as used herein means, means a monocyclic, bicyclic, or tricyclic ring system having only carbon atoms in the rings. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The terms "halogen" or "halo" indicate fluorine, chlorine, bromine, and iodine.

The term "haloalkyl" refers to an alkyl group substituted with one or more halogen atoms, where each halogen is independently F, Cl, Br or I. Representative examples of haloalkyl include, but are not limited to, chloromethyl, 2-fluoroethyl, trifluoromethyl, pentafluoroethyl, and 2-chloro-3-fluoropentyl. "Haloalkyl" includes perhaloalkyl groups, such as —$CF_3$ or —$CF_2CF_3$. Preferred halogens are F and Cl. Preferred haloalkyl groups contain 1-6 carbons, more preferably 1-4 carbons, and still more preferably 1-2 carbons. A preferred haloalkyl group is trifluoromethyl. "Halo($C_1$-$C_6$ alkyl)" denotes a haloalkyl having in the range of from 1 to 6 carbons.

The term "haloalkoxy" refers to an alkoxy group substituted with one or more halogen atoms, where each halogen is independently F, Cl, Br or I. Representative examples of haloalkoxy include, but are not limited to, chloromethoxy, 2-fluoroethoxy, trifluoromethoxy, and pentafluoroethoxy. "Haloalkoxy" includes perhaloalkoxy groups, such as $CF_3$. Preferred halogens are F and Cl. Preferred haloalkoxy groups contain 1-6 carbons, more preferably 1-4 carbons, and still more preferably 1-2 carbons. A preferred haloalkoxy group is trifluoromethoxy. "Halo($C_1$-$C_6$ alkoxy)" denotes a haloalkoxy having in the range of from 1 to 6 carbons.

The term "heteroaryl" as used herein, means a monocyclic or a bicyclic ring system containing at least one aromatic ring, where the aromatic ring contains at least one heteroatom selected from nitrogen, oxygen, and sulfur. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to an aryl (e.g., phenyl), or a monocyclic heteroaryl fused to a cycloalkyl, or a monocyclic heteroaryl fused to a cycloalkenyl, or a monocyclic heteroaryl fused to a monocyclic heteroaryl, or a monocyclic heteroaryl fused to a monocyclic heterocyclyl. The bicyclic heteroaryl is connected to the parent molecular moiety through any carbon atom or any nitrogen atom contained within the bicyclic heteroaryl. Representative examples of bicyclic heteroaryl include, but are not limited to, benzimidazolyl, benzofuranyl, benzothienyl, benzoxadiazolyl, cinnolinyl, dihydroquinolinyl, dihydroisoquinolinyl, furopyridinyl, purinyl, indazolyl, indolyl, isoquinolinyl, naphthyridinyl, quinolinyl, tetrahydroquinolinyl, and thienopyridinyl.

The term "heteroarylene" as used herein refers to a bivalent monocyclic or a bicyclic ring system containing at least one aromatic ring, where the aromatic ring contains at least one heteroatom selected from nitrogen, oxygen, and sulfur. Representative examples of heteroarylene include pyridylene, pyrazylene, pyrimidylene, and pyridazylene.

The term "heterocycloalkyl" as used herein, refers to a ring or ring system containing at least one heteroatom selected from nitrogen, oxygen, and sulfur, wherein said heteroatom is in a non-aromatic ring and the ring system is attached to the parent group by a member of (one of) the non-aromatic ring(s). The heterocycloalkyl ring is optionally fused to other heterocycloalkyl rings and/or non-aromatic hydrocarbon rings, and/or phenyl rings. Thus, heterocycloalkyl groups suitable for the invention have at least 3 members, and may have up to 20 members. Preferred heterocycloalkyl groups have from 3 to 10 members. Certain more preferred heterocycloalkyl groups have from 8-10 members. Other more preferred heterocycloalkyl groups have 5 or 6 members. Representative examples of heterocycloalkyl groups include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, trithianyl, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl, 2,3,4,4a,9,9a-hexahydro-1H-carbazolyl, 5a,6,7,8,9,9a-hexahydrobenzo[b,d]furanyl, and 5a,6,7,8,9,9a-hexahydrobenzo[b,d]thienyl.

The term "oxo" as used herein means a =O group. Multivalent atoms, such as sulfur, may contain more than one oxo group.

The term "isotopic enrichment factor" as used herein means the ratio between the isotopic abundance and the natural abundance of a specified isotope. It will be recognized that some variation of natural isotopic abundance occurs in a synthesized compound depending upon the origin of chemical materials used in the synthesis. Thus, a preparation of any compound will inherently contain small amounts of deuterated isotopologues. The concentration of naturally abundant stable hydrogen isotopes, notwithstanding this variation, is small and immaterial as compared to the degree of stable isotopic substitution of compounds of this disclosure. In a compound of this disclosure, when a particular position is designated as having deuterium, it is understood that the abundance of deuterium at that position is substantially greater than the natural abundance of deuterium, which is about 0.015% (on a mol/mol basis). A position designated as having deuterium will often have a minimum isotopic enrichment factor of at least 3000 (45% deuterium incorporation) at each atom designated as deuterium in the compound.

In the compounds of this disclosure any atom not specifically designated as a particular isotope is meant to represent any stable isotope of that atom. Unless otherwise stated, when a position is designated specifically as "H" or "hydrogen", the position is understood to have hydrogen at about its natural abundance isotopic composition.

The term "isotopologue" refers to a species that has the same chemical structure and formula as a specific compound of this disclosure, with the exception of the isotopic composition at one or more positions, e.g., H vs. D. Thus an isotopologue differs from a specific compound of this disclosure in the isotopic composition thereof.

"Fc Receptor" refers to a member of the family of cell surface molecules that binds the Fc portion (containing the specific constant region) of an immunoglobulin. Each Fc receptor binds immunoglobulins of a specific type. For example the Fcα receptor ("FcαR") binds IgA, the FcεR binds IgE and the FcγR binds IgG.

The FcαR family includes the polymeric Ig receptor involved in epithelial transport of IgA/IgM, the myeloid specific receptor RcαRI (also called CD89), the Fcα/μR and at least two alternative IgA receptors (for a recent review see Monteiro & van de Winkel, 2003, Annu Rev. Immunol, advanced e-publication). The FcαRI is expressed on neutrophils, eosinophils, monocytes/macrophages, dendritic cells and kupfer cells. The FcαRI includes one alpha chain and the FcR gamma homodimer that bears an activation motif (ITAM) in the cytoplasmic domain and phosphorylates Syk kinase.

The FcεR family includes two types, designated FcεRI and FcεRII (also known as CD23). FcεRI is a high affinity receptor (binds IgE with an affinity of about $10^{10}$ $M^{-1}$) found on mast, basophil and eosinophil cells that anchors monomeric IgE to the cell surface. The FcεRI possesses one alpha chain, one beta chain and the gamma chain homodimer discussed above. The FcεRII is a low affinity receptor expressed on mononuclear phagocytes, B lymphocytes, eosinophils and platelets. The FcεRII comprises a single polypeptide chain and does not include the gamma chain homodimer.

The FcγR family includes three types, designated FcγRI (also known as CD64), FcγRII (also known as CD32) and FcγRIII (also known as CD 16). FcγRI is a high affinity receptor (binds IgG1 with an affinity of $10^8$ $M^{-1}$) found on mast, basophil, mononuclear, neutrophil, eosinophil, dendritic and phagocyte cells that anchors nomomeric IgG to the cell surface. The FcγRI includes one alpha chain and the gamma chain dimer shared by FcαRI and FcεRI.

The FcγRII is a low affinity receptor expressed on neutrophils, monocytes, eosinophils, platelets and B lymphocytes. The FcγRII includes one alpha chain, and does not include the gamma chain homodimer discussed above.

The FcγRIII is a low affinity (binds IgG1 with an affinity of $5 \times 10^5$ M$^{-1}$) expressed on NK, eosinophil, macrophage, neutrophil and mast cells. It comprises one alpha chain and the gamma homodimer shared by FcαRI, FcεRI and FcγRI.

Skilled artisans will recognize that the subunit structure and binding properties of these various Fc receptors, as well as the cell types expressing them, are not completely characterized. The above discussion merely reflects the current state-of-the-art regarding these receptors (see, e.g., Immunobiology: The Immune System in Health & Disease, 5$^{th}$ Edition, Janeway et al., Eds, 2001, ISBN 0-8153-3642-x, FIG. 9.30 at pp. 371), and is not intended to be limiting with respect to the myriad receptor signaling cascades that can be regulated with the compounds described herein.

"Fc Receptor-Mediated Degranulation" or "Fc Receptor-Induced Degranulation" refers to degranulation that proceeds via an Fc receptor signal transduction cascade initiated by crosslinking of an Fc receptor.

"IgE-Induced Degranulation" or "FcεRI-Mediated Degranulation" refers to degranulation that proceeds via the IgE receptor signal transduction cascade initiated by crosslinking of FcεR1-bound IgE. The crosslinking may be induced by an IgE-specific allergen or other multivalent binding agent, such as an anti-IgE antibody. In mast and/or basophil cells, the FcεRI signaling cascade leading to degranulation may be broken into two stages: upstream and downstream. The upstream stage includes all of the processes that occur prior to calcium ion mobilization. The downstream stage includes calcium ion mobilization and all processes downstream thereof. Compounds that inhibit FcεRI-mediated degranulation may act at any point along the FcεRI-mediated signal transduction cascade. Compounds that selectively inhibit upstream FcεRI-mediated degranulation act to inhibit that portion of the FcεRI signaling cascade upstream of the point at which calcium ion mobilization is induced. In cell-based assays, compounds that selectively inhibit upstream FcεRI-mediated degranulation inhibit degranulation of cells such as mast or basophil cells that are activated or stimulated with an IgE-specific allergen or binding agent (such as an anti-IgE antibody) but do not appreciably inhibit degranulation of cells that are activated or stimulated with degranulating agents that bypass the FcεRI signaling pathway, such as, for example the calcium ionophores ionomycin and A23187.

"IgG-Induced Degranulation" or "FcγRI-Mediated Degranulation" refers to degranulation that proceeds via the FcγRI signal transduction cascade initiated by crosslinking of FcγRI-bound IgG. The crosslinking may be induced by an IgG-specific allergen or another multivalent binding agent, such as an anti-IgG or fragment antibody. Like the FcεRI signaling cascade, in mast and basophil cells the FcγRI signaling cascade also leads to degranulation which may be broken into the same two stages: upstream and downstream. Similar to FcεRI-mediated degranulation, compounds that selectively inhibit upstream FcγRI-mediated degranulation act upstream of the point at which calcium ion mobilization is induced. In cell-based assays, compounds that selectively inhibit upstream FcγRI-mediated degranulation inhibit degranulation of cells such as mast or basophil cells that are activated or stimulated with an IgG-specific allergen or binding agent (such as an anti-IgG antibody or fragment) but do not appreciably inhibit degranulation of cells that are activated or stimulated with degranulating agents that bypass the FcγRI signaling pathway, such as, for example the calcium ionophores ionomycin and A23187.

"Ionophore-Induced Degranulation" or "Ionophore-Mediated Degranulation" refers to degranulation of a cell, such as a mast or basophil cell, that occurs upon exposure to a calcium ionophore such as, for example, ionomycin or A23187.

"Syk Kinase" refers to the well-known 72 kDa non-receptor (cytoplasmic) spleen protein tyrosine kinase expressed in B-cells and other hematopoetic cells. Syk kinase includes two consensus Src-homology 2 (SH2) domains in tandem that bind to phosphorylated immunoreceptor tyrosine-based activation motifs ("ITAMs"), a "linker" domain and a catalytic domain (for a review of the structure and function of Syk kinase see Sada et al., 2001, J. Biochem. (Tokyo) 130:177-186); see also Turner et al., 2000, Immunology Today 21:148-154). Syk kinase has been extensively studied as an effector of B-cell receptor (BCR) signaling (Turner et al., 2000, supra). Syk kinase is also critical for tyrosine phosphorylation of multiple proteins which regulate important pathways leading from immunoreceptors, such as Ca$^{2+}$ mobilization and mitogen-activated protein kinase (MAPK) cascades and degranulation. Syk kinase also plays a critical role in integrin signaling in neutrophils (see, e.g., Mocsai et al. 2002, Immunity 16:547-558).

As used herein, Syk kinase includes kinases from any species of animal, including but not limited to, homosapiens, simian, bovine, porcine, rodent, etc., recognized as belonging to the Syk family. Specifically included are isoforms, splice variants, allelic variants, mutants, both naturally occurring and man-made. The amino acid sequences of such Syk kinases are well known and available from GENBANK. Specific examples of mRNAs encoding different isoforms of human Syk kinase can be found at GENBANK accession no. gi|21361552|ref|NM_003177.2|, gi|496899|emb|Z29630.1|HSSYKPTK[496899] and gi|15030258|gb|BC011399.1|BC011399[15030258], which are incorporated herein by reference.

Skilled artisans will appreciate that tyrosine kinases belonging to other families may have active sites or binding pockets that are similar in three-dimensional structure to that of Syk. As a consequence of this structural similarity, such kinases, referred to herein as "Syk mimics," are expected to catalyze phosphorylation of substrates phosphorylated by Syk. Thus, it will be appreciated that such Syk mimics, signal transduction cascades in which such Syk mimics play a role, and biological responses effected by such Syk mimics and Syk mimic-dependent signaling cascades may be regulated, and in particular inhibited, with many of the compounds described herein.

"Syk-Dependent Signaling Cascade" refers to a signal transduction cascade in which Syk kinase plays a role. Non-limiting examples of such Syk-dependent signaling cascades include the FcαRI, FcεRI, FcγRI, FcγRIII, BCR and integrin signaling cascades.

"Autoimmune Disease" refers to those diseases which are commonly associated with the nonanaphylactic hypersensitivity reactions (Type II, Type III and/or Type IV hypersensitivity reactions) that generally result as a consequence of the subject's own humoral and/or cell-mediated immune response to one or more immunogenic substances of endogenous and/or exogenous origin. Such autoimmune diseases are distinguished from diseases associated with the anaphylactic (Type I or IgE-mediated) hypersensitivity reactions.

Methods of Synthesis

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4.sup.th edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

Those of skill in the art of organic synthesis will find examples suitable for synthesizing the present compounds in U.S. Pat. Nos. 7,122,542, 7,449,458, 7,517,886 and 7,557,210, and in international patent application no. PCT/US03/03022 filed Jan. 31, 2003 (WO 03/063794), international patent application no. PCT/US07/85313 filed Nov. 20, 2007 (WO 2008/064274), and international patent application no. PCT/US06/01945 filed Jan. 19, 2006 (WO 2006/078846). Each of these patents and publications is hereby incorporated herein by reference in its entirety. One example of a synthesis is provided in Example

EXAMPLES

The compounds of the disclosure are illustrated further by the following examples, which are provided for illustrative purposes and are not intended to be construed as limiting the disclosure in scope or spirit to the specific compounds described in them.

Example 1

N4-(2,2-dimethyl-3,4-dihydro-3-oxo-2H-pyrido[3,2-b][1,4]oxazin-6-yl)-5-fluoro-N2-(4-morpholinophenyl)-2,4-pyrimidinediamine (Compound 1)

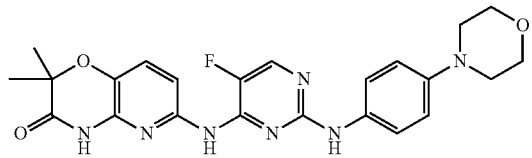 [SMILES: CC1(C)Oc2ccc(Nc3nc(Nc4ccc(N5CCOCC5)cc4)ncc3F)nc2NC1=O]

$^1$H NMR (DMSO-d$_6$): δ 1.43 (s, 6H), 2.99 (t, J=4.8 Hz, 4H), 3.72 (t, J=4.8 Hz, 4H), 6.80 (d, J=8.7 Hz, 2H), 7.36 (d, J=8.4 Hz, 1H), 7.46 (d, J=9.0 Hz, 2H), 7.55 (d, J=8.7 Hz, 1H), 8.06 (d, J=3.6 Hz, 1H), 9.00 (s, 1H), 9.13 (s, 1H), 11.09 (s, 1H); $^{19}$F NMR (282 MHz, DMSO-d$_6$): 6-173.16; LCMS: ret. time: 9.59 min.; purity: 100%; MS (m/e): 466.28 (MH$^+$).

Example 2

N4-(2,2-dimethyl-3,4-dihydro-4-[(dihydrogen phosphonoxy)methyl]-3-oxo-2H-pyrido[3,2-b][1,4]oxazin-6-yl)-5-fluoro-N2-(4-morpholinophenyl)-2,4-pyrimidinediamine (Compound 2)

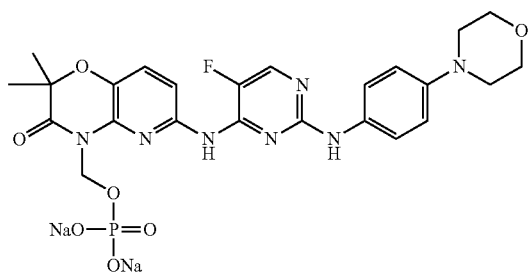

$^1$H NMR (D$_2$O): d 7.60 (d, 1H, J=4.1 Hz), 7.38 (d, 1H, J=8.8 Hz), 6.99 (d, 2H, J=9.1 Hz), 6.78 (d, 1H, J=8.8 Hz, 1H), 6.66 (d, 2H, J=9.1 Hz), 5.45 (d, 2H, J=2.3 Hz), 3.71 (app s, 4H), 2.87 (app s, 4H), 1.29 (s, 6H). LCMS: purity: 99%; MS (m/e): 576 (MH+−2Na+2H).

Example 3

N4-(2,2-dimethyl-3,4-dihydro-3-oxo-2H-pyrido[3,2-b][1,4]oxazin-6-yl)-5-fluoro-N2-[6-morpholinopyridin-3-yl]-2,4-pyrimidinediamine (Compound 3)

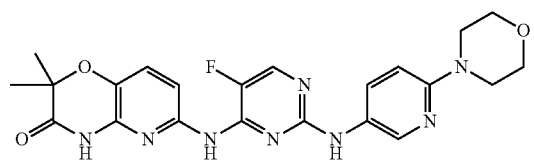 [SMILES: CC1(C)Oc2ccc(Nc3nc(Nc4ccc(N5CCOCC5)nc4)ncc3F)nc2NC1=O]

$^1$H NMR (DMSO-d$_6$): 8.43 (d, 1H, J=2.0 Hz), 8.15 (d, 1H, J=3.5 Hz), 8.06 (d, 1H, J=9.1 Hz), 7.44 (m, 2H), 7.14 (m, 1H), 3.71 (m, 4H), 3.48 (m, 4H), 1.41 (s, 6H); LCMS: purity: 99%; MS (m/e): 467 (MH$^+$).

Example 4

N4-(2,2-dimethyl-3,4-dihydro-4-[(dihydrogen phosphonoxy)methyl]-3-oxo-2H-pyrido[3,2-b][1,4]oxazin-6-yl)-5-fluoro-N2-(6-morpholinopyridin-3-yl)-2,4-pyrimidinediamine disodium salt (Compound 4)

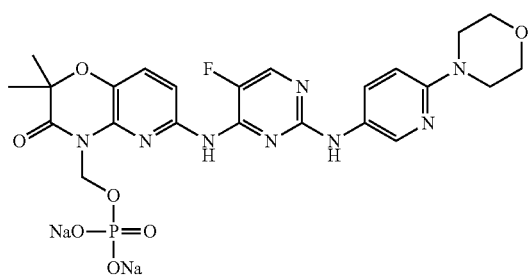

¹H NMR (D₂O): d 7.71 (d, 1H, 2.3 Hz), 7.52 (d, 1H, J=4.1 Hz), 7.27 (dd, 1H, J=2.3 and 9.1 Hz), 7.17 (d, 1H, J=8.8 Hz), 6.67 (d, 1H, J=8.8 Hz), 6.33 (d, 1H, J=9.1 Hz), 5.43 (d, 1H, J=2.3 Hz), 3.64 (s, 4H), 3.02 (s, 4H), 1.25 (s, 6H); LCMS: purity: 99%; MS (m/e): 577 (MH⁺−2Na+2H).

Example 5

N4-(3,4-dihydro-3-oxo-2H-pyrido[3,2-b][1,4]oxazin-6-yl)-5-fluoro-N2-[6-morpholinopyridin-3-yl]-2,4-pyrimidinediamine (Compound 5)

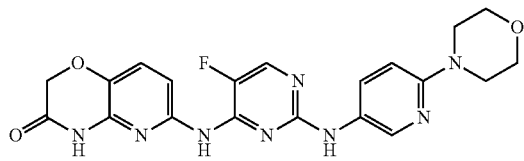 [SMILES: O=C1COc2ccc(Nc3nc(Nc4ccc(N5CCOCC5)nc4)ncc3F)nc2N1]

¹H NMR (DMSO-d₆): 8.46 (d, 1H, J=2.0 Hz), 8.15 (d, 1H, J=3.5 Hz), 8.06 (d, 1H, J=9.1 Hz), 7.44 (m, 2H), 7.14 (m, 1H), 4.63 (s, 2H), 3.71 (m, 4H), 3.48 (m, 4H); LCMS: purity: 99%; MS (m/e): 439 (MH⁺)

Example 6

N4-(3,4-dihydro-3-oxo-2H-pyrido[3,2-b][1,4]oxazin-6-yl)-5-fluoro-N2-[6-((2R)-2-methylmorpholino)pyridin-3-yl]-2,4-pyrimidinediamine (Compound 6)

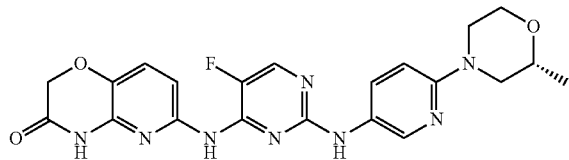 [SMILES: C[C@@H]1CN(c2ccc(Nc3ncc(F)c(Nc4ccc5c(n4)NC(=O)CO5)n3)cn2)CCO1]

¹H NMR (DMSO-d₆): 1H NMR (DMSO-d6): 8.46 (d, 1H, J=2.0 Hz), 8.11 (d, 1H, J=3.8 Hz), 7.94 (d, 1H, J=8.8 Hz), 7.44 (d, 1H, J=8.8 Hz), 7.35 (d, 1H, J=8.5 Hz), 6.96 (d, 1H, J=8.5 Hz), 4.62 (s, 2H), 4.01 (d, 1H, J=11.5 Hz), 3.89 (d, 2H, J=11.5 Hz), 3.58-3.31 (m, 2H), 2.86-2.78 (m, 1H), 2.39 (t, 1H, J=11.2 Hz), 1.13 (d, 3H, J=6.3 Hz); LCMS: purity: 99%; MS (m/e): 453 (MH⁺)

Example 7

N4-(2,2-dimethyl-3,4-dihydro-3-oxo-2H-pyrido[3,2-b][1,4]oxazin-6-yl)-5-fluoro-N2-1-2,4-pyrimidinediamine (Compound 7)

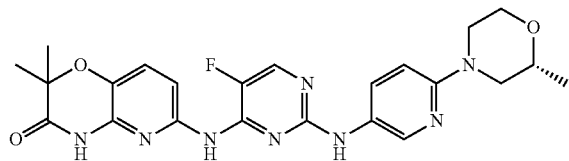 [SMILES: C[C@@H]1CN(c2ccc(Nc3ncc(F)c(Nc4ccc5c(n4)NC(=O)C(C)(C)O5)n3)cn2)CCO1]

¹H NMR (DMSO-d₆): 8.43 (d, 1H, J=2.0 Hz), 8.07 (d, 1H, J=3.5 Hz), 7.85 (d, 1H, J=9.1 Hz), 7.44 (d, 1H, J=8.5 Hz), 7.34 (d, 1H, J=8.5 Hz), 6.74 (d, 1H, J=9.1 Hz), 3.98 (d, 1H, J=11.2 Hz), 3.88 (d, 2H, J=11.2 Hz), 3.54 (app t, 2H), 2.71-2.64 (m, 1H), 2.35 (t, 1H, J=11.2 Hz), 1.41 (s, 6H), 1.14 (d, 3H, J=6.3 Hz); LCMS: purity: 99%; MS (m/e): 481 (MH⁺)

Example 8

N4-(2,2-dimethyl-3,4-dihydro-3-oxo-2H-pyrido[3,2-b][1,4]oxazin-6-yl)-5-fluoro-N2-[6-(2,2-dimethylmorpholino)pyridin-3-yl]-2,4-pyrimidinediamine (Compound 8)

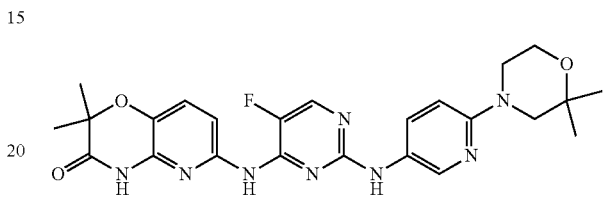

¹H NMR (DMSO-d₆): 8.37 (d, 1H, J=2.0 Hz), 8.05 (d, 1H, J=3.5 Hz), 7.82 (d, 1H, J=9.1 Hz), 7.44 (d, 1H, J=8.5 Hz), 7.34 (d, 1H, J=8.5 Hz), 6.72 (d, 1H, J=9.1 Hz), 3.71 (m, 2H), 3.30 (m, 4H), 1.41 (s, 6H), 1.14 (s, 6H); LCMS: purity: 99%; MS (m/e): 495 (MH⁺)

Example 9

N4-(3,4-dihydro-3-oxo-2H-pyrido[3,2-b][1,4]oxazin-6-yl)-5-fluoro-N2-[6-(2,2-dimethylmorpholino)pyridin-3-yl]-2,4-pyrimidinediamine (Compound 9)

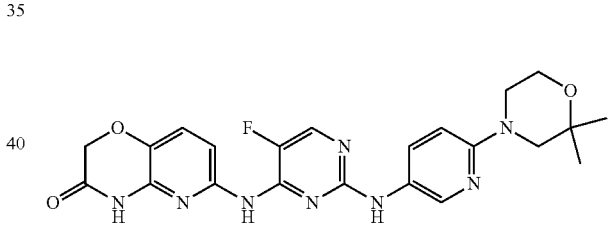

¹H NMR (DMSO-d₆): 8.37 (d, 1H, J=2.0 Hz), 8.05 (d, 1H, J=3.5 Hz), 7.82 (d, 1H, J=9.1 Hz), 7.44 (d, 1H, J=8.5 Hz), 7.34 (d, 1H, J=8.5 Hz), 6.72 (d, 1H, J=9.1 Hz), 4.62 (s, 2H), 3.71 (m, 2H), 3.30 (m, 4H), 1.17 (s, 6H); LCMS: purity: 99%; MS (m/e): 467 (MH⁺)

Example 10

N4-(2,2-dimethyl-3,4-dihydro-3-oxo-2H-pyrido[3,2-b][1,4]oxazin-6-yl)-5-fluoro-N2-[5-fluoro-6-morpholinopyridin-3-yl]-2,4-pyrimidinediamine (Compound 10)

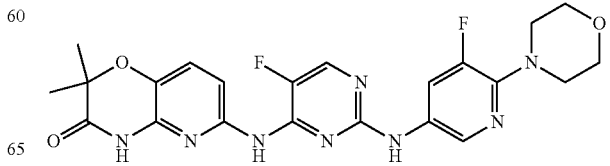

¹H NMR (DMSO-d₆): 8.22 (s, 1H), 8.11 (d, 1H, J=2.0 Hz), 8.00 (d, 1H, J=15 Hz), 7.36 (m, 2H), 3.68 (m, 4H), 3.17 (m, 4H), 1.41 (s, 6H); LCMS: purity: 99%; MS (m/e): 485 (MH⁺)

Example 11

N4-(3,4-dihydro-3-oxo-2H-pyrido[3,2-b][1,4]oxazin-6-yl)-5-fluoro-N2-[5-methyl-6-morpholinopyridin-3-yl]-2,4-pyrimidinediamine (Compound 11)

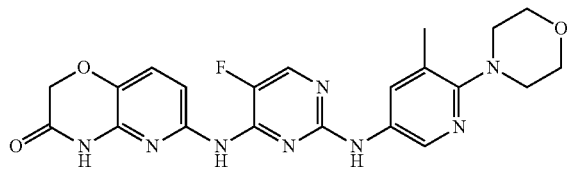 [SMILES: Cc1cc(Nc2ncc(F)c(Nc3ccc4c(n3)NC(=O)CO4)n2)cnc1N1CCOCC1]

¹H NMR (DMSO-d₆): 8.44 (s, 1H), 8.17 (d, 1H, J=2.0 Hz), 7.95 (s, 1H), 7.37 (m, 2H), 4.63 (s, 2H), 3.71 (m, 4H), 3.07 (m, 4H), 2.21 (s, 3H); LCMS: purity: 99%; MS (m/e): 453 (MH⁺)

Example 12

N4-(3,4-dihydro-3-oxo-2H-pyrido[3,2-b][1,4]oxazin-6-yl)-5-fluoro-N2-[5-methyl-6-(2,2-dimethylmorpholino)pyridin-3-yl]-2,4-pyrimidinediamine (Compound 12)

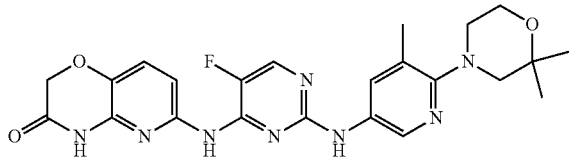 [SMILES: Cc1cc(Nc2ncc(F)c(Nc3ccc4c(n3)NC(=O)CO4)n2)cnc1N1CCOC(C)(C)C1]

¹H NMR (DMSO-d₆): 8.45 (s, 1H), 8.37 (d, 1H, J=2.0 Hz), 7.96 (s, 1H), 7.38 (m, 2H), 4.63 (s, 2H), 3.75 (m, 2H), 3.01 (m, 2H), 2.86 (m, 2H), 2.24 (s, 3H), 1.23 (s, 6H); LCMS: purity: 99%; MS (m/e): 481 (MH⁺)

Example 13

N4-(2,2-dimethyl-3,4-dihydro-3-oxo-2H-pyrido[3,2-b][1,4]oxazin-6-yl)-5-fluoro-N2-[5-methyl-6-morpholinopyridin-3-yl]-2,4-pyrimidinediamine (Compound 13)

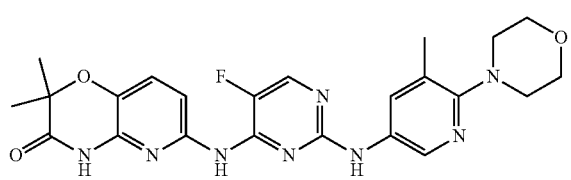 [SMILES: Cc1cc(Nc2ncc(F)c(Nc3ccc4c(n3)NC(=O)C(C)(C)O4)n2)cnc1N1CCOCC1]

¹H NMR (DMSO-d₆): 8.36 (s, 1H), 8.17 (d, 1H, J=2.0 Hz), 7.95 (s, 1H), 7.37 (m, 2H), 3.69 (m, 4H), 2.92 (m, 4H), 2.15 (s, 3H), 1.41 (s, 6H); LCMS: purity: 99%; MS (m/e): 481 (MH⁺)

Example 14

N4-(2,2-dimethyl-3,4-dihydro-3-oxo-2H-pyrido[3,2-b][1,4]oxazin-6-yl)-5-fluoro-N2-[5-methyl-6-(2,2-dimethylmorpholino)pyridin-3-yl]-2,4-pyrimidinediamine (Compound 14)

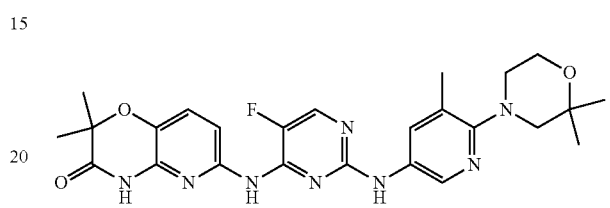

¹H NMR (DMSO-d₆): 8.35 (s, 1H), 8.09 (d, 1H, J=2.0 Hz), 7.82 (s, 1H), 7.48 (m, 1H), 7.35 (m, 1H), 3.73 (m, 2H), 2.87 (m, 2H), 2.70 (m, 2H), 2.17 (s, 3H), 1.41 (s, 6H), 1.23 (s, 6H); LCMS: purity: 99%; MS (m/e): 508 (MH⁺)

Example 15

N4-(2,2-dimethyl-3,4-dihydro-3-oxo-2H-pyrido[3,2-b][1,4]oxazin-6-yl)-5-fluoro-N2-[5-fluoro-6-(2,2-dimethylmorpholino)pyridin-3-yl]-2,4-pyrimidinediamine (Compound 15)

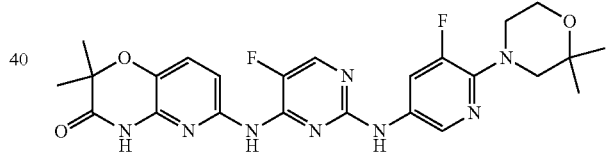

¹H NMR (DMSO-d₆): 8.21 (s, 1H), 8.11 (d, 1H, J=2.0 Hz), 8.01 (d, 1H, J=15 Hz), 7.36 (m, 2H), 3.70 (m, 2H), 3.11 (m, 2H), 2.97 (m, 2H), 1.41 (s, 6H), 1.23 (s, 6H); LCMS: purity: 99%; MS (m/e): 513 (MH⁺)

Example 16

N4-(3,4-dihydro-3-oxo-2H-pyrido[3,2-b][1,4]oxazin-6-yl)-5-fluoro-N2-[5-fluoro-6-morpholinopyridin-3-yl]-2,4-pyrimidinediamine (Compound 16)

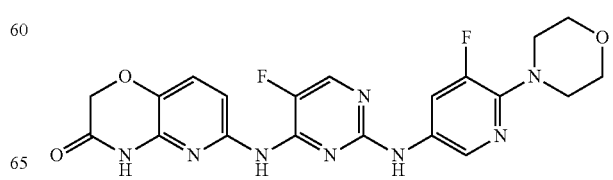

¹H NMR (DMSO-d₆): 8.24 (s, 1H), 8.11 (d, 1H, J=2.0 Hz), 8.00 (d, 1H, J=15 Hz), 7.36 (m, 2H), 4.61 (s, 2H), 3.70 (m, 4H), 3.19 (m, 4H); LCMS: purity: 99%; MS (m/e): 457 (MH⁺)

Example 17

N4-(3,4-dihydro-3-oxo-2H-pyrido[3,2-b][1,4]oxazin-6-yl)-5-fluoro-N2-[5-fluoro-6-(2,2-dimethylmorpholino)pyridin-3-yl]-2,4-pyrimidinediamine (Compound 17)

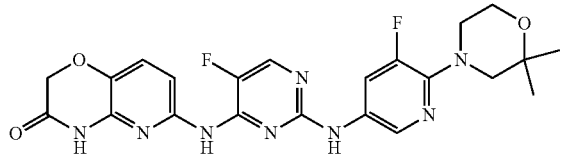 [SMILES: CC1(C)CN(c2ncc(Nc3ncc(F)c(Nc4ccc5c(n4)NC(=O)CO5)n3)cc2F)CCO1]

¹H NMR (DMSO-d₆): 8.21 (s, 1H), 8.11 (d, 1H, J=2.0 Hz), 8.01 (d, 1H, J=15 Hz), 7.36 (m, 2H), 4.62 (s, 2H), 3.70 (m, 2H), 3.11 (m, 2H), 2.97 (m, 2H), 1.19 (s, 6H); LCMS: purity: 99%; MS (m/e): 486 (MH⁺)

Example 18

N4-(2,2-dimethyl-3,4-dihydro-3-oxo-2H-pyrido[3,2-b][1,4]oxazin-6-yl)-5-fluoro-N2-[6-(4-methylpiperazin-1-yl)pyridin-3-yl]-2,4-pyrimidinediamine (Compound 18)

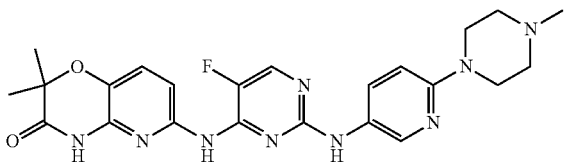

¹H NMR (DMSO-d₆): 8.38 (s, 1H), 8.05 (d, 1H, J=2.0 Hz), 7.81 (m, 1H), 7.44 (m, 1H), 7.33 (m, 1H), 6.72 (d, 1H, J=9.3 Hz), 3.41 (m, 8H), 2.18 (s, 3H), 1.41 (s, 6H); LCMS: purity: 99%; MS (m/e): 480 (MH⁺)

Example 19

N4-(3,4-dihydro-3-oxo-2H-pyrido[3,2-b][1,4]oxazin-6-yl)-5-fluoro-N2-[6-(4-methylpiperazin-1-yl)pyridin-3-yl]-2,4-pyrimidinediamine (Compound 19)

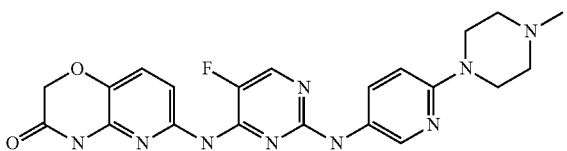

¹H NMR (DMSO-d₆): 8.37 (s, 1H), 8.02 (d, 1H, J=2.0 Hz), 7.81 (m, 1H), 7.41 (m, 1H), 7.19 (d, 1H, J=9.3 Hz), 6.75 (d, 1H, J=9.3 Hz), 4.47 (s, 2H), 3.35 (m, 8H), 2.18 (s, 3H); LCMS: purity: 99%; MS (m/e): 452 (MH⁺)

Example 20

N4-(2,2-dimethyl-3,4-dihydro-3-oxo-2H-pyrido[3,2-b][1,4]oxazin-6-yl)-5-fluoro-N2-[6-(homomorpholino)pyridin-3-yl]-2,4-pyrimidinediamine (Compound 20)

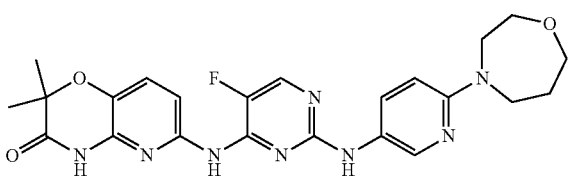 [SMILES: CC1(C)Oc2ccc(Nc3nc(Nc4ccc(N5CCCOCC5)nc4)ncc3F)nc2NC1=O]

¹H NMR (DMSO-d₆): 8.24 (d, 1H, J=1.3 Hz), 8.04 (d, 1H, J=2.0 Hz), 7.74 (m, 1H), 7.47 (m, 1H), 7.32 (m, 1H), 3.67 (m, 6H), 3.56 (m, 2H), 1.86 (m, 2H), 1.41 (s, 6H); LCMS: purity: 99%; MS (m/e): 481 (MH⁺)

Example 21

N4-(2,2-dimethyl-3,4-dihydro-3-oxo-2H-pyrido[3,2-b][1,4]oxazin-6-yl)-5-fluoro-N2-[5-methoxy-6-morpholinopyridin-3-yl]-2,4-pyrimidinediamine (Compound 21)

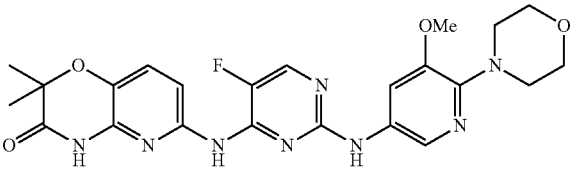 [SMILES: COc1cc(Nc2ncc(F)c(Nc3ccc4c(n3)NC(=O)C(C)(C)O4)n2)cnc1N1CCOCC1]

¹H NMR (DMSO-d₆): 8.36 (s, 1H), 8.19 (d, 1H, J=2.0 Hz), 7.99 (s, 1H), 7.37 (m, 2H), 3.69 (m, 4H), 2.92 (m, 4H), 3.15 (s, 3H), 1.41 (s, 6H); LCMS: purity: 99%; MS (m/e): 497 (MH⁺)

Example 22

N4-(2,2-dimethyl-3,4-dihydro-3-oxo-2H-pyrido[3,2-b][1,4]oxazin-6-yl)-5-fluoro-N2-[6-tetrahydropyranopyridin-3-yl]-2,4-pyrimidinediamine (Compound 22)

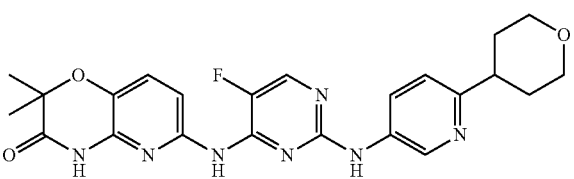 [SMILES: CC1(C)Oc2ccc(Nc3nc(Nc4ccc(C5CCOCC5)nc4)ncc3F)nc2NC1=O]

¹H NMR (DMSO-d₆): 8.12 (d, 1H, J=2.0 Hz), 8.01 (m, 1H), 7.39 (m, 2H), 7.07 (m, 1H), 3.93 (m, 2H), 3.44 (m, 2H), 2.84 (m, 1H), 1.69 (m, 4H), 1.41 (s, 6H); LCMS: purity: 99%; MS (m/e): 466 (MH⁺)

Example 23

N4-(2,2-dimethyl-3,4-dihydro-3-oxo-2H-pyrido[3,2-b][1,4]oxazin-6-yl)-5-fluoro-N2-[3-methyl-4-morpholinophenyl]-2,4-pyrimidinediamine (Compound 23)

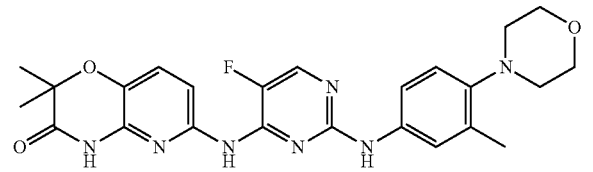 [SMILES: Cc1cc(Nc2ncc(F)c(Nc3ccc4c(n3)NC(=O)C(C)(C)O4)n2)ccc1N1CCOCC1]

¹H NMR (DMSO-d₆): 8.08 (d, 1H, J=2.0 Hz), 7.57 (m, 1H), 7.38 (m, 3H), 6.86 (m, 1H), 3.71 (m, 4H), 3.48 (m, 4H), 2.74 (s, 3H), 1.41 (s, 6H); LCMS: purity: 99%; MS (m/e): 480 (MH⁺)

Example 24

N4-(2,2-dimethyl-3,4-dihydro-3-oxo-2H-pyrido[3,2-b][1,4]oxazin-6-yl)-5-fluoro-N2-[3-methyl-4-((1S,4S)-5-oxa-2-aza-bicyclo[2.2.1]heptan-2-yl)phenyl]-2,4-pyrimidinediamine (Compound 24)

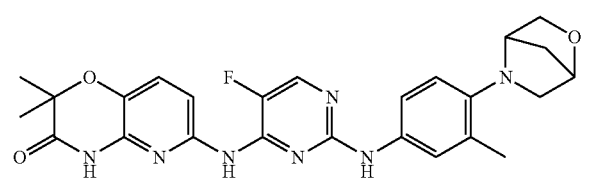 [SMILES: Cc1cc(Nc2ncc(F)c(Nc3ccc4c(n3)NC(=O)C(C)(C)O4)n2)ccc1N1CC2CC1CO2]

¹H NMR (DMSO-d₆): 8.06 (d, 1H, J=2.0 Hz), 7.57 (m, 1H), 7.32 (m, 3H), 6.70 (m, 1H), 4.49 (s, 1H), 3.85 (m, 1H), 3.68 (m, 1H), 3.27 (m, 1H), 3.02 (m, 1H), 2.98 (s, 3H), 1.83 (m, 2H), 1.41 (s, 6H); LCMS: purity: 99%; MS (m/e): 492 (MH⁺)

Example 25

N4-(2,2-dimethyl-3,4-dihydro-3-oxo-2H-pyrido[3,2-b][1,4]oxazin-6-yl)-5-fluoro-N2-[3-difluoromethoxy-4-morpholinophenyl]-2,4-pyrimidinediamine (Compound 25)

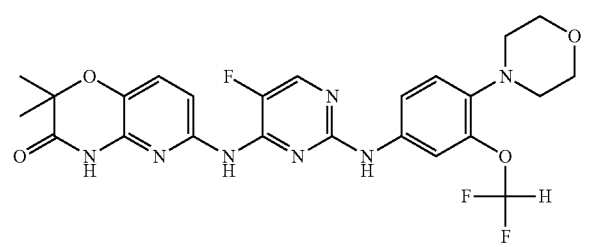 [SMILES: CC1(C)Oc2ccc(Nc3nc(Nc4ccc(N5CCOCC5)c(OC(F)F)c4)ncc3F)nc2NC1=O]

¹H NMR (Acetone-d₆/MeOH-d₄): 8.01 (m, 1H), 7.92 (d, 1H, J=2.0 Hz), 7.57 (m, 1H), 7.44 (m, 1H), 7.27 (m, 1H), 7.10 (m, 1H), 6.86 (s, 1H), 3.76 (m, 4H), 3.04 (m, 4H), 2.62 (s, 1H), 1.45 (s, 6H); LCMS: purity: 99%; MS (m/e): 532 (MH⁺)

Example 26

N4-(2,2-dimethyl-3,4-dihydro-3-oxo-2H-pyrido[3,2-b][1,4]oxazin-6-yl)-5-fluoro-N2-[3-fluoro-4-morpholinophenyl]-2,4-pyrimidinediamine (Compound 26)

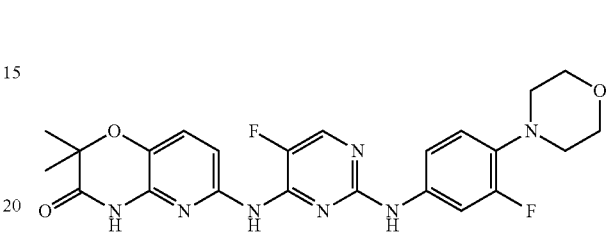

¹H NMR (DMSO-d₆): 8.12 (d, 1H, J=2.0 Hz), 7.62 (d, 1H, J=15.2 Hz), 7.47 (d, 1H, J=6 Hz), 7.36 (d, 1H, J=8.4 Hz), 7.26 (d, 1H, J=8.4 Hz), 6.86 (t, 1H, J=6 Hz, J=8.4 Hz), 3.69 (m, 4H), 2.87 (m, 4H), 1.41 (s, 6H); LCMS: purity: 99%; MS (m/e): 484 (MH⁺)

Example 27

N4-(2,2-dimethyl-3,4-dihydro-3-oxo-2H-pyrido[3,2-b][1,4]oxazin-6-yl)-5-fluoro-N2-[3-methoxy-4-morpholinophenyl]-2,4-pyrimidinediamine (Compound 27)

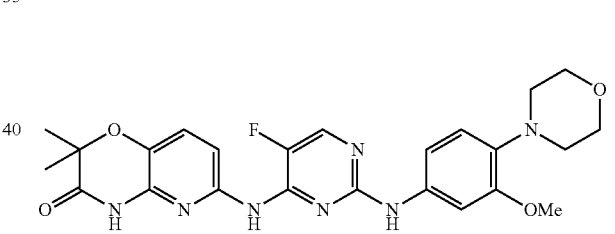

¹H NMR (DMSO-d₆): 8.08 (d, 1H, J=2.0 Hz), 7.58 (m, 1H), 7.47 (d, 1H, J=6 Hz), 7.24 (m, 3H), 6.72 (d, 1H, J=8.4 Hz), 3.65 (m, 7H), 2.85 (m, 4H), 1.41 (s, 6H); LCMS: purity: 99%; MS (m/e): 496 (MH⁺)

Example 28

N4-(2,2-dimethyl-3,4-dihydro-3-oxo-2H-pyrido[3,2-b][1,4]oxazin-6-yl)-5-fluoro-N2-[3-trifluoromethoxy-4-morpholinophenyl]-2,4-pyrimidinediamine (Compound 28)

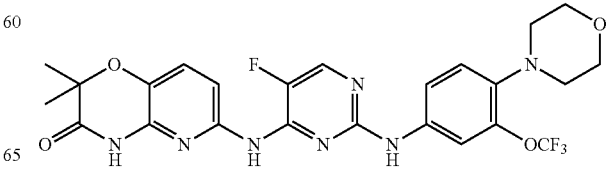

¹H NMR (DMSO-d₆): 8.11 (d, 1H, J=2.0 Hz), 7.58 (m, 4H), 7.01 (m, 1H), 3.67 (m, 4H), 2.86 (m, 4H), 1.41 (s, 6H); LCMS: purity: 99%; MS (m/e): 550 (MH⁺)

Example 29

N4-(2,2-dimethyl-3,4-dihydro-3-oxo-2H-pyrido[3,2-b][1,4]oxazin-6-yl)-5-fluoro-N2-[4-(4,4-difluoro-1-piperidinyl)phenyl]-2,4-pyrimidinediamine (Compound 29)

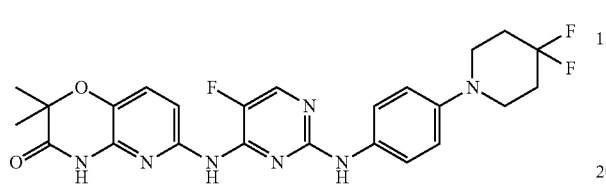

¹H NMR (DMSO-d₆): 8.11 (d, 1H, J=2.0 Hz), 7.44 (m, 4H), 6.92 (d, 1H, J=8.7 Hz), 3.24 (m, 4H), 2.05 (m, 4H), 1.41 (s, 6H); LCMS: purity: 99%; MS (m/e): 500 (MH⁺)

Example 30

N4-(2,2-dimethyl-3,4-dihydro-3-oxo-2H-pyrido[3,2-b][1,4]oxazin-6-yl)-5-fluoro-N2-[3-fluoro-4-(4,4-difluoro-1-piperidinyl)phenyl]-2,4-pyrimidinediamine (Compound 30)

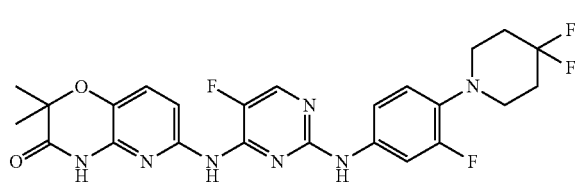 [SMILES: CC1(C)Oc2ccc(Nc3nc(Nc4ccc(N5CCC(F)(F)CC5)c(F)c4)ncc3F)nc2NC1=O]

¹H NMR (DMSO-d₆): 8.08 (d, 1H, J=2.0 Hz), 7.58 (d, 1H, J=15.9 Hz), 7.47 (d, 1H, J=6 Hz), 7.24 (m, 3H), 6.72 (d, 1H, J=8.4 Hz), 3.00 (m, 4H), 2.07 (m, 4H), 1.42 (s, 6H); LCMS: purity: 99%; MS (m/e): 518 (MH⁺)

Example 31

N4-(2,2-dimethyl-3,4-dihydro-3-oxo-2H-pyrido[3,2-b][1,4]oxazin-6-yl)-5-fluoro-N2-[3,5-difluoro-4-morpholinophenyl]-2,4-pyrimidinediamine (Compound 31)

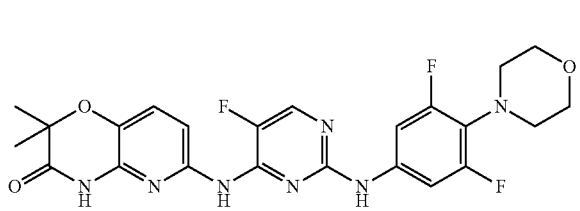 [SMILES: CC1(C)Oc2ccc(Nc3nc(Nc4cc(F)c(N5CCOCC5)c(F)c4)ncc3F)nc2NC1=O]

¹H NMR (DMSO-d₆): 8.15 (s, 1H), 7.36 (m, 4H), 7.01 (m, 1H), 3.62 (m, 4H), 2.95 (m, 4H), 1.41 (s, 6H); LCMS: purity: 99%; MS (m/e): 502 (MH⁺)

Example 32

N4-(3,4-dihydro-3-oxo-2H-pyrido[3,2-b][1,4]oxazin-6-yl)-5-fluoro-N2-[4-morpholino)phenyl]-2,4-pyrimidinediamine (Compound 32)

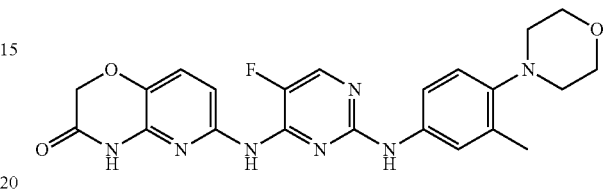

¹H NMR (DMSO-d₆): 8.08 (d, 1H, J=2.0 Hz), 7.57 (m, 1H), 7.38 (m, 3H), 6.86 (m, 1H), 4.61 (s, 2H), 3.71 (m, 4H), 3.48 (m, 4H), 2.74 (s, 3H); LCMS: purity: 99%; MS (m/e): 452 (MH⁺)

Example 33

N4-(3,4-dihydro-3-oxo-2H-pyrido[3,2-b][1,4]oxazin-6-yl)-5-fluoro-N2-[3-methoxy-4-morpholinophenyl]-2,4-pyrimidinediamine (Compound 33)

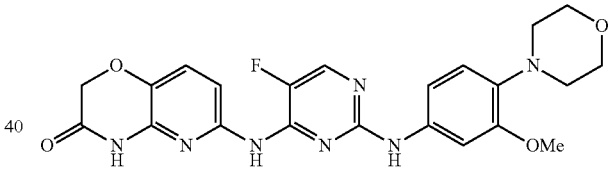

¹H NMR (DMSO-d₆): 8.08 (d, 1H, J=2.0 Hz), 7.58 (m, 1H), 7.59 (m, 1H), 7.38 (m, 2H), 6.74 (m, 1H), 4.61 (s, 2H), 3.65 (m, 7H), 3.54 (m, 4H), 2.74 (s, 3H); LCMS: purity: 99%; MS (m/e): 468 (MH⁺)

Example 34

N4-(3,4-dihydro-3-oxo-2H-pyrido[3,2-b][1,4]oxazin-6-yl)-5-fluoro-N2-[3-fluoro-4-morpholinophenyl]-2,4-pyrimidinediamine (Compound 34)

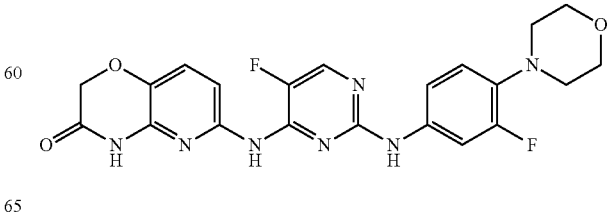

¹H NMR (DMSO-d₆): 8.08 (d, 1H, J=2.0 Hz), 7.64 (d, 1H, J=15.9 Hz), 7.44 (d, 1H, J=8.4 Hz), 7.30 (m, 2H), 6.88 (t, 1H,

J=6 Hz, J=8.4 Hz), 4.55 (s, 2H), 3.69 (m, 4H), 2.88 (m, 4H); LCMS: purity: 99%; MS (m/e): 456 (MH+)

Example 35 rac-Cis-N4-(3,4-dihydro-3-oxo-2H-pyrido[3,2-b][1,4]oxazin-6-yl)-5-fluoro-N2-[4-(2,6-dimethylmorpholino)phenyl]-2,4-pyrimidinediamine (Compound 35)

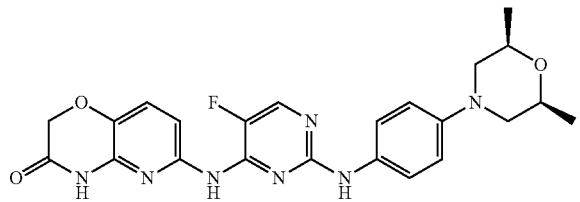

$^1$H NMR (DMSO-$d_6$): 8.06 (d, 1H, J=2.2 Hz), 7.47 (m, 4H), 6.82 (d, 2H, J=9.1 Hz), 4.61 (s, 2H), 3.69 (m, 2H), 3.42 (m, 2H), 2.18 (m, 2H), 1.14 (d, 6H, J=6.3 Hz); LCMS: purity: 98%; MS (m/e): 466 (MH+)

Example 36 rac-Cis-N4-(2,2-dimethyl-3,4-dihydro-3-oxo-2H-pyrido[3,2-b][1,4]oxazin-6-yl)-5-fluoro-N2-[4-(2,6-dimethylmorpholino)phenyl]-2,4-pyrimidinediamine (Compound 36)

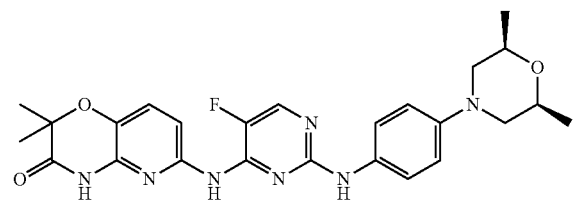 [SMILES: C[C@@H]1CN(c2ccc(Nc3ncc(F)c(Nc4ccc5c(n4)NC(=O)C(C)(C)O5)n3)cc2)C[C@H](C)O1]

$^1$H NMR (DMSO-$d_6$): 8.06 (d, 1H, J=2.2 Hz), 7.47 (m, 4H), 6.82 (d, 2H, J=9.1 Hz), 3.69 (m, 2H), 3.43 (m, 2H), 2.18 (m, 2H), 1.41 (s, 6H), 1.14 (d, 6H, J=6.3 Hz); LCMS: purity: 98%; MS (m/e): 494 (MH+)

Example 37

N4-(3,4-dihydro-3-oxo-2H-pyrido[3,2-b][1,4]oxazin-6-yl)-5-fluoro-N2-[4-((1S,4S)-5-oxa-2-aza-bicyclo[2.2.1]heptan-2-yl)phenyl]-2,4-pyrimidinediamine (Compound 37)

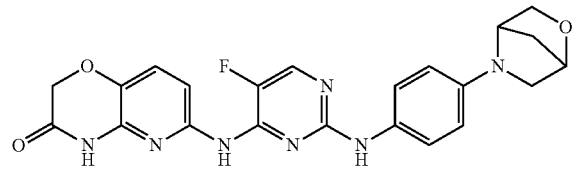 [SMILES: O=C1COc2ccc(Nc3nc(Nc4ccc(N5CC6CC5CO6)cc4)ncc3F)nc2N1]

$^1$H NMR (DMSO-$d_6$): 8.02 (d, 1H, J=2.1 Hz), 7.57 (d, 1H, J=8.4 Hz), 7.36 (m, 3H), 6.50 (d, 1H, J=8.8 Hz), 4.61 (s, 1H), 4.55 (s, 1H), 4.43 (s, 1H) 3.71 (d, 1H, J=7.0 Hz), 3.59 (d, 1H, J=7.3 Hz), 3.41 (d, 1H, J=9.3 Hz), 3.14 (d, 1H, J=9.3 Hz), 1.87 (d, 1H, J=9.7 Hz), 1.80 (d, 1H, J=9.4 Hz); LCMS: purity: 99%; MS (m/e): 450 (MH+)

Example 38

N4-(2,2-dimethyl-3,4-dihydro-3-oxo-2H-pyrido[3,2-b][1,4]oxazin-6-yl)-5-fluoro-N2-[4-((1S,4S)-5-oxa-2-aza-bicyclo[2.2.1]heptan-2-yl)phenyl]-2,4-pyrimidinediamine (Compound 38)

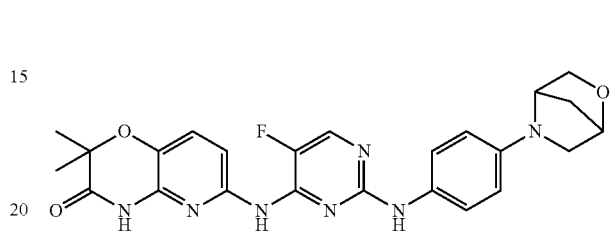

$^1$H NMR (DMSO-$d_6$): 8.02 (d, 1H, J=2.1 Hz), 7.57 (d, 1H, J=8.4 Hz), 7.36 (m, 3H), 6.50 (d, 1H, J=8.8 Hz), 4.55 (s, 1H), 4.43 (s, 1H) 3.71 (d, 1H, J=7.0 Hz), 3.59 (d, 1H, J=7.3 Hz), 3.41 (d, 1H, J=9.3 Hz), 3.14 (d, 1H, J=9.3 Hz), 1.87 (d, 1H, J=9.7 Hz), 1.80 (d, 1H, J=9.4 Hz), 1.41 (s, 6H); LCMS: purity: 99%; MS (m/e): 478 (MH+)

Example 39

N4-(3,4-dihydro-3-oxo-2H-pyrido[3,2-b][1,4]oxazin-6-yl)-5-fluoro-N2-[4-(morpholin-2-one)phenyl]-2,4-pyrimidinediamine (Compound 39)

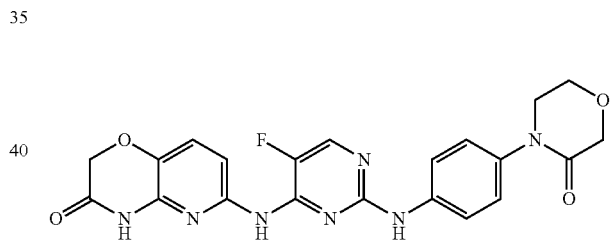

$^1$H NMR (DMSO-$d_6$): 8.11 (d, 1H, J=2.0 Hz), 7.63 (d, 2H, J=7.5 Hz), 7.39 (d, 1H, J=9 Hz), 7.35 (d, 1H, J=9 Hz), 7.18 (d, 1H, J=9 Hz), 4.61 (s, 2H), 4.15 (s, 2H), 3.94 (m, 2H), 3.66 (m, 2H); LCMS: purity: 99%; MS (m/e): 452 (MH+)

Example 40

N4-(2,2-dimethyl-3,4-dihydro-3-oxo-2H-pyrido[3,2-b][1,4]oxazin-6-yl)-5-fluoro-N2-[4-(morpholin-2-one)phenyl]-2,4-pyrimidinediamine (Compound 40)

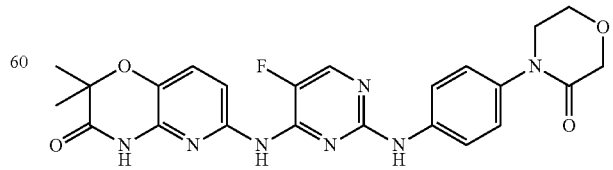

$^1$H NMR (DMSO-$d_6$): 8.11 (d, 1H, J=2.0 Hz), 7.65 (d, 2H, J=7.5 Hz), 7.55 (d, 1H, J=9 Hz), 7.39 (d, 1H, J=9 Hz), 7.18 (d,

1H, J=9 Hz), 4.15 (s, 2H), 3.94 (m, 2H), 3.66 (m, 2H), 1.41 (s, 6H); LCMS: purity: 99%; MS (m/e): 480 (MH⁺)

Example 41

N4-(3,4-dihydro-3-oxo-2H-pyrido[3,2-b][1,4]oxazin-6-yl)-5-fluoro-N2-[4-(((2S)-2-ethoxymethyl)morpholino)phenyl]-2,4-pyrimidinediamine (Compound 41)

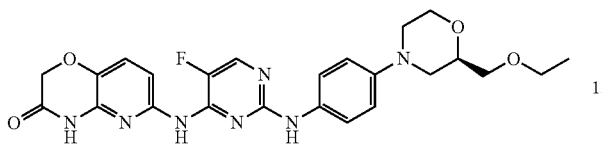

¹H NMR (DMSO-d₆): 8.05 (d, 1H, J=2.0 Hz), 7.48 (m, 4H), 6.80 (d, 1H, J=7.8 Hz), 4.61 (s, 2H), 3.91 (d, 1H, J=11.4 Hz), 3.66 (m, 2H), 3.50 (m, 6H), 2.61 (m, 2H), 2.34 (m, 2H), 1.10 (t, 3H, J=7.0 Hz); LCMS: purity: 99%; MS (m/e): 496 (MH⁺)

Example 42

N4-(2,2-dimethyl-3,4-dihydro-3-oxo-2H-pyrido[3,2-b][1,4]oxazin-6-yl)-5-fluoro-N2-[4-(((2S)-2-ethoxymethyl)morpholino)phenyl]-2,4-pyrimidinediamine (Compound 42)

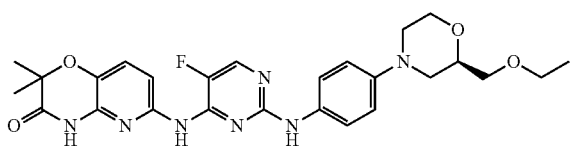 [SMILES: CCOC[C@H]1CN(c2ccc(Nc3ncc(F)c(Nc4ccc5c(n4)NC(=O)C(C)(C)O5)n3)cc2)CCO1]

¹H NMR (DMSO-d₆ 8.05 (d, 1H, J=2.0 Hz), 7.48 (m, 4H), 6.80 (d, 1H, J=7.8 Hz), 3.91 (d, 1H, J=11.4 Hz), 3.66 (m, 2H), 3.50 (m, 6H), 2.61 (m, 2H), 2.34 (m, 2H), 1.41 (s, 6H), 1.06 (t, 3H, J=7.0 Hz); LCMS: purity: 99%; MS (m/e): 524 (MH⁺)

Example 43

N4-(2,2-dimethyl-3,4-dihydro-3-oxo-2H-pyrido[3,2-b][1,4]oxazin-6-yl)-5-fluoro-N2-[4-homomorpholinophenyl]-2,4-pyrimidinediamine (Compound 43)

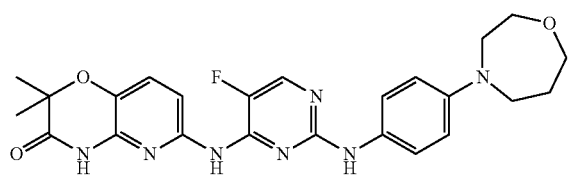 [SMILES: CC1(C)Oc2ccc(Nc3nc(Nc4ccc(N5CCCOCC5)cc4)ncc3F)nc2NC1=O]

¹H NMR (DMSO-d₆): 8.06 (d, 1H, J=3 Hz), 7.53 (m, 1H), 7.33 (m, 3H), 6.64 (m, 2H), 3.67 (m, 2H), 3.52 (m, 6H), 1.86 (m, 2H), 1.41 (s, 6H); LCMS: purity: 99%; MS (m/e): 480 (MH⁺)

Example 44

N4-(3,4-dihydro-3-oxo-2H-pyrido[3,2-b][1,4]oxazin-6-yl)-5-fluoro-N2-[4-homomorpholinophenyl]-2,4-pyrimidinediamine (Compound 44)

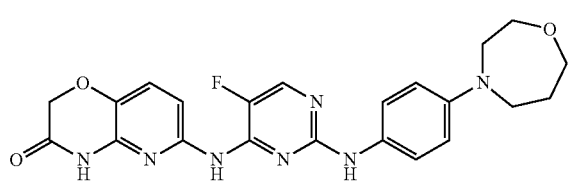 [SMILES: O=C1COc2ccc(Nc3nc(Nc4ccc(N5CCCOCC5)cc4)ncc3F)nc2N1]

¹H NMR (DMSO-d₆): 8.06 (d, 1H, J=3 Hz), 7.53 (m, 1H), 7.36 (d, 2H, J=8.7 Hz), 7.25 (d, 1H, J=8.4 Hz), 6.64 (d, 1H, J=8.7 Hz), 3.67 (m, 2H), 3.52 (m, 6H), 1.86 (m, 2H), 1.41 (s, 6H); LCMS: purity: 99%; MS (m/e): 452 (MH⁺)

Example 45

N4-(2,2-dimethyl-3,4-dihydro-3-oxo-2H-pyrido[3,2-b][1,4]oxazin-6-yl)-5-fluoro-N2-[3-(2-propoxy)-4-morpholinophenyl]-2,4-pyrimidinediamine (Compound 45)

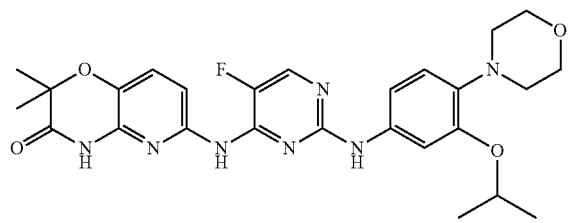 [SMILES: CC(C)Oc1cc(Nc2ncc(F)c(Nc3ccc4c(n3)NC(=O)C(C)(C)O4)n2)ccc1N1CCOCC1]

¹H NMR (DMSO-d₆): 8.08 (d, 1H, J=2.0 Hz), 7.59 (m, 1H), 7.47 (d, 1H, J=6 Hz), 7.24 (m, 3H), 6.72 (d, 1H, J=8.4 Hz), 4.43 (m, 1H), 3.67 (m, 4H), 2.87 (m, 4H), 1.41 (s, 6H), 1.21 (d, 6H, J=6 Hz); LCMS: purity: 99%; MS (m/e): 524 (MH⁺)

Example 46

N4-(3,4-dihydro-3-oxo-2H-pyrido[3,2-b][1,4]oxazin-6-yl)-5-fluoro-N2-[4-tetrahydropyranophenyl]-2,4-pyrimidinediamine (Compound 46)

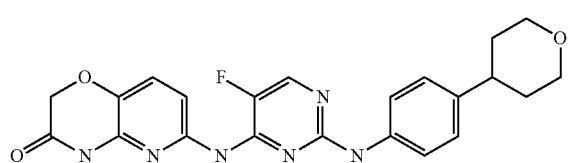

¹H NMR (DMSO-d₆): 8.08 (d, 1H, J=2.2 Hz), 7.53 (m, 3H), 7.37 (m, 1H, J=8.7 Hz), 7.07 (d, 2H, J=8.1 Hz), 4.61 (s, 2H), 3.92 (m, 2H), 3.39 (m, 2H), 2.65 (m, 1H), 1.61 (m, 4H); LCMS: purity: 98%; MS (m/e): 437 (MH+)

Example 47

N4-(2,2-dimethyl-3,4-dihydro-3-oxo-2H-pyrido[3,2-b][1,4]oxazin-6-yl)-5-fluoro-N2-[4-tetrahydropyranophenyl]-2,4-pyrimidinediamine (Compound 47)

¹H NMR (DMSO-d₆): 8.08 (d, 1H, J=2.2 Hz), 7.55 (m, 3H), 7.45 (m, 1H, J=8.7 Hz), 7.04 (d, 2H, J=8.1 Hz), 3.90 (m, 2H), 3.37 (m, 2H), 2.63 (m, 1H), 1.61 (m, 4H), 1.41 (s, 6H); LCMS: purity: 98%; MS (m/e): 465 (MH+)

Example 48

N4-(2,2-dimethyl-3,4-dihydro-3-oxo-2H-pyrido[3,2-b][1,4]oxazin-6-yl)-5-fluoro-N2-[-3-methoxy-4-tetrahydropyranophenyl]-2,4-pyrimidinediamine (Compound 48)

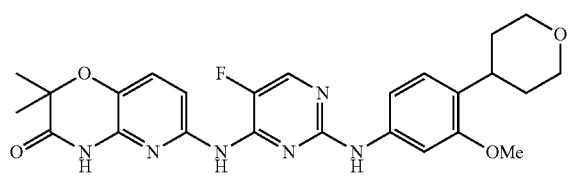 [SMILES: COc1cc(Nc2ncc(F)c(Nc3ccc4c(n3)NC(=O)C(C)(C)O4)n2)ccc1C1CCOCC1]

¹H NMR (DMSO-d₆): 8.11 (d, 1H, J=2.2 Hz), 7.61 (d, 1H, J=8.4 Hz), 7.35 (m, 2H), 7.28 (s, 1H), 6.98 (d, 1H, J=8.4 Hz), 3.90 (m, 2H), 3.65 (s, 3H), 3.37 (m, 2H), 2.93 (m, 1H), 1.61 (m, 4H), 1.41 (s, 6H); LCMS: purity: 98%; MS (m/e): 495 (MH+)

Example 49

N4-(3,4-dihydro-3-oxo-2H-pyrido[3,2-b][1,4]oxazin-6-yl)-5-fluoro-N2-[-3-methoxy-4-tetrahydropyranophenyl]-2,4-pyrimidinediamine (Compound 49)

¹H NMR (DMSO-d₆): 8.11 (d, 1H, J=2.2 Hz), 7.61 (d, 1H, J=8.4 Hz), 7.33 (m, 3H), 6.98 (d, 1H, J=8.4 Hz), 3.90 (m, 2H), 4.62 (s, 2H), 3.65 (s, 3H), 3.37 (m, 2H), 2.93 (m, 1H), 1.61 (m, 4H); LCMS: purity: 98%; MS (m/e): 467 (MH+)

Example 50

N4-(2,2-dimethyl-3,4-dihydro-3-oxo-2H-pyrido[3,2-b][1,4]oxazin-6-yl)-5-fluoro-N2-[6-((3R)-3-methylmorpholino)pyridin-3-yl]-2,4-pyrimidinediamine (Compound 50)

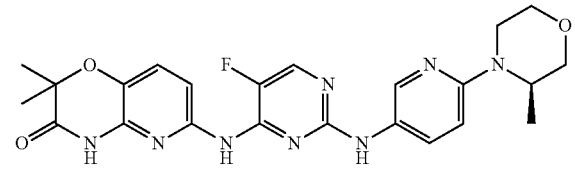 [SMILES: C[C@@H]1COCCN1c1ccc(Nc2ncc(F)c(Nc3ccc4c(n3)NC(=O)C(C)(C)O4)n2)cn1]

¹H NMR (DMSO-d₆): δ 11.02 (s, 1H), 9.23 (s, 1H), 9.04 (s, 1H), 8.38 (s, 1H), 8.06 (m, 1H), 7.83 (m, 1H), 7.46 (m, 1H), 7.32 (m, 1H), 6.70 (m, 1H), 4.21 (m, 1H), 3.88 (m, 1H), 3.70-3.43 (m, 4H), 3.01 (m, 1H), 1.41 (s, 6H), 1.05 (d, J=6.6 Hz, 3H); LC-MS: purity: 100.00%; MS (m/e): 481.11 (MH+).

Example 51

N4-(3,4-dihydro-3-oxo-2H-pyrido[3,2-b][1,4]oxazin-6-yl)-5-fluoro-N2-[6-((3R)-3-methylmorpholino)pyridin-3-yl]-2,4-pyrimidinediamine (Compound 51)

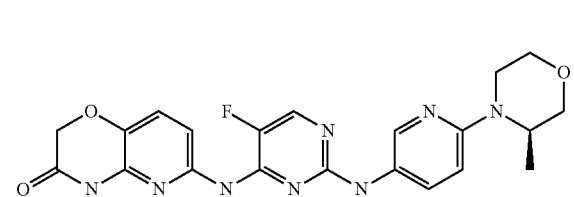

¹H NMR (DMSO-d₆): δ 11.06 (s, 1H), 9.24 (s, 1H), 9.03 (s, 1H), 8.41 (s, 1H), 8.06 (m, 1H), 7.83 (m, 1H), 7.47 (m, 1H), 7.31 (m, 1H), 6.72 (m, 1H), 4.61 (s, 2H), 4.22 (m, 1H), 3.91 (m, 1H), 3.71-3.34 (m, 4H), 3.02 (m, 1H), 1.06 (d, J=6.6 Hz, 3H); LC-MS: purity: 100.00%; MS (m/e): 453.05 (MH+).

Example 52

N4-(2,2-dimethyl-3,4-dihydro-3-oxo-2H-pyrido[3,2-b][1,4]oxazin-6-yl)-5-fluoro-N2-[6-(4-hydroxypiperidin-1-yl)pyridin-3-yl]-2,4-pyrimidinediamine (Compound 52)

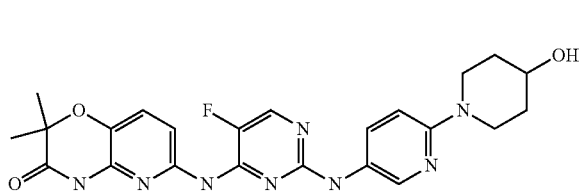

¹H NMR (DMSO-d₆): δ 11.02 (s, 1H), 9.16 (s, 1H), 8.94 (s, 1H), 8.33 (s, 1H), 8.06 (m, 1H), 7.76 (m, 1H), 7.46 (m, 1H), 7.32 (m, 1H), 6.71 (m, 1H), 4.61 (m, 1H), 3.90 (m, 2H), 3.62 (m, 1H), 2.94 (m, 2H), 1.75 (m, 2H), 1.41 (s, 6H), 1.31 (m, 2H); LC-MS: purity: 100.00%; MS (m/e): 481.13 (MH+).

Example 53

N4-(2,2-dimethyl-3,4-dihydro-3-oxo-2H-pyrido[3,2-b][1,4]oxazin-6-yl)-5-fluoro-N2-[6-(4-methoxypiperidin-1-yl)pyridin-3-yl]-2,4-pyrimidinediamine (Compound 53)

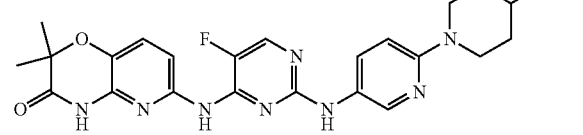

¹H NMR (DMSO-d₆): δ 11.02 (s, 1H), 9.17 (s, 1H), 8.95 (s, 1H), 8.34 (s, 1H), 8.05 (m, 1H), 7.76 (m, 1H), 7.46 (m, 1H), 7.32 (m, 1H), 6.73 (m, 1H), 3.84 (m, 2H), 3.35 (m, 2H), 3.24 (s, 3H), 3.01 (m, 2H), 1.86 (m, 2H), 1.41 (s, 6H), 1.36 (m, 2H); LC-MS: purity: 100.00%; MS (m/e): 495.40 (MH+).

Example 54

N4-(2,2-dimethyl-3,4-dihydro-3-oxo-2H-pyrido[3,2-b][1,4]oxazin-6-yl)-5-fluoro-N2-[6-(4-ethoxypiperidin-1-yl)pyridin-3-yl]-2,4-pyrimidinediamine (Compound 54)

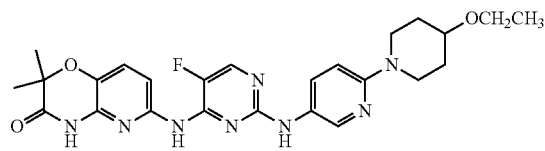 [SMILES: CCOC1CCN(c2ccc(Nc3ncc(F)c(Nc4ccc5c(n4)NC(=O)C(C)(C)O5)n3)cn2)CC1]

¹H NMR (DMSO-d₆): δ 11.04 (s, 1H), 9.24 (s, 1H), 9.07 (s, 1H), 8.34 (s, 1H), 8.08 (m, 1H), 7.85 (m, 1H), 7.46 (m, 1H), 7.33 (m, 1H), 6.86 (m, 1H), 3.87 (m, 2H), 3.47 (q, d=7.2 Hz, 2H), 3.06 (m, 2H), 1.86 (m, 2H), 1.41 (s, 6H), 1.34 (m, 2H), 1.09 (t, J=7.2 Hz, 3H); LC-MS: purity: 100.00%; MS (m/e): 509.40 (MH+).

Example 55

N4-(2,2-dimethyl-3,4-dihydro-3-oxo-2H-pyrido[3,2-b][1,4]oxazin-6-yl)-5-fluoro-N2-[6-((3R)-3-hydroxypyrrolidin-1-yl)pyridin-3-yl]-2,4-pyrimidinediamine (Compound 55)

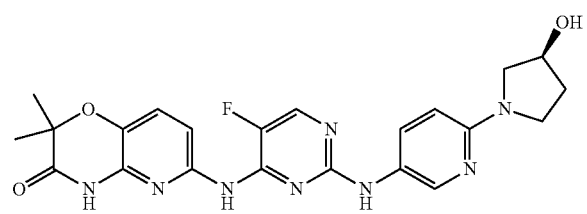 [SMILES: CC1(C)Oc2ccc(Nc3nc(Nc4ccc(N5CC[C@H](O)C5)nc4)ncc3F)nc2NC1=O]

¹H NMR (DMSO-d₆): δ 11.04 (s, 1H), 9.13 (s, 1H), 8.86 (s, 1H), 8.26 (s, 1H), 8.02 (m, 1H), 7.74 (m, 1H), 7.45 (m, 1H), 7.31 (m, 1H), 6.32 (m, 1H), 4.90 (m, 1H), 4.34 (bs, 1H), 3.45 (m, 2H), 3.25 (m, 1H), 1.97 (m, 1H), 1.86 (m, 1H), 1.41 (s, 6H); LC-MS: purity: 100.00%; MS (m/e): 467.08 (MH+).

Example 56

N4-(2,2-dimethyl-3,4-dihydro-3-oxo-2H-pyrido[3,2-b][1,4]oxazin-6-yl)-5-fluoro-N2-[6-((3R)-3-methoxypyrrolidin-1-yl)pyridin-3-yl]-2,4-pyrimidinediamine (Compound 56)

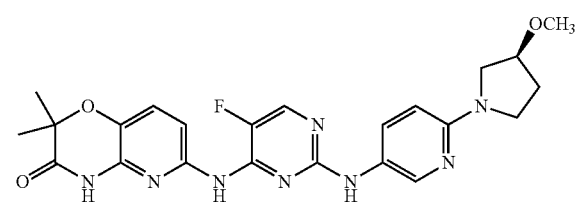 [SMILES: CO[C@H]1CCN(c2ccc(Nc3ncc(F)c(Nc4ccc5c(n4)NC(=O)C(C)(C)O5)n3)cn2)C1]

¹H NMR (DMSO-d₆): δ 11.03 (s, 1H), 9.15 (s, 1H), 8.88 (s, 1H), 8.28 (s, 1H), 8.03 (m, 1H), 7.74 (m, 1H), 7.45 (m, 1H), 7.31 (m, 1H), 6.35 (m, 1H), 4.03 (m, 1H), 3.43 (m, 4H), 3.24 (s, 3H), 2.02 (m, 2H), 1.41 (s, 6H); LC-MS: purity: 100.00%; MS (m/e): 481.11 (MH+).

Example 57

N4-(2,2-dimethyl-3,4-dihydro-3-oxo-2H-pyrido[3,2-b][1,4]oxazin-6-yl)-5-fluoro-N2-1-2,4-pyrimidinediamine (Compound 57)

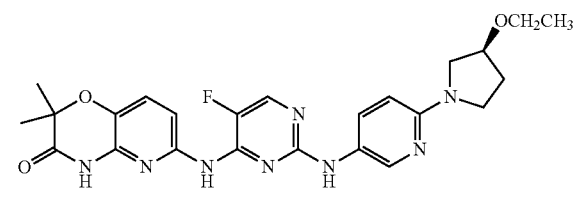 [SMILES: CCO[C@H]1CCN(c2ccc(Nc3ncc(F)c(Nc4ccc5c(n4)NC(=O)C(C)(C)O5)n3)cn2)C1]

¹H NMR (DMSO-d₆): δ 11.04 (s, 1H), 9.15 (s, 1H), 8.88 (s, 1H), 8.28 (s, 1H), 8.03 (m, 1H), 7.74 (m, 1H), 7.45 (m, 1H), 7.31 (m, 1H), 6.35 (m, 1H), 4.13 (m, 1H), 3.48-3.43 (m, 6H), 2.01 (m, 2H), 1.41 (s, 6H), 1.08 (t, J=7.2 Hz, 3H); LC-MS: purity: 100.00%; MS (m/e): 495.11 (MH+).

Example 58

N4-(2,2-dimethyl-3,4-dihydro-3-oxo-2H-pyrido[3,2-b][1,4]oxazin-6-yl)-5-fluoro-N2-[6-(3-methylenemorpholino)pyridin-3-yl]-2,4-pyrimidinediamine (Compound 58)

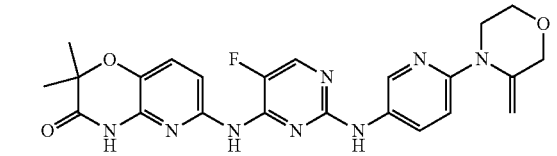 [SMILES: C=C1COCCN1c1ccc(Nc2ncc(F)c(Nc3ccc4c(n3)NC(=O)C(C)(C)O4)n2)cn1]

¹H NMR (CD₃OD): δ 8.99 (s, 1H), 8.40 (m, 2H), 8.10 (m, 1H), 7.98 (m, 2H), 7.29 (d, J=8.4 Hz, 1H), 7.10 (d, J=9.9 Hz, 1H), 4.31 (m, 2H), 4.11 (m, 1H), 4.01 (d, J=9.0 Hz, 1H), 3.84 (d, J=11.4 Hz, 1H), 3.54 (m, 3H), 1.49 (s, 6H); LC-MS: purity: 100.00%; MS (m/e): 479.09 (MH+).

Example 59

N4-(2,2-dimethyl-3,4-dihydro-3-oxo-2H-pyrido[3,2-b][1,4]oxazin-6-yl)-5-fluoro-N2-[6-(3-(ethoxymethyl)morpholino)pyridin-3-yl]-2,4-pyrimidinediamine (Compound 59)

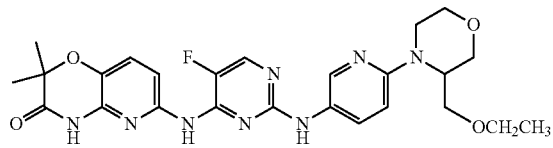 [SMILES: CCOCC1COCCN1c1ccc(Nc2ncc(F)c(Nc3ccc4c(n3)NC(=O)C(C)(C)O4)n2)cn1]

¹H NMR (DMSO-d₆): δ 11.04 (s, 1H), 9.18 (s, 1H), 9.00 (s, 1H), 8.35 (s, 1H), 8.06 (m, 1H), 7.81 (m, 1H), 7.46 (m, 1H), 7.32 (m, 1H), 6.68 (m, 1H), 418 (m, 1H), 3.93 (m, 2H), 3.66 (q, d=7.2 Hz, 2H), 3.45 (m, 4H), 3.22 (m, 2H), 2.99 (m, 1H), 1.40 (s, 6H), 1.05 (t, J=7.2 Hz, 3H); LC-MS: purity: 100.00%; MS (m/e): 525.13 (MH+).

Example 60

N4-(2,2-dimethyl-3,4-dihydro-3-oxo-2H-pyrido[3,2-b][1,4]oxazin-6-yl)-5-fluoro-N2-[6-(4-morpholinopiperidin-1-yl)pyridin-3-yl]-2,4-pyrimidinediamine (Compound 60)

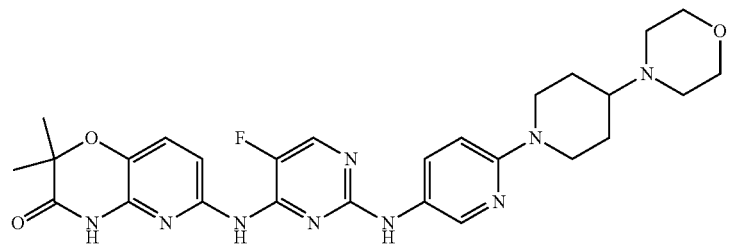 [SMILES: CC1(C)Oc2ccc(Nc3nc(Nc4ccc(N5CCC(N6CCOCC6)CC5)nc4)ncc3F)nc2NC1=O]

¹H NMR (DMSO-d₆): δ 11.06 (s, 1H), 9.36 (s, 1H), 9.20 (s, 1H), 8.43 (s, 1H), 8.10 (m, 1H), 7.92 (m, 1H), 7.66 (m, 1H), 7.46 (m, 1H), 7.38 (m, 1H), 6.88 (m, 1H), 4.34 (m, 2H), 3.97 (m, 2H), 3.81 (m, 3H), 3.07 (m, 3H), 2.79 (m, 3H), 2.16 (m, 2H), 1.66 (m, 2H), 1.41 (s, 6H); LC-MS: purity: 100.00%; MS (m/e): 550.17 (MH+).

Example 61

N4-(2,2-dimethyl-3,4-dihydro-3-oxo-2H-pyrido[3,2-b][1,4]oxazin-6-yl)-5-fluoro-N2-[6-(4-(diethylamino)piperidin-1-yl)pyridin-3-yl]-2,4-pyrimidinediamine (Compound 61)

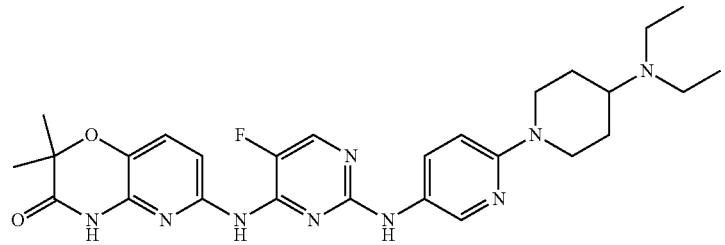 [SMILES: CCN(CC)C1CCN(c2ccc(Nc3ncc(F)c(Nc4ccc5c(n4)NC(=O)C(C)(C)O5)n3)cn2)CC1]

¹H NMR (DMSO-d₆): δ 11.09 (s, 1H), 9.56 (s, 1H), 9.44 (s, 1H), 9.03 (s, 1H), 8.41 (s, 1H), 8.15 (m, 1H), 7.98 (m, 1H), 7.39 (m, 1H), 7.11 (m, 1H), 4.26 (m, 2H), 3.56 (m, 2H), 2.99 (m, 4H), 2.03 (m, 3H), 1.65 (m, 2H), 1.42 (s, 6H), 1.21 (t, J=7.2 Hz, 6H); LC-MS: purity: 100.00%; MS (m/e): 536.46 (MH+).

Example 62

N4-(2,2-dimethyl-3,4-dihydro-3-oxo-2H-pyrido[3,2-b][1,4]oxazin-6-yl)-5-fluoro-N2-[6-(1,4-diazabicyclo[3.2.2]nonan-4-yl)pyridin-3-yl]-2,4-pyrimidinediamine (Compound 62)

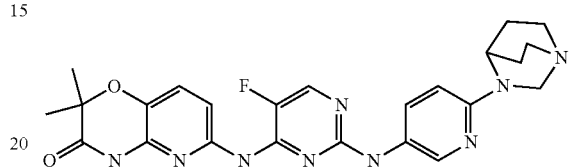

¹H NMR (CD₃OD): δ 8.46 (m, 2H), 7.93 (m, 1H), 7.78 (m, 2H), 7.23 (m, 1H), 6.79 (m, 1H), 4.60 (m, 1H), 4.17 (m, 2H), 3.50 (m, 6H), 2.32 (m, 2H), 2.13 (m, 2H), 1.41 (s, 6H); LC-MS: purity: 100.00%; MS (m/e): 506.11 (MH+).

Example 63

N4-(3,4-dihydro-3-oxo-2H-pyrido[3,2-b][1,4]oxazin-6-yl)-5-fluoro-N2-[6-((3S)-3-hydroxypyrrolidin-1-yl)pyridin-3-yl]-2,4-pyrimidinediamine (Compound 63)

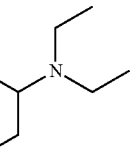
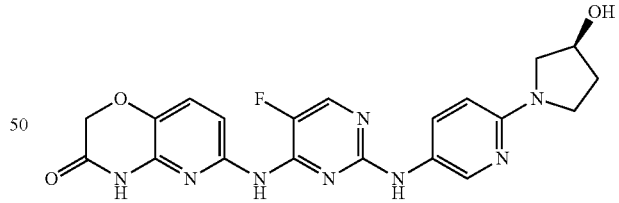

¹H NMR (DMSO-d₆): δ 11.14 (m, 1H), 9.42 (m, 2H), 8.38 (s, 1H), 8.15 (m, 2H), 7.40 (m, 2H), 7.02 (m, 1H), 5.23 (bs, 1H), 4.63 (s, 2H), 4.44 (s, 1H), 3.54 (m, 2H), 3.35 (m, 2H), 2.04 (m, 2H); LC-MS: purity: 100.00%; MS (m/e): 439.20 (MH+).

Example 64

N4-(2,2-dimethyl-3,4-dihydro-3-oxo-2H-pyrido[3,2-b][1,4]oxazin-6-yl)-5-fluoro-N2-[6-((3R)-3-hydroxypyrrolidin-1-yl)pyridin-3-yl]-2,4-pyrimidinediamine (Compound 64)

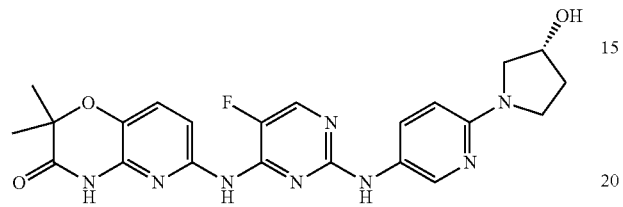

¹H NMR (DMSO-d₆): δ 11.04 (s, 1H), 9.13 (s, 1H), 8.86 (s, 1H), 8.26 (s, 1H), 8.02 (m, 1H), 7.74 (m, 1H), 7.45 (m, 1H), 7.31 (m, 1H), 6.32 (m, 1H), 4.90 (m, 1H), 4.34 (bs, 1H), 3.45 (m, 2H), 3.25 (m, 1H), 1.97 (m, 1H), 1.86 (m, 1H), 1.41 (s, 6H); LC-MS: purity: 100.00%; MS (m/e): 467.13 (MH+).

Example 65

N4-(2,2-dimethyl-3,4-dihydro-3-oxo-2H-pyrido[3,2-b][1,4]oxazin-6-yl)-5-fluoro-N2-[6-((3R)-3-methoxypyrrolidin-1-yl)pyridin-3-yl]-2,4-pyrimidinediamine (Compound 65)

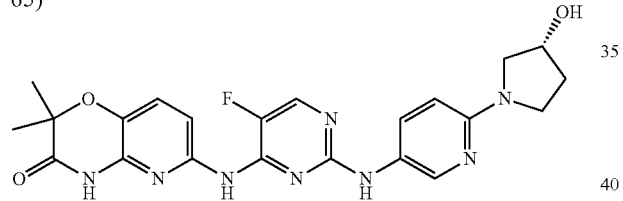

¹H NMR (DMSO-d₆): δ 11.03 (s, 1H), 9.14 (s, 1H), 8.87 (s, 1H), 8.29 (s, 1H), 8.02 (m, 1H), 7.72 (m, 1H), 7.45 (m, 1H), 7.31 (m, 1H), 6.34 (m, 1H), 4.03 (s, 1H), 3.43 (m, 2H), 3.23 (m, 2H), 2.02 (m, 2H), 1.41 (s, 6H); LC-MS: purity: 100.00%; MS (m/e): 481.13 (MH+).

Example 66

N4-(2,2-dimethyl-3,4-dihydro-3-oxo-2H-pyrido[3,2-b][1,4]oxazin-6-yl)-5-fluoro-N2-[6-(3-(diethylamino)pyrrolidin-1-yl)pyridin-3-yl]-2,4-pyrimidinediamine (Compound 66)

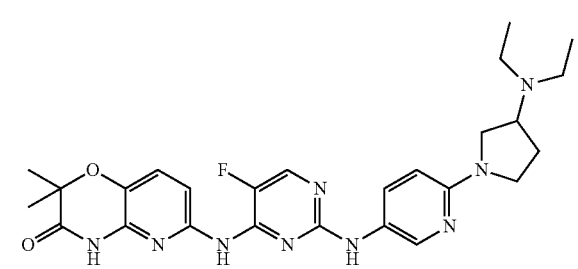 [SMILES: CCN(CC)C1CCN(c2ccc(Nc3ncc(F)c(Nc4ccc5c(n4)NC(=O)C(C)(C)O5)n3)cn2)C1]

¹H NMR (DMSO-d₆): δ 11.07 (s, 1H), 9.48 (s, 1H), 9.35 (s, 1H), 8.48 (s, 1H), 8.14 (m, 1H), 8.03 (m, 1H), 7.46 (m, 1H), 7.38 (m, 1H), 6.85 (m, 1H), 4.09 (m, 3H), 3.94 (m, 2H), 3.68-3.41 (m, 3H), 3.26 (m, 3H), 2.22 (m, 1H), 1.41 (s, 6H), 1.23 (m, 6H); LC-MS: purity: 100.00%; MS (m/e): 522.15 (MH+).

Example 67

N4-(2,2-dimethyl-3,4-dihydro-3-oxo-2H-pyrido[3,2-b][1,4]oxazin-6-yl)-5-fluoro-N2-[6-(3-morpholinopyrrolidin-1-yl)pyridin-3-yl]-2,4-pyrimidinediamine (Compound 67)

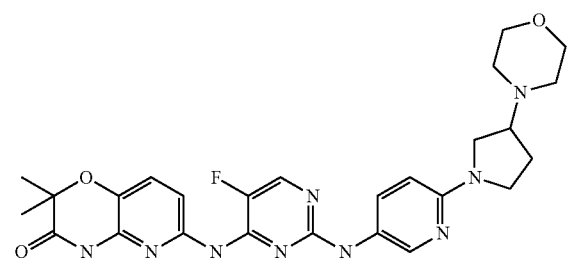

¹H NMR (DMSO-d₆): δ 11.03 (s, 1H), 9.20 (s, 1H), 8.94 (s, 1H), 8.36 (m, 1H), 8.05 (m, 1H), 7.79 (m, 1H), 7.44 (m, 1H), 7.38 (m, 1H), 6.42 (m, 1H), 3.80-3.42 (m, 6H), 3.32-3.24 (m, 7H), 2.26 (m, 2H), 1.41 (s, 6H); LC-MS: purity: 100.00%; MS (m/e): 536.18 (MH+).

Example 68

N4-(2,2-dimethyl-3,4-dihydro-3-oxo-2H-pyrido[3,2-b][1,4]oxazin-6-yl)-5-fluoro-N2-[6-((3R)-3-(ethylamino)pyyriolidin-1-yl)pyridin-3-yl]-2,4-pyrimidinediamine (Compound 68)

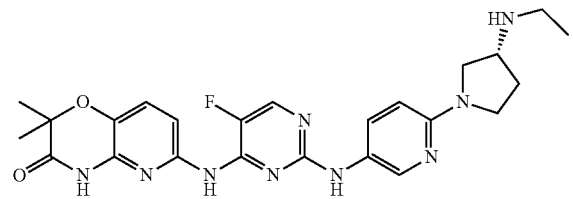 [SMILES: CCN[C@@H]1CCN(c2ccc(Nc3ncc(F)c(Nc4ccc5c(n4)NC(=O)C(C)(C)O5)n3)cn2)C1]

¹H NMR (DMSO-d₆): δ 11.03 (s, 1H), 9.18 (s, 1H), 8.86 (s, 1H), 8.25 (m, 1H), 8.03 (m, 1H), 7.73 (m, 1H), 7.44 (m, 1H), 7.30 (m, 1H), 6.31 (m, 1H), 3.52-3.25 (m, 4H), 3.06 (m, 1H), 2.58 (m, 2H), 2.06 (m, 1H), 1.74 (m, 2H), 1.41 (s, 6H), 0.99 (t, J=7.2 Hz, 3H); LC-MS: purity: 100.00%; MS (m/e): 494.16 (MH+).

Example 69

N4-(2,2-dimethyl-3,4-dihydro-3-oxo-2H-pyrido[3,2-b][1,4]oxazin-6-yl)-5-fluoro-N2-[6-(3-methoxyazetidin-1-yl)pyridin-3-yl]-2,4-pyrimidinediamine (Compound 69)

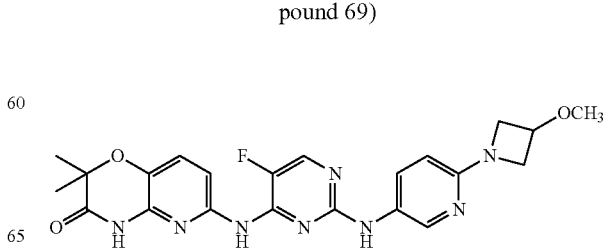

¹H NMR (CD₃OD): δ 8.51 (m, 2H), 7.97 (m, 2H), 7.80 (m, 1H), 7.28 (m, 1H), 6.92 (m, 1H), 4.30 (m, 2H), 4.07 (bs, 1H), 3.65 (m, 1H), 3.51 (m, 1H), 3.43 (s, 3H), 1.49 (s, 6H); LC-MS: purity: 100.00%; MS (m/e): 467.09 (MH+).

Example 70

N4-(2,2-dimethyl-3,4-dihydro-3-oxo-2H-pyrido[3,2-b][1,4]oxazin-6-yl)-5-fluoro-N2-[6-(3-(aminocarbonyl)pyrrolidin-1-yl)pyridin-3-yl]-2,4-pyrimidinediamine (Compound 70)

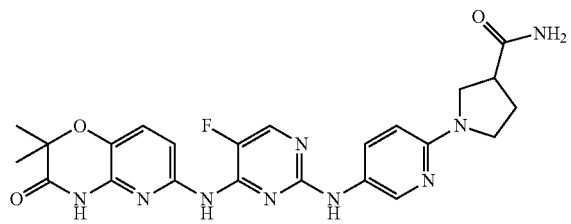 [SMILES: CC1(C)Oc2ccc(Nc3nc(Nc4ccc(N5CCC(C(N)=O)C5)nc4)ncc3F)nc2NC1=O]

¹H NMR (DMSO-d₆): δ 11.11 (s, 1H), 9.43 (m, 2H), 8.36 (s, 1H), 8.17 (m, 2H), 7.56 (m, 2H), 7.40 (m, 1H), 7.06 (m, 2H), 3.60 (m, 4H), 3.16 (m, 1H), 2.27 (m, 1H), 2.12 (m, 1H), 1.41 (s, 6H); LC-MS: purity: 100.00%; MS (m/e): 494.16 (MH+).

Example 71

N4-(2,2-dimethyl-3,4-dihydro-3-oxo-2H-pyrido[3,2-b][1,4]oxazin-6-yl)-5-fluoro-N2-[6-((3S)-3-(hydroxymethyl)pyrrolidin-1-yl)pyridin-3-yl]-2,4-pyrimidinediamine (Compound 71)

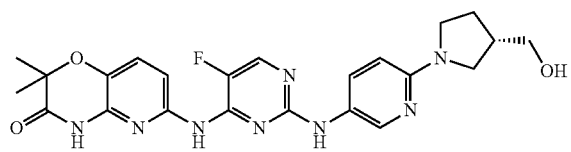 [SMILES: CC1(C)Oc2ccc(Nc3nc(Nc4ccc(N5CC[C@H](CO)C5)nc4)ncc3F)nc2NC1=O]

¹H NMR (DMSO-d₆): δ 11.11 (s, 1H), 9.46 (m, 2H), 8.34 (s, 1H), 8.17 (m, 2H), 7.55 (m, 2H), 7.40 (m, 1H), 7.06 (m, 2H), 4.48 (m, 1H), 3.60-3.24 (m, 5H), 2.09 (m, 1H), 1.82 (m, 1H), 1.41 (s, 6H); LC-MS: purity: 100.00%; MS (m/e): 481.13 (MH+).

Example 72

N4-(2,2-dimethyl-3,4-dihydro-3-oxo-2H-pyrido[3,2-b][1,4]oxazin-6-yl)-5-fluoro-N2-[6-(2-oxooxazolidin-3-yl)pyridin-3-yl]-2,4-pyrimidinediamine (Compound 72)

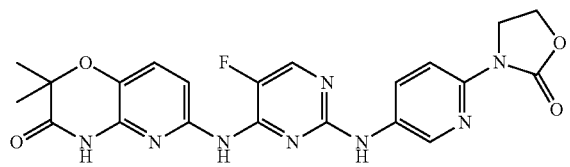 [SMILES: CC1(C)Oc2ccc(Nc3nc(Nc4ccc(N5CCOC5=O)nc4)ncc3F)nc2NC1=O]

¹H NMR (DMSO-d₆): δ 11.02 (s, 1H), 9.39 (m, 2H), 8.66 (s, 1H), 8.14 (m, 2H), 7.86 (m, 1H), 7.40 (m, 2H), 4.41 (t, J=8.4 Hz, 2H), 4.11 (t, J=8.4 Hz, 2H), 1.42 (s, 6H); LC-MS: purity: 100.00%; MS (m/e): 467.10 (MH+).

Example 73

N4-(2,2-dimethyl-3,4-dihydro-3-oxo-2H-pyrido[3,2-b][1,4]oxazin-6-yl)-5-fluoro-N2-[6-((4R)-4-isopropyl-2-oxooxazolidin-3-yl)pyridin-3-yl]-2,4-pyrimidinediamine (Compound 73)

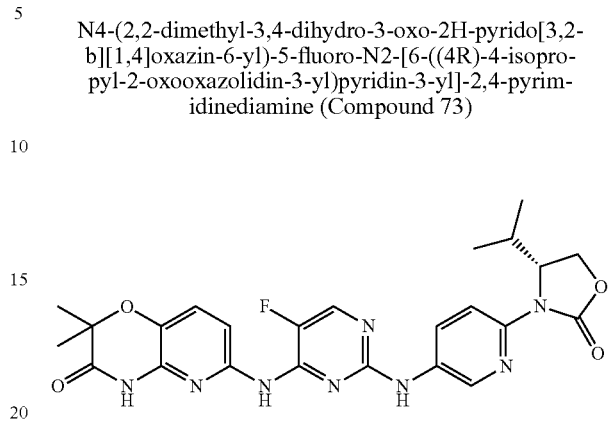

¹H NMR (DMSO-d₆): δ 11.04 (s, 1H), 9.41 (m, 2H), 8.69 (s, 1H), 8.08 (m, 2H), 7.78 (m, 1H), 7.36 (m, 2H), 4.75 (m, 1H), 4.36 (m, 2H), 2.25 (m, 1H), 1.42 (s, 6H), 0.84 (d, J=6.9 Hz, 3H), 0.71 (d, J=6.9 Hz, 3H); LC-MS: purity: 100.00%; MS (m/e): 509.24 (MH+).

Example 74

N4-(2,2-dimethyl-3,4-dihydro-3-oxo-2H-pyrido[3,2-b][1,4]oxazin-6-yl)-5-fluoro-N2-[6-((4S)-4-isopropyl-2-oxooxazolidin-3-yl)pyridin-3-yl]-2,4-pyrimidinediamine (Compound 74)

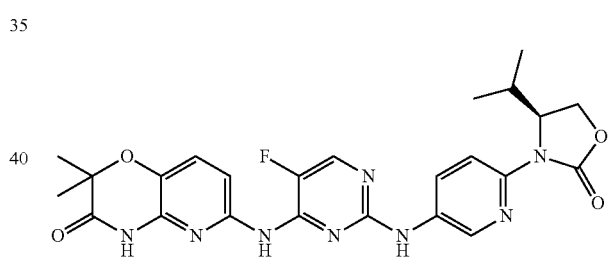

¹H NMR (DMSO-d₆): δ 11.04 (s, 1H), 9.41 (m, 2H), 8.69 (s, 1H), 8.08 (m, 2H), 7.78 (m, 1H), 7.36 (m, 2H), 4.75 (m, 1H), 4.36 (m, 2H), 2.25 (m, 1H), 1.42 (s, 6H), 0.84 (d, J=6.9 Hz, 3H), 0.71 (d, J=6.9 Hz, 3H); LC-MS: purity: 100.00%; MS (m/e): 509.46 (MH+).

Example 75

N4-(2,2-dimethyl-3,4-dihydro-3-oxo-2H-pyrido[3,2-b][1,4]oxazin-6-yl)-5-fluoro-N2-[2,3'-bipyridin-5-yl]-2,4-pyrimidinediamine (Compound 75)

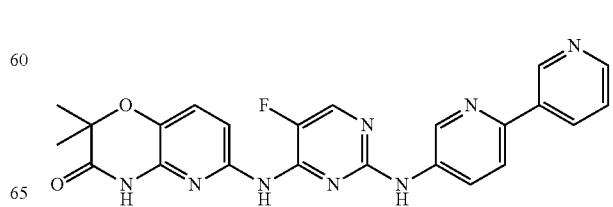

¹H NMR (DMSO-d₆): δ 11.15 (s, 1H), 10.27 (s, 1H), 9.58 (m, 1H), 9.19 (m, 1H), 8.58 (m, 1H), 8.22 (m, 1H), 8.09 (m, 1H), 7.92 (m, 1H), 7.41 (m, 2H), 7.92 (m, 1H), 7.41 (m, 2H), 7.06 (m, 1H), 6.09 (s, 2H), 1.44 (s, 6H); LC-MS: purity: 100.00%; MS (m/e): 459.03 (MH+).

Example 76

N4-(2,2-dimethyl-3,4-dihydro-3-oxo-2H-pyrido[3,2-b][1,4]oxazin-6-yl)-5-fluoro-N2-[6-methylpyridin-3-yl]-2,4-pyrimidinediamine (Compound 76)

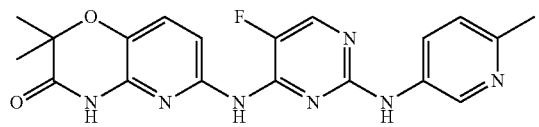 [SMILES: Cc1ccc(Nc2ncc(F)c(Nc3ccc4c(n3)NC(=O)C(C)(C)O4)n2)cn1]

¹H NMR (DMSO-d₆): δ 11.31 (s, 1H), 9.43 (s, 1H), 9.36 (s, 1H), 9.04 (s, 1H), 8.13 (m, 1H), 7.89 (m, 1H), 7.37 (s, 2H), 7.06 (m, 1H), 2.37 (s, 3H), 1.42 (s, 6H); LC-MS: purity: 100.00%; MS (m/e): 396.08 (MH+).

Example 77

N4-(2,2-dimethyl-3,4-dihydro-3-oxo-2H-pyrido[3,2-b][1,4]oxazin-6-yl)-5-fluoro-N2-[4-(4-hydroxypiperidin-1-yl)phenyl]-2,4-pyrimidinediamine (Compound 77)

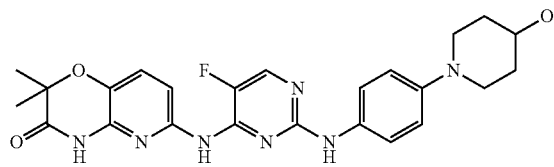

¹H NMR (DMSO-d₆): δ 11.08 (s, 1H), 9.13 (s, 1H), 8.96 (s, 1H), 8.04 (s, 1H), 7.54 (m, 1H), 7.42 (m, 1H), 7.34 (m, 2H), 6.79 (m, 2H), 4.64 (bs, 1H), 3.56 (m, 1H), 3.38 (m, 4H), 2.70 (m, 2H), 1.78 (m, 2H), 1.42 (s, 6H); LC-MS: purity: 100.00%; MS (m/e): 480.29 (MH+).

Example 78

N4-(2,2-dimethyl-3,4-dihydro-3-oxo-2H-pyrido[3,2-b][1,4]oxazin-6-yl)-5-fluoro-N2-[4-(piperidin-1-yl)phenyl]-2,4-pyrimidinediamine (Compound 78)

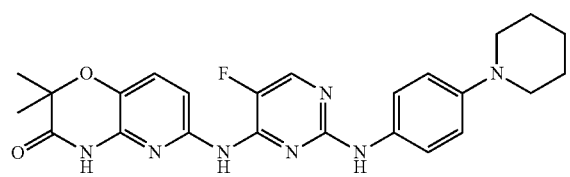 [SMILES: CC1(C)Oc2ccc(Nc3nc(Nc4ccc(N5CCCCC5)cc4)ncc3F)nc2NC1=O]

¹H NMR (DMSO-d₆): δ 11.08 (s, 1H), 9.12 (s, 1H), 8.95 (s, 1H), 8.04 (s, 1H), 7.56 (m, 1H), 7.42 (m, 1H), 7.35 (m, 2H), 6.77 (m, 2H), 2.98 (m, 4H), 1.60 (m, 4H), 1.48 (m, 2H), 1.42 (s, 6H); LC-MS: purity: 100.00%; MS (m/e): 464.08 (MH+).

Example 79

N4-(2,2-dimethyl-3,4-dihydro-3-oxo-2H-pyrido[3,2-b][1,4]oxazin-6-yl)-5-fluoro-N2-1-2,4-pyrimidinediamine (Compound 79)

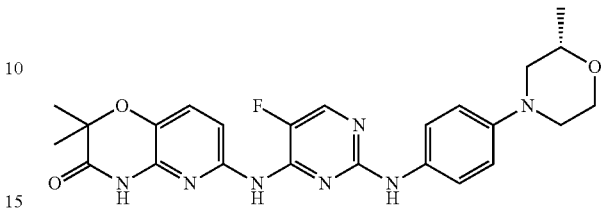

¹H NMR (DMSO-d₆): δ 11.12 (s, 1H), 9.31 (bs, 1H), 9.12 (s, 1H), 8.08 (m, 1H), 7.47 (m, 3H), 7.37 (m, 1H), 6.83 (m, 2H), 3.87 (m, 1H), 3.61 (m, 2H), 3.41 (m, 2H), 2.57 (m, 1H), 2.25 (m, 1H), 1.42 (s, 6H), 1.12 (d, J=6.3 Hz, 3H); LC-MS: purity: 100.00%; MS (m/e): 480.22 (MH+).

Example 80

N4-(3,4-dihydro-3-oxo-2H-pyrido[3,2-b][1,4]oxazin-6-yl)-5-fluoro-N2-[6-((2S)-2-methylmorpholino)phenyl]-2,4-pyrimidinediamine (Compound 80)

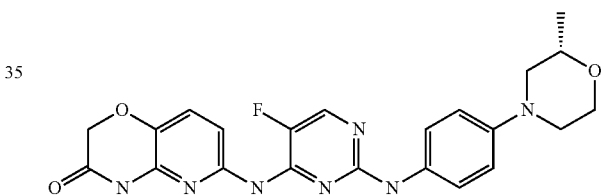

¹H NMR (DMSO-d₆): δ 11.14 (s, 1H), 9.13 (bs, 1H), 8.98 (s, 1H), 8.06 (m, 1H), 7.57 (m, 1H), 7.46 (m, 2H), 7.35 (m, 1H), 6.81 (m, 2H), 4.61 (s, 2H), 3.87 (m, 1H), 3.61 (m, 2H), 3.41 (m, 2H), 2.54 (m, 1H), 2.22 (m, 1H), 1.12 (d, J=6.3 Hz, 3H); LC-MS: purity: 100.00%; MS (m/e): 452.21 (MH+).

Example 81

N4-(2,2-dimethyl-3,4-dihydro-3-oxo-2H-pyrido[3,2-b][1,4]oxazin-6-yl)-5-fluoro-N2-[6-((3R)-2-methylmorpholino)phenyl]-2,4-pyrimidinediamine (Compound 81)

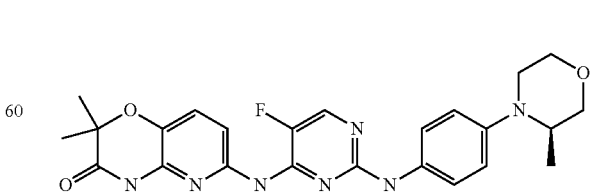

¹H NMR (DMSO-d₆): δ 11.06 (s, 1H), 9.18 (s, 1H), 9.05 (s, 1H), 8.14 (s, 1H), 7.59 (m, 1H), 7.44 (m, 2H), 7.36 (m, 1H), 6.77 (m, 2H), 3.83-3.49 (m, 5H), 2.96 (m, 2H), 1.42 (s, 6H), 0.88 (d, J=6.0 Hz, 3H); LC-MS: purity: 100.00%; MS (m/e): 479.87 (MH+).

Example 82

N4-(3,4-dihydro-3-oxo-2H-pyrido[3,2-b][1,4]oxazin-6-yl)-5-fluoro-N2-[6-((3R)-2-methylmorpholino)phenyl]-2,4-pyrimidinediamine (Compound 82)

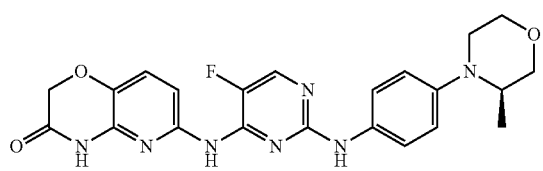 [SMILES: C[C@@H]1COCCN1c1ccc(Nc2ncc(F)c(Nc3ccc4c(n3)NC(=O)CO4)n2)cc1]

$^1$H NMR (DMSO-$d_6$): δ 11.12 (s, 1H), 9.13 (s, 1H), 8.98 (s, 1H), 8.05 (s, 1H), 7.59 (m, 1H), 7.44 (m, 2H), 7.32 (m, 1H), 6.79 (m, 2H), 4.61 (s, 2H), 3.84-3.53 (m, 5H), 2.94 (m, 2H), 0.89 (d, J=6.3 Hz, 3H); LC-MS: purity: 100.00%; MS (m/e): 451.98 (MH+).

Example 83

N4-(3,4-dihydro-3-oxo-2H-pyrido[3,2-b][1,4]oxazin-6-yl)-5-fluoro-N2-[4-(piperidin-1-yl)phenyl]-2,4-pyrimidinediamine (Compound 83)

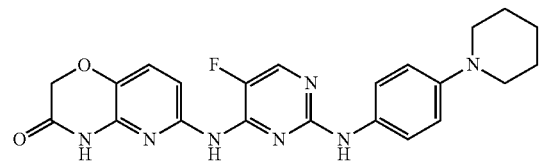 [SMILES: O=C1COc2ccc(Nc3nc(Nc4ccc(N5CCCCC5)cc4)ncc3F)nc2N1]

$^1$H NMR (DMSO-$d_6$): δ 11.06 (s, 1H), 9.09 (s, 1H), 8.94 (s, 1H), 8.34 (s, 1H), 8.04 (m, 1H), 7.83 (m, 1H), 7.43 (m, 1H), 7.34 (m, 1H), 6.79 (m, 2H), 4.61 (s, 2H), 2.98 (m, 4H), 1.60 (m, 4H), 1.48 (m, 2H); LC-MS: purity: 100.00%; MS (m/e): 436.06 (MH+).

Example 84

N4-(3,4-dihydro-3-oxo-2H-pyrido[3,2-b][1,4]oxazin-6-yl)-5-fluoro-N2-[1,2,4a,5-tetrahydro-4H-[1,4]oxazino[3,4-c][1,4]benzoxazin-8-yl]-2,4-pyrimidinediamine (Compound 84)

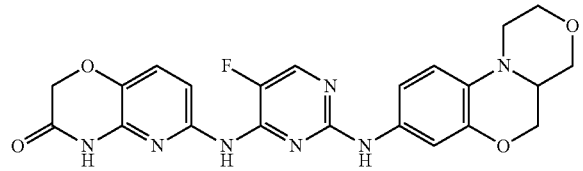 [SMILES: O=C1COc2ccc(Nc3nc(Nc4ccc5c(c4)OCC4COCCN54)ncc3F)nc2N1]

$^1$H NMR (CD$_3$OD): δ 8.50 (s, 1H), 7.98 (m, 1H), 7.83 (m, 1H), 7.18 (m, 1H), 7.13 (m, 1H), 6.86 (m, 1H), 6.78 (m, 1H), 6.71 (m, 1H), 4.58 (s, 2H), 4.46 (m, 1H), 4.24-3.52 (m, 8H); LC-MS: purity: 100.00%; MS (m/e): 466.02 (MH+).

Example 85

N4-(2,2-dimethyl-3,4-dihydro-3-oxo-2H-pyrido[3,2-b][1,4]oxazin-6-yl)-5-fluoro-N2-[4-(4-ethoxypiperidin-1-yl)phenyl]-2,4-pyrimidinediamine (Compound 85)

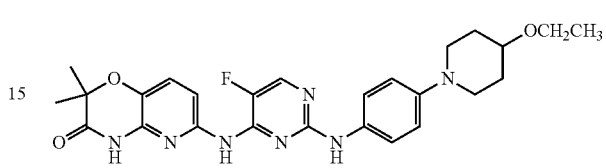

$^1$H NMR (DMSO-$d_6$): δ 11.08 (s, 1H), 9.18 (m, 1H), 9.02 (m, 1H), 8.07 (s, 1H), 7.58-7.32 (m, 4H), 6.81 (m, 2H), 3.47 (q, d=6.9 Hz, 2H), 3.33 (m, 3H), 2.73 (m, 2H), 1.86 (m, 2H), 1.49 (m, 2H), 1.42 (s, 6H), 1.10 (t, J=6.9 Hz, 3H); LC-MS: purity: 100.00%; MS (m/e): 508.11 (MH+).

Example 86

N4-(2,2-dimethyl-3,4-dihydro-3-oxo-2H-pyrido[3,2-b][1,4]oxazin-6-yl)-5-fluoro-N2-[4-(4-isopropoxypiperidin-1-yl)phenyl]-2,4-pyrimidinediamine (Compound 86)

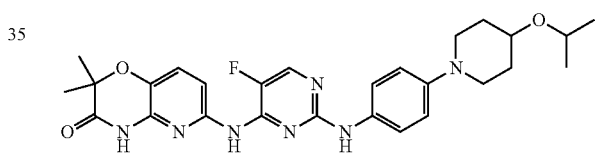

$^1$H NMR (DMSO-$d_6$): δ 11.12 (s, 1H), 9.49 (m, 2H), 8.14 (m, 1H), 7.68 (m, 2H), 7.48 (m, 1H), 7.41 (m, 1H), 7.32 (m, 2H), 3.71 (m, 2H), 3.49 (m, 3H), 2.06 (m, 3H), 1.78 (m, 2H), 1.43 (s, 6H), 1.10 (t, J=6.0 Hz, 6H); LC-MS: purity: 100.00%; MS (m/e): 522.06 (MH+).

Example 87

N4-(2,2-dimethyl-3,4-dihydro-3-oxo-2H-pyrido[3,2-b][1,4]oxazin-6-yl)-5-fluoro-N2-[4-(4-morpholinopiperidin-1-yl)phenyl]-2,4-pyrimidinediamine (Compound 87)

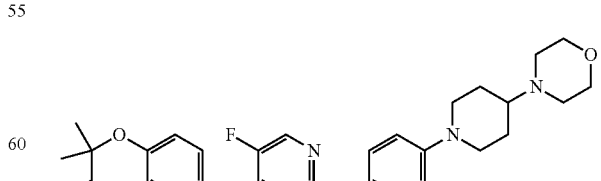

$^1$H NMR (DMSO-$d_6$): δ 11.09 (s, 1H), 10.10 (m, 1H), 9.15 (s, 1H), 9.00 (s, 1H), 8.04 (m, 1H), 7.50-7.34 (m, 3H), 6.81 (m, 2H), 3.96 (m, 1H), 3.72 (m, 3H), 3.43 (m, 2H), 3.09 (m,

2H), 2.58 (m, 5H), 2.14 (m, 2H), 1.63 (m, 2H), 1.42 (s, 6H); LC-MS: purity: 100.00%; MS (m/e): 549.09 (MH+).

Example 88

N4-(2,2-dimethyl-3,4-dihydro-3-oxo-2H-pyrido[3,2-b][1,4]oxazin-6-yl)-5-fluoro-N2-[4-(4-(diethylamino)piperidin-1-yl)phenyl]-2,4-pyrimidinediamine (Compound 88)

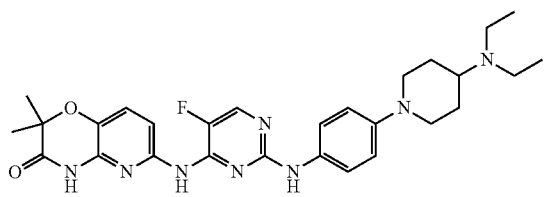 [SMILES: CCN(CC)C1CCN(c2ccc(Nc3ncc(F)c(Nc4ccc5c(n4)NC(=O)C(C)(C)O5)n3)cc2)CC1]

¹H NMR (DMSO-d₆): δ 11.07 (s, 1H), 9.11 (m, 1H), 8.96 (s, 1H), 8.05 (m, 1H), 7.59-7.33 (m, 4H), 6.78 (m, 2H), 3.58 (m, 2H), 2.53 (m, 7H), 1.68 (m, 2H), 1.46 (m, 2H), 1.41 (s, 6H), 0.94 (t, J=6.9 Hz, 6H); LC-MS: purity: 100.00%; MS (m/e): 535.24 (MH+).

Example 89

N4-(2,2-dimethyl-3,4-dihydro-3-oxo-2H-pyrido[3,2-b][1,4]oxazin-6-yl)-5-fluoro-N2-[3-fluoro-4-(3-(hydroxymethyl)morpholino)phenyl]-2,4-pyrimidinediamine (Compound 89)

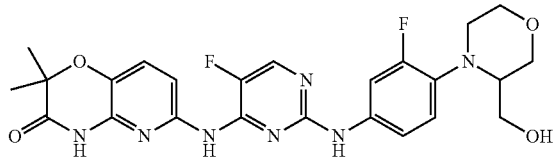 [SMILES: CC1(C)Oc2ccc(Nc3nc(Nc4ccc(N5CCOCC5CO)c(F)c4)ncc3F)nc2NC1=O]

¹H NMR (DMSO-d₆): δ 11.10 (s, 1H), 9.32 (m, 2H), 8.12 (m, 1H), 7.60 (m, 1H), 7.49 (m, 1H), 7.37 (m, 1H), 7.25 (m, 1H), 6.96 (m, 1H), 3.76-3.59 (m, 4H), 3.41 (t, J=9.6 Hz, 2H), 3.21-3.03 (m, 3H), 2.76 (m, 1H), 1.42 (s, 6H); LC-MS: purity: 100.00%; MS (m/e): 549.09 (MH+).

Example 90

N4-(2,2-dimethyl-3,4-dihydro-3-oxo-2H-pyrido[3,2-b][1,4]oxazin-6-yl)-5-fluoro-N2-[4-(4-aminopiperidin-1-yl)phenyl]-2,4-pyrimidinediamine (Compound 90)

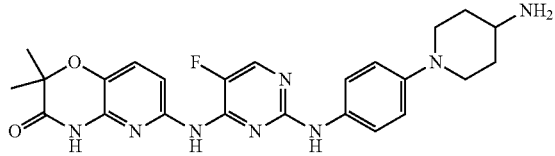 [SMILES: CC1(C)Oc2ccc(Nc3nc(Nc4ccc(N5CCC(N)CC5)cc4)ncc3F)nc2NC1=O]

¹H NMR (CD₃OD): δ 8.35 (s, 1H), 7.92 (m, 1H), 7.86 (m, 1H), 7.41 (m, 2H), 7.16 (m, 1H), 6.95 (m, 2H), 3.66 (m, 2H), 3.17 (m, 1H), 2.77 (m, 2H), 2.09 (m, 2H), 1.79 (m, 2H), 1.49 (s, 6H); LC-MS: purity: 100.00%; MS (m/e): 549.09 (MH+).

Example 91

N4-(2,2-dimethyl-3,4-dihydro-3-oxo-2H-pyrido[3,2-b][1,4]oxazin-6-yl)-5-fluoro-N2-[4-(2-oxooxazolidin-3-yl)phenyl]-2,4-pyrimidinediamine (Compound 91)

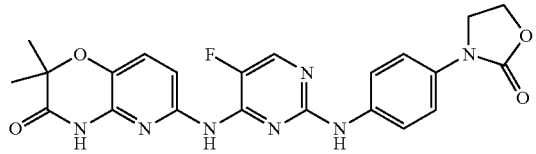 [SMILES: CC1(C)Oc2ccc(Nc3nc(Nc4ccc(N5CCOC5=O)cc4)ncc3F)nc2NC1=O]

¹H NMR (DMSO-d₆): δ 11.09 (s, 1H), 8.25 (s, 2H), 8.11 (m, 1H), 7.63 (m, 2H), 7.53 (m, 1H), 7.35 (m, 3H), 4.39 (t, J=7.5 Hz, 2H), 3.98 (t, J=7.5 Hz, 2H), 1.42 (s, 6H); LC-MS: purity: 100.00%; MS (m/e): 466.12 (MH+).

Example 92

N4-(2,2-dimethyl-3,4-dihydro-3-oxo-2H-pyrido[3,2-b][1,4]oxazin-6-yl)-5-fluoro-N2-[6-((1S,4S)-5-oxa-2-aza-bicyclo[2.2.1]heptan-2-yl)pyridin-3-yl]-2,4-pyrimidinediamine (Compound 92)

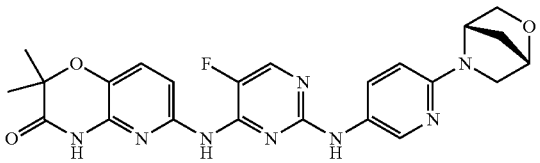 [SMILES: CC1(C)Oc2ccc(Nc3nc(Nc4ccc(N5C[C@@H]6C[C@H]5CO6)nc4)ncc3F)nc2NC1=O]

¹H NMR (DMSO-d₆): d 11.02 (s, 1H), 9.19 (s, 1H), 8.93 (s, 1H), 8.35 (s, 1H), 8.05 (d, 1H, J=3.5 Hz), 7.75 (dd, 1H, J=2.4 and 8.8 Hz), 7.45 (d, 1H, J=8.8 Hz), 7.32 (d, 1H, J=8.8 Hz), 6.44 (d, 1H, J=8.8 Hz), 4.75 (s, 1H), 4.59 (s, 1H), 3.73 (d, 1H, J=7.0 Hz), 3.59 (d, 1H, J=7.3 Hz), 3.41 (d, 1H, J=9.3 Hz), 3.14 (d, 1H, J=9.3 Hz), 1.87 (d, 1H, J=9.7 Hz), 1.80 (d, 1H, J=9.4 Hz); LCMS: purity: 99%; MS (m/e): 479 (MH⁺)

Example 93

N4-(3,4-dihydro-3-oxo-2H-pyrido[3,2-b][1,4]oxazin-6-yl)-5-fluoro-N2-[6-((2S)-2-methylmorpholino)pyridin-3-yl]-2,4-pyrimidinediamine (Compound 93)

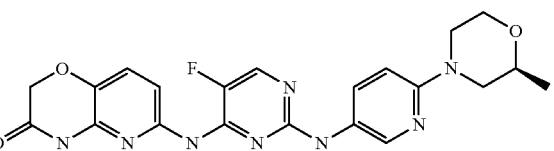

¹H NMR (DMSO-d₆): d 11.10 (s, 1H), 9.41 (s, 1H), 9.25 (s, 1H), 8.46 (d, 1H, J=2.0 Hz), 8.11 (d, 1H, J=3.8 Hz), 7.94 (d, 1H, J=8.8 Hz), 7.44 (d, 1H, J=8.8 Hz), 7.35 (d, 1H, J=8.5 Hz), 6.96 (d, 1H, J=8.5 Hz), 4.62 (s, 2H), 4.01 (d, 1H, J=11.5 Hz), 3.89 (d, 2H, J=11.5 Hz), 3.58-3.31 (m, 2H), 2.86-2.78 (m, 1H), 2.39 (t, 1H, J=11.2 Hz), 1.13 (d, 3H, J=6.3 Hz); LCMS: purity: 98%; MS (m/e): 453 (MH⁺)

Example 94

N4-(2,2-dimethyl-3,4-dihydro-3-oxo-2H-pyrido[3,2-b][1,4]oxazin-6-yl)-5-fluoro-N2-[6-((2S)-2-methyl-morpholino)pyridin-3-yl]-2,4-pyrimidinediamine (Compound 94)

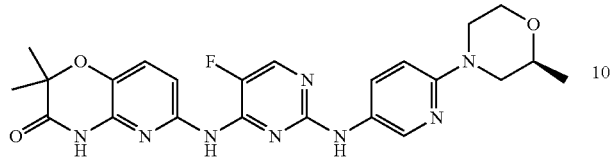

$^1$H NMR (DMSO-d$_6$): d 11.02 (s, 1H), 9.23 (s, 1H), 9.04 (s, 1H), 8.43 (d, 1H, J=2.0 Hz), 8.07 (d, 1H, J=3.5 Hz), 7.85 (d, 1H, J=9.1 Hz), 7.44 (d, 1H, J=8.5 Hz), 7.34 (d, 1H, J=8.5 Hz), 6.74 (d, 1H, J=9.1 Hz), 3.98 (d, 1H, J=11.2 Hz), 3.88 (d, 2H, J=11.2 Hz), 3.54 (app t, 2H), 2.71-2.64 (m, 1H), 2.35 (t, 1H, J=11.2 Hz), 1.41 (s, 6H), 1.14 (d, 3H, J=6.3 Hz); LCMS: purity: 99%; MS (m/e): 481 (MH$^+$)

Example 95 rac-Cis-N4-(3,4-dihydro-3-oxo-2H-pyrido[3,2-b][1,4]oxazin-6-yl)-N2-[6-(2,6-dimethylmorpholino)pyridin-3-yl]-5-fluoro-2,4-pyrimidinediamine (Compound 95)

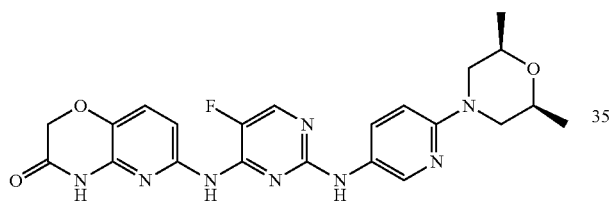

$^1$H NMR (DMSO-d$_6$): d 11.07 (s, 1H), 9.26 (s, 1H), 9.04 (s, 1H), 8.46 (d, 1H, J=2.2 Hz), 8.07 (d, 1H, J=3.5 Hz), 7.83 (d, 1H, J=2.2 and 9.1 Hz), 7.44 (d, 1H, J=8.5 Hz), 7.33 (d, 1H, J=8.5 Hz), 6.77 (d, 1H, J=9.1 Hz), 4.61 (s, 2H), 4.00 (d, 2H, J=11.1 Hz), 3.63-3.54 (m, 2H), 2.29 (t, 2H, J=11.1 Hz), 1.14 (d, 6H, J=6.2 Hz); LCMS: purity: 94%; MS (m/e): 467 (MH$^+$)

Example 96 rac-Cis-N4-(2,2-dimethyl-3,4-dihydro-3-oxo-2H-pyrido[3,2-b][1,4]oxazin-6-yl)-N2-[6-(2,6-dimethyl-morpholino)pyridin-3-yl]-5-fluoro-2,4-pyrimidinediamine (Compound 96)

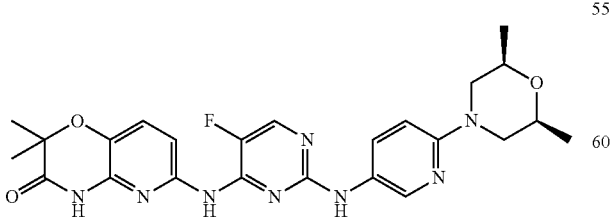

$^1$H NMR (DMSO-d$_6$): d 11.03 (s, 1H), 9.25 (s, 1H), 9.02 (s, 1H), 8.43 (d, 1H, J=2.3 Hz), 8.06 (d, 1H, J=3.5 Hz), 7.83 (dd, 1H, J=2.3 and 9.1 Hz), 7.42 (d, 1H, J=8.5 Hz), 7.34 (d, 1H, J=8.5 Hz), 6.72 (d, 1H, J=9.1 Hz), 3.99 (d, 2H, J=11.1 Hz), 3.61-3.54 (m, 2H), 2.26 (t, 2H, J=11.1 Hz), 1.41 (s, 6H), 1.14 (d, 3H, J=6.3 Hz); LCMS: purity: 94%; MS (m/e): 495 (MH$^+$)

Example 97

N4-(2,2-dimethyl-3,4-dihydro-4-[(dihydrogen phosphonoxy)methyl]-3-oxo-2H-pyrido[3,2-b][1,4]oxazin-6-yl)-5-fluoro-N2-[6-((3S)-3-methylmor-pholino)pyridin-3-yl]-2,4-pyrimidinediamine disodium salt (Compound 97)

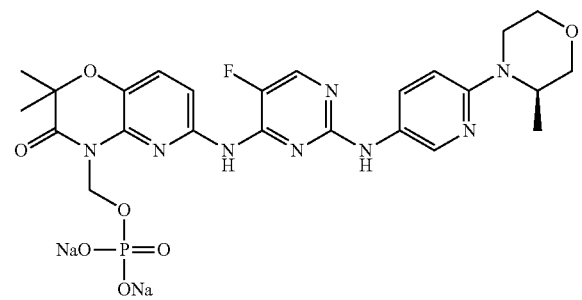

$^1$H NMR (D$_2$O): d 7.80 (d, 1H, J=2.3 Hz), 7.60 (d, 1H, J=3.8 Hz), 7.33 (dd, 1H, J=2.3 and 9.3 Hz), 7.27 (d, 1H, J=8.5 Hz), 6.75 (d, 1H, J=8.5 Hz), 6.44 (d, 1H, J=9.3 Hz), 5.46 (app s, 2H), 3.87 (d, 2H, J=8.6 Hz), 3.63 (app s, 2H), 3.46 (t, 1H, J=11.2 Hz), 3.50 (app t, 2H, J=11.2 Hz), 3.24 (d, 1H, J=11.2 Hz), 2.93 (app t, 1H, J=8.5 Hz), 1.29 (s, 6H), 0.87 (d, 3H, J=6.7 Hz). LCMS: purity: 99%; MS (m/e): 591 (MH+−2Na+2H)

Example 98

N4-(3,4-dihydro-3-oxo-2H-pyrido[3,2-b][1,4]oxazin-6-yl)-5-fluoro-N2-[6-(2-methoxyethyl)methylamino)pyridin-3-yl]-2,4-pyrimidinediamine (Compound 98)

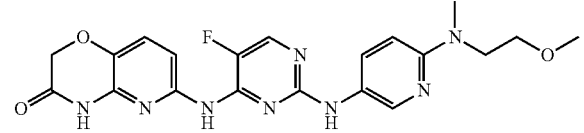 [SMILES: COCCN(C)c1ccc(Nc2ncc(F)c(Nc3ccc4c(n3)NC(=O)CO4)n2)cn1]

$^1$H NMR (DMSO-d$_6$): d 11.09 (s, 1H), 9.15 (s, 1H), 8.87 (s, 1H), 8.23 (d, 1H, J=2.0 Hz), 8.03 (d, 1H, J=3.5 Hz), 7.70 (d, 1H, J=2.0 and 9.1 Hz), 7.44 (d, 1H, J=8.8 Hz), 7.35 (d, 1H, J=8.2 Hz), 8.29 (d, 1H, J=8.2 Hz), 6.53 (d, 1H, J=9.1 Hz), 4.60 (s, 2H), 3.62 (t, 2H, J=5.8; H), 3.45 (t, 2H, J=5.8 Hz), 3.22 (s, 3H), 2.95 (s, 3H); LCMS: purity: 99%; MS (m/e): 441 (MH$^+$)

Example 99

N4-(2,2-dimethyl-3,4-dihydro-3-oxo-2H-pyrido[3,2-b][1,4]oxazin-6-yl)-5-fluoro-N2-[6-(2-methoxy-ethyl)methylamino)pyridin-3-yl]-2,4-pyrimidinediamine (Compound 99)

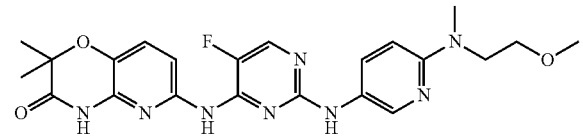 [SMILES: COCCN(C)c1ccc(Nc2ncc(F)c(Nc3ccc4c(n3)NC(=O)C(C)(C)O4)n2)cn1]

¹H NMR (DMSO-d₆): d 11.11 (s, 1H), 9.46 (s, 1H), 9.45 (s, 1H), 8.36 (d, 1H, J=2.0 Hz), 8.16 (d, 1H, J=3.5 Hz), 8.12 (d, 1H, J=9.1 Hz), 7.53 (d, 1H, J=8.5 Hz), 7.39 (d, 1H, J=8.5 Hz), 7.20 (d, 1H, J=9.1 Hz), 3.71 (t, 2H, J=5.8; H), 3.52 (t, 2H, J=5.8 Hz), 3.23 (s, 3H), 3.12 (s, 3H), 1.41 (s, 6H); LCMS: purity: 99%; MS (m/e): 469 (MH⁺)

Example 100

N4-(3,4-dihydro-3-oxo-2H-pyrido[3,2-b][1,4]oxazin-6-yl)-N2-[6-(((2S)-2-ethoxymethyl)morpholino)pyridin-3-yl]-5-fluoro-2,4-pyrimidinediamine (Compound 100)

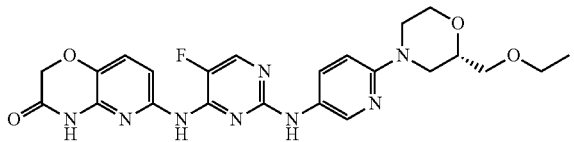 [SMILES: CCOC[C@@H]1CN(c2ccc(Nc3ncc(F)c(Nc4ccc5c(n4)NC(=O)CO5)n3)cn2)CCO1]

¹H NMR (DMSO-d₆): d 11.09 (s, 1H), 9.24 (s, 1H), 9.04 (s, 1H), 8.44 (d, 1H, J=2.0 Hz), 8.06 (dd, 1H, J=3.5 Hz), 7.83 (dd, 1H, J=2.3 and 9.1 Hz), 7.44 (d, 1H, J=8.5 Hz), 7.33 (d, 1H, J=8.5 Hz), 6.74 (d, 1H, J=9.1 Hz), 4.61 (s, 2H), 4.01 (d, 1H, J=11.7 Hz), 3.88 (app t, 2H, J=12.1 Hz), 3.59-3.41 (m, 6H), 2.71 (app t, 1H, J=11.7 Hz), 2.42 (d, 1H, J=11.7 Hz), 1.10 (t, 3H, J=7.0 Hz); LCMS: purity: 99%; MS (m/e): 497 (MH⁺)

Example 101

N4-(2,2-dimethyl-3,4-dihydro-3-oxo-2H-pyrido[3,2-b][1,4]oxazin-6-yl)-N2-[6-(((2S)-2-ethoxymethyl)morpholino)pyridin-3-yl]-5-fluoro-2,4-pyrimidinediamine (Compound 101)

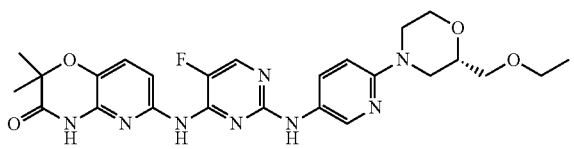 [SMILES: CCOC[C@@H]1CN(c2ccc(Nc3ncc(F)c(Nc4ccc5c(n4)NC(=O)C(C)(C)O5)n3)cn2)CCO1]

¹H NMR (DMSO-d₆): d 11.05 (s, 1H), 9.24 (s, 1H), 9.05 (s, 1H), 8.44 (d, 1H, J=2.0 Hz), 8.07 (d, 1H, J=3.5 Hz), 7.85 (dd, 1H, J=2.0 and 9.1 Hz), 7.44 (d, 1H, J=8.5 Hz), 7.33 (d, 1H, J=8.5 Hz), 6.72 (d, 1H, J=9.1 Hz), 4.01 (d, 1H, J=12.3 Hz), 3.88 (app t, 2H, J=12.3 Hz), 3.61-3.41 (m, 6H), 2.71 (app t, 1H, J=11.7 Hz), 2.43 (d, 1H, J=11.7 Hz), 1.41 (s, 6H), 1.10 (t, 3H, J=7.0 Hz); LCMS: purity: 99%; MS (m/e): 525 (MH⁺)

Example 102

N4-(3,4-dihydro-3-oxo-2H-pyrido[3,2-b][1,4]oxazin-6-yl)-N2-[6-(((2R)-2-ethoxymethyl)morpholino)pyridin-3-yl]-5-fluoro-2,4-pyrimidinediamine (Compound 102)

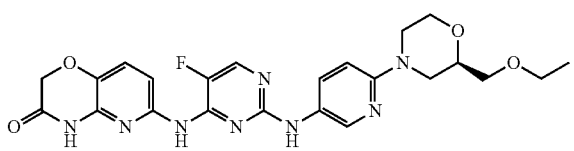 [SMILES: CCOC[C@H]1CN(c2ccc(Nc3ncc(F)c(Nc4ccc5c(n4)NC(=O)CO5)n3)cn2)CCO1]

¹H NMR (DMSO-d₆): d 11.09 (s, 1H), 9.24 (s, 1H), 9.04 (s, 1H), 8.44 (d, 1H, J=1.7 Hz), 8.06 (dd, 1H, J=3.5 Hz), 7.83 (dd, 1H, J=2.3 and 9.1 Hz), 7.44 (d, 1H, J=8.5 Hz), 7.33 (d, 1H, J=8.5 Hz), 6.74 (d, 1H, J=9.1 Hz), 4.61 (s, 2H), 4.01 (d, 1H, J=11.7 Hz), 3.88 (app t, 2H, J=12.1 Hz), 3.59-3.41 (m, 6H), 2.71 (app t, 1H, J=11.7 Hz), 2.42 (d, 1H, J=11.7 Hz), 1.10 (t, 3H, J=7.0 Hz); LCMS: purity: 99%; MS (m/e): 497 (MH⁺)

Example 103

N4-(2,2-dimethyl-3,4-dihydro-3-oxo-2H-pyrido[3,2-b][1,4]oxazin-6-yl)-N2-[6-(((2R)-2-ethoxymethyl)morpholino)pyridin-3-yl]-5-fluoro-2,4-pyrimidinediamine (Compound 103)

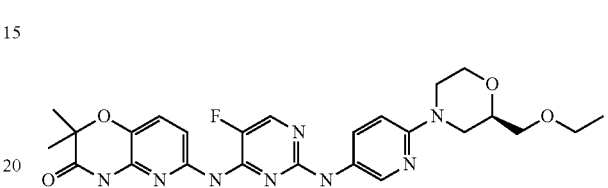

¹H NMR (DMSO-d₆): d 11.05 (s, 1H), 9.24 (s, 1H), 9.05 (s, 1H), 8.44 (d, 1H, J=2.0 Hz), 8.07 (d, 1H, J=3.5 Hz), 7.85 (dd, 1H, J=2.0 and 9.1 Hz), 7.44 (d, 1H, J=8.5 Hz), 7.33 (d, 1H, J=8.5 Hz), 6.72 (d, 1H, J=9.1 Hz), 4.01 (d, 1H, J=12.3 Hz), 3.88 (app t, 2H, J=12.3 Hz), 3.61-3.41 (m, 6H), 2.71 (app t, 1H, J=11.7 Hz), 2.43 (d, 1H, J=11.7 Hz), 1.41 (s, 6H), 1.10 (t, 3H, J=7.0 Hz); LCMS: purity: 99%; MS (m/e): 525 (MH⁺)

Example 104 rac-N4-(3,4-dihydro-3-oxo-2H-pyrido[3,2-b][1,4]oxazin-6-yl)-N2-[6-(2,5-dimethylmorpholino)pyridin-3-yl]-5-fluoro-2,4-pyrimidinediamine (Compound 104)

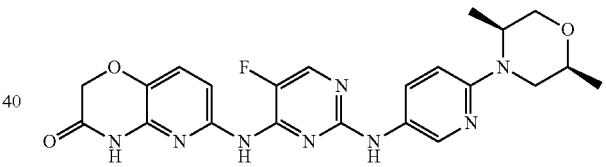

¹H NMR (DMSO-d₆): d 11.11 (s, 1H), 9.27 (s, 1H), 9.09 (s, 1H), 8.46 (s, 1H), 8.07 (d, 1H, J=3.5 Hz), 7.84 (d, 1H, J=9.1 Hz), 7.46 (d, 1H, J=8.5 Hz), 7.32 (d, 1H, J=8.5 Hz), 6.74 (d, 1H, J=9.1 Hz), 4.61 (s, 2H), 3.90-3.85 (m, 2H), 3.74-3.71 (m, 1H), 3.30-3.26 (m, 2H), 3.10-3.04 (m, 1H), 1.14 (d, 3H, J=6.1 Hz), 0.99 (d, 3H, J=6.1 Hz); LCMS: purity: 99%; MS (m/e): 467 (MH⁺)

Example 105 rac-N4-(2,2-dimethyl-3,4-dihydro-3-oxo-2H-pyrido[3,2-b][1,4]oxazin-6-yl)-5-N2-[6-(2,5-dimethylmorpholino)pyridin-3-yl]-5-fluoro-2,4-pyrimidinediamine (Compound 105)

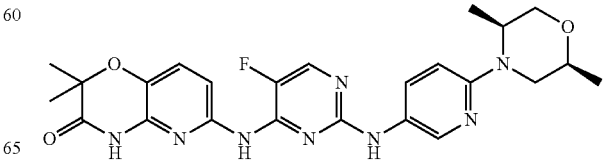

Example 106

N4-(3,4-dihydro-3-oxo-2H-pyrido[3,2-b][1,4]oxazin-6-yl)-5-fluoro-N2-[6-(2,2,3,3,5,5,6,6-d8-morpholino)pyridin-3-yl]-2,4-pyrimidinediamine (Compound 106)

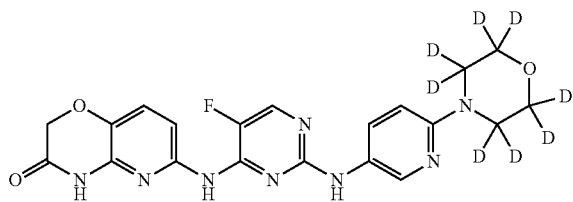 [SMILES: [2H]C1([2H])OC([2H])([2H])C([2H])([2H])N(c2ccc(Nc3ncc(F)c(Nc4ccc5c(n4)NC(=O)CO5)n3)cn2)C1([2H])[2H]]

$^1$H NMR (DMSO-d$_6$): d 11.13 (s, 1H), 9.56 (s, 1H), 9.51 (s, 1H), 8.47 (s, 1H), 8.16 (d, 1H, J=3.5 Hz), 8.07 (d, 1H, J=9.1 Hz), 7.44 (d, 1H, J=8.5 Hz), 7.38 (d, 1H, J=8.5 Hz), 7.15 (d, 1H, J=9.1 Hz), 4.62 (s, 2H); LCMS: purity: 99%; MS (m/e): 447 (MH$^+$)

Example 107

N4-(2,2-dimethyl-3,4-dihydro-3-oxo-2H-pyrido[3,2-b][1,4]oxazin-6-yl)-5-fluoro-N2-[6-(2,2,3,3,5,5,6,6-d8-morpholino)pyridin-3-yl]-2,4-pyrimidinediamine (Compound 107)

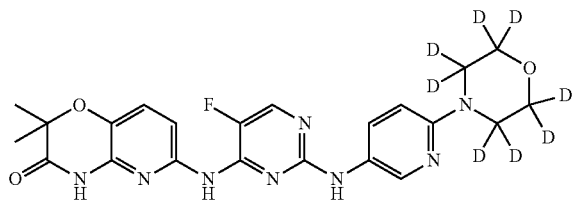 [SMILES: [2H]C1([2H])OC([2H])([2H])C([2H])([2H])N(c2ccc(Nc3ncc(F)c(Nc4ccc5c(n4)NC(=O)C(C)(C)O5)n3)cn2)C1([2H])[2H]]

$^1$H NMR (DMSO-d$_6$): d 11.02 (s, 1H), 9.22 (s, 1H), 9.03 (s, 1H), 8.44 (s, 1H), 8.07 (d, 1H, J=3.5 Hz), 7.83 (d, 1H, J=9.1 Hz), 7.45 (d, 1H, J=8.5 Hz), 7.34 (d, 1H, J=8.5 Hz), 6.73 (d, 1H, J=9.1 Hz), 1.41 (s, 6H); LCMS: purity: 99%; MS (m/e): 475 (MH$^+$)

Example 108

N4-(3,4-dihydro-3-oxo-2H-pyrido[3,2-b][1,4]oxazin-6-yl)-5-fluoro-N2-[6-(((S)-methyl(tetrahydrofuran-2-yl)methyl)amino)pyridin-3-yl]-2,4-pyrimidinediamine (Compound 108)

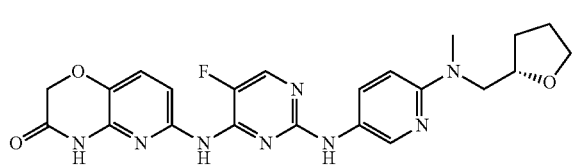 [SMILES: CN(C[C@@H]1CCCO1)c1ccc(Nc2ncc(F)c(Nc3ccc4c(n3)NC(=O)CO4)n2)cn1]

$^1$H NMR (DMSO-d$_6$): d 11.16 (s, 1H), 9.27 (s, 1H), 9.09 (s, 1H), 8.44 (d, 1H, J=2.3 Hz), 8.07 (d, 1H, J=3.5 Hz), 7.86 (dd, 1H, J=2.3 and 9.1 Hz), 7.45 (d, 1H, J=8.5 Hz), 7.33 (d, 1H, J=8.5 Hz), 6.74 (d, 1H, J=9.1 Hz), 3.90-3.85 (m, 2H), 3.71-3.68 (m, 1H), 3.30-3.26 (m, 2H), 3.08-3.02 (m, 1H), 1.41 (s, 6H), 1.13 (d, 3H, J=6.1 Hz), 0.99 (d, 3H, J=6.1 Hz); LCMS: purity: 99%; MS (m/e): 495 (MH$^+$)

Example 109

N4-(2,2-dimethyl-3,4-dihydro-3-oxo-2H-pyrido[3,2-b][1,4]oxazin-6-yl)-5-fluoro-N2-[6-(((S)-methyl(tetrahydrofuran-2-yl)methyl)amino)pyridin-3-yl]-2,4-pyrimidinediamine (Compound 109)

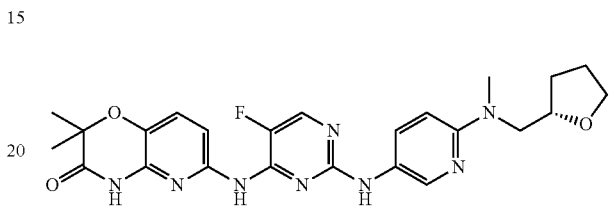

$^1$H NMR (DMSO-d$_6$): d 11.10 (s, 1H), 9.40 (s, 1H), 9.30 (s, 1H), 8.34 (s, 1H), 8.14 (d, 1H, J=3.5 Hz), 8.05 (d, 1H, J=9.1 Hz), 7.51 (d, 1H, J=8.5 Hz), 7.37 (d, 1H, J=8.5 Hz), 7.10 (d, 1H, J=9.1 Hz), 4.03-3.90 (m, 1H), 3.75 (qt, 1H, J=7.0 Hz), 3.65-3.51 (m, 3H), 3.11 (s, 3H), 1.96-1.76 (m, 3H), 1.52-1.45 (m, 1H), 1.41 (s, 6H); LCMS: purity: 99%; MS (m/e): 467 (MH+)

Example 110

N4-(3,4-dihydro-3-oxo-2H-pyrido[3,2-b][1,4]oxazin-6-yl)-5-fluoro-N2-[6-(((R)-methyl(tetrahydrofuran-2-yl)methyl)amino)pyridin-3-yl]-2,4-pyrimidinediamine (Compound 110)

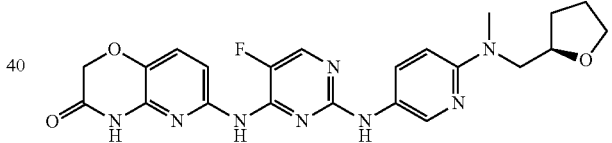

$^1$H NMR (DMSO-d$_6$): d 11.12 (s, 1H), 9.24 (s, 1H), 9.04 (s, 1H), 8.44 (d, 1H, J=2.0 Hz), 8.06 (d, 1H, J=3.5 Hz), 7.79 (d, 1H, J=8.5 Hz), 7.49 (d, 1H, J=2.3 and 9.1 Hz), 7.33 (d, 1H, J=8.5 Hz), 6.69 (d, 1H, J=9.1 Hz), 4.61 (s, 2H), 4.02-3.90 (m, 1H), 3.75 (qt, 1H, J=7.0 Hz), 3.65-3.42 (m, 3H), 3.01 (s, 3H), 1.92-1.75 (m, 3H), 1.53-1.45 (m, 1H); LCMS: purity: 99%; MS (m/e): 497 (MH+)

Example 111

N4-(2,2-dimethyl-3,4-dihydro-3-oxo-2H-pyrido[3,2-b][1,4]oxazin-6-yl)-5-fluoro-N2-[6-(((R)-methyl(tetrahydrofuran-2-yl)methyl)amino)pyridin-3-yl]-2,4-pyrimidinediamine (Compound 111)

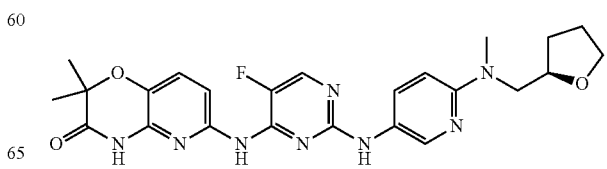

¹H NMR (DMSO-d₆): d 11.10 (s, 1H), 9.40 (s, 1H), 9.30 (s, 1H), 8.34 (s, 1H), 8.14 (d, 1H, J=3.5 Hz), 8.05 (d, 1H, J=9.1 Hz), 7.51 (d, 1H, J=8.5 Hz), 7.37 (d, 1H, J=8.5 Hz), 7.10 (d, 1H, J=9.1 Hz), 4.03-3.90 (m, 1H), 3.75 (qt, 1H, J=7.0 Hz), 3.65-3.51 (m, 3H), 3.11 (s, 3H), 1.96-1.76 (m, 3H), 1.52-1.45 (m, 1H), 1.41 (s, 6H); LCMS: purity: 99%; MS (m/e): 495 (MH+)

Example 112

N4-(2,2-dimethyl-3,4-dihydro-4-[(dihydrogen phosphonoxy)methyl]-3-oxo-2H-pyrido[3,2-b][1,4] oxazin-6-yl)-5-fluoro-N2-(3-methyl-4-morpholinophenyl)-2,4-pyrimidinediamine disodium salt (Compound 112)

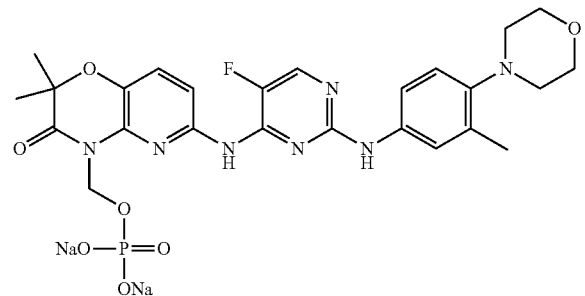

¹H NMR (D₂O): d 7.67 (d, 1H, J=3.5 Hz), 7.42 (d, 1H, J=9.1 Hz), 6.94 (s, 1H), 6.82 (d, 1H, J=8.5 Hz), 6.68 (d, 1H, J=9.1 Hz), 6.44 (d, 1H, J=9.3 Hz), 5.49 (app s, 2H), 3.75 (app s, 4H), 2.71 (app s, 4H), 1.33 (s, 6H). LCMS: purity: 99%; MS (m/e): 590 (MH+−2Na+2H)

Example 113

N4-(2,2-dimethyl-3,4-dihydro-4-[(dihydrogen phosphonoxy)methyl]-3-oxo-2H-pyrido[3,2-b][1,4] oxazin-6-yl)-5-fluoro-N2-(3-fluoro-4-morpholinophenyl)-2,4-pyrimidinediamine disodium salt (Compound 113)

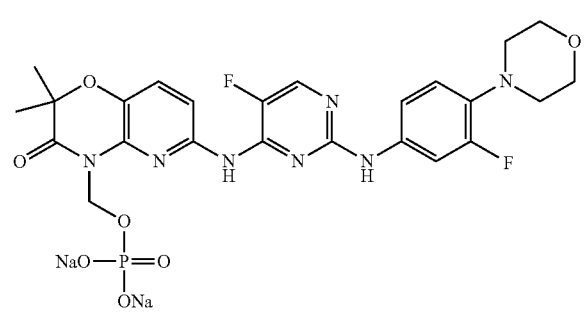

¹H NMR (D₂O): d 7.63 (d, 1H, J=3.5 Hz), 7.32-7.28 (m, 1H), 6.98 (d, 1H, J=12 Hz), 6.74 (d, 1H, J=9.1 Hz), 6.65 (m, 2H), 5.49 (app s, 2H), 3.75 (app s, 4H), 2.81 (app s, 4H), 1.33 (s, 6H). LCMS: purity: 99%; MS (m/e): 594 (MH+−2Na+2H)

Example 114

N4-(3,4-dihydro-4-[(dihydrogen phosphonoxy)methyl]-3-oxo-2H-pyrido[3,2-b][1,4]oxazin-6-yl)-5-fluoro-N2-(4-morpholinophenyl)-2,4-pyrimidinediamine disodium salt (Compound 114)

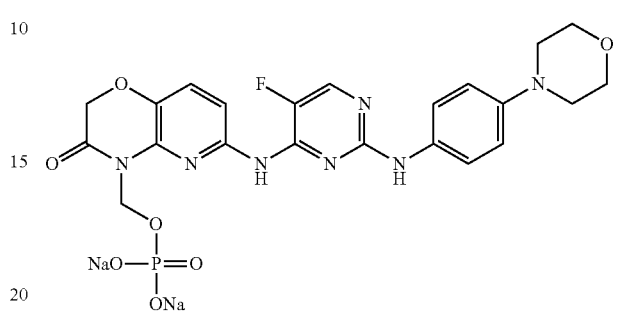

¹H NMR (D₂O): d 7.59 (d, 1H, J=3.5 Hz), 7.29 (d, 1H, J=8.8 Hz), 6.93 (d, 2H, J=8.5 Hz), 6.70 (d, 2H, J=8.5 Hz), 6.64 (d, 1H, J=8.8 Hz), 5.47 (app s, 2H), 4.40 (app s, 2H), 3.73 (app s, 4H), 2.86 (app s, 4H). LCMS: purity: 99%; MS (m/e): 548 (MH+−2Na+2H)

Example 115

N4-(3,4-dihydro-3-oxo-2H-pyrido[3,2-b][1,4]oxazin-6-yl)-N2-[4-(2,2-dimethylmorpholino)phenyl]-5-fluoro-2,4-pyrimidinediamine (Compound 115)

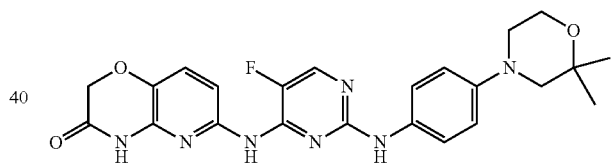

¹H NMR (DMSO-d₆): d 11.12 (s, 1H), 9.11 (s, 1H), 8.97 (s, 1H), 8.06 (d, 1H, J=3.5 Hz), 7.55 (d, 1H, J=8.5 Hz), 7.45 (d, 2H, J=9.1 Hz), 7.34 (d, 1H, J=8.8 Hz), 6.79 (d, 2H, J=9.1 Hz), 4.61 (s, 2H), 3.73-3.70 (m, 2H), 2.93-2.90 (m, 2H), 2.80 (s, 2H), 1.21 (s, 6H); LCMS: purity: 99%; MS (m/e): 466 (MH⁺)

Example 116

N4-(2,2-dimethyl-3,4-dihydro-3-oxo-2H-pyrido[3,2-b][1,4]oxazin-6-yl)-N2-[4-(2,2-dimethylmorpholino)phenyl]-5-fluoro-2,4-pyrimidinediamine (Compound 116)

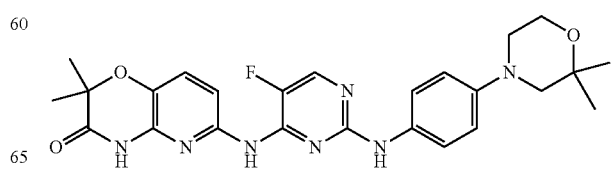

¹H NMR (DMSO-d₆): d 11.09 (s, 1H), 9.15 (s, 1H), 8.98 (s, 1H), 8.06 (d, 1H, J=3.5 Hz), 7.50 (d, 1H, J=8.5 Hz), 7.47 (d, 2H, J=8.8 Hz), 7.37 (d, 1H, J=8.5 Hz), 6.78 (d, 2H, J=8.8 Hz), 3.73-3.70 (m, 2H), 2.92-2.89 (m, 2H), 2.78 (s, 2H), 1.41 (s, 6H), 1.21 (s, 6H); LCMS: purity: 99%; MS (m/e): 494 (MH⁺)

Example 117

N4-(3,4-dihydro-3-oxo-2H-pyrido[3,2-b][1,4]oxazin-6-yl)-5-fluoro-N2-[4-((2R)-2-methylmorpholino)phenyl]-2,4-pyrimidinediamine (Compound 117)

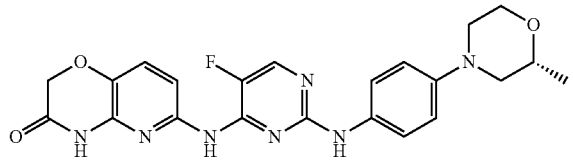 [SMILES: C[C@@H]1CN(c2ccc(Nc3ncc(F)c(Nc4ccc5c(n4)NC(=O)CO5)n3)cc2)CCO1]

¹H NMR (DMSO-d₆): d 11.12 (s, 1H), 9.11 (s, 1H), 8.98 (s, 1H), 8.06 (d, 1H, J=3.5 Hz), 7.57 (d, 1H, J=8.5 Hz), 7.46 (d, 2H, J=8.8 Hz), 7.35 (d, 1H, J=8.5 Hz), 6.81 (d, 2H, J=8.8 Hz), 4.62 (s, 2H), 3.86 (dd, 1H, J=2.1 and 10.5 Hz), 3.64-3.57 (m, 2H), 3.44 (d, 1H, J=11.4 Hz), 3.34 (d, 1H, J=11.4 Hz), 2.55 (dt, 1H, J=2.4 and 11.4 Hz), 2.23 (t, 1H, J=11.4 Hz), 1.12 (d, 2H, J=6.3 Hz); LCMS: purity: 96%; MS (m/e): 452 (MH⁺)

Example 118

N4-(2,2-dimethyl-3,4-dihydro-3-oxo-2H-pyrido[3,2-b][1,4]oxazin-6-yl)-5-fluoro-N2-[4-((2R)-2-methylmorpholino)phenyl]-2,4-pyrimidinediamine (Compound 118)

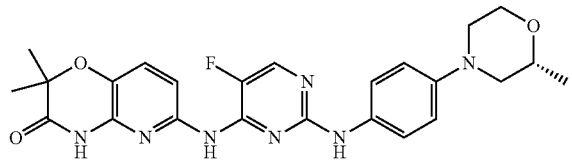

¹H NMR (DMSO-d₆): d 11.08 (s, 1H), 9.13 (s, 1H), 8.99 (s, 1H), 8.06 (d, 1H, J=3.5 Hz), 7.52 (d, 1H, J=8.5 Hz), 7.46 (d, 2H, J=8.8 Hz), 7.36 (d, 1H, J=8.5 Hz), 6.80 (d, 2H, J=8.8 Hz), 3.86 (dd, 1H, J=2.1 and 10.5 Hz), 3.64-3.57 (m, 2H), 3.42 (d, 1H, J=11.4 Hz), 3.34 (d, 1H, J=11.4 Hz), 2.55 (dt, 1H, J=2.4 and 11.4 Hz), 2.22 (t, 1H, J=11.4 Hz), 1.41 (s, 6H), 1.12 (d, 2H, J=6.3 Hz); LCMS: purity: 98%; MS (m/e): 480 (MH⁺)

Example 119

N4-(3,4-dihydro-3-oxo-2H-pyrido[3,2-b][1,4]oxazin-6-yl)-5-fluoro-N2-[4-((3S)-3-methylmorpholino)phenyl]-2,4-pyrimidinediamine (Compound 119)

¹H NMR (DMSO-d₆): d 11.12 (s, 1H), 9.11 (s, 1H), 8.98 (s, 1H), 8.06 (d, 1H, J=3.5 Hz), 7.56 (d, 1H, J=8.2 Hz), 7.46 (d, 2H, J=9.1 Hz), 7.33 (d, 1H, J=8.2 Hz), 6.81 (d, 2H, J=9.1 Hz), 4.61 (s, 2H), 3.84 (d, 1H, J=10.5 Hz), 3.71 (d, 1H, J=10.5 Hz), 3.60 (m, 3H), 2.97-2.91 (m, 2H), 0.89 (d, 2H, J=6.4 Hz); LCMS: purity: 96%; MS (m/e): 452 (MH⁺)

Example 120

N4-(2,2-dimethyl-3,4-dihydro-3-oxo-2H-pyrido[3,2-b][1,4]oxazin-6-yl)-5-fluoro-N2-[4-((3S)-3-methylmorpholino)phenyl]-2,4-pyrimidinediamine (Compound 120)

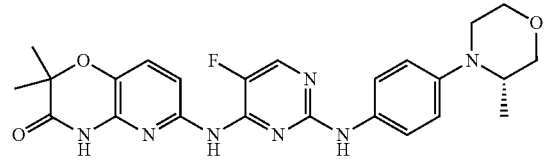 [SMILES: C[C@H]1COCCN1c1ccc(Nc2ncc(F)c(Nc3ccc4c(n3)NC(=O)C(C)(C)O4)n2)cc1]

¹H NMR (DMSO-d₆): d 11.08 (s, 1H), 9.13 (s, 1H), 8.99 (s, 1H), 8.06 (d, 1H, J=3.5 Hz), 7.52 (d, 1H, J=8.5 Hz), 7.46 (d, 2H, J=8.8 Hz), 7.36 (d, 1H, J=8.5 Hz), 6.80 (d, 2H, J=8.8 Hz), 3.84 (d, 1H, J=10.5 Hz), 3.71 (d, 1H, J=10.5 Hz), 3.60 (m, 3H), 2.97-2.91 (m, 2H), 0.89 (d, 2H, J=6.4 Hz), 1.41 (s, 6H), 0.89 (d, 2H, J=6.3 Hz); LCMS: purity: 98%; MS (m/e): 480 (MH⁺)

Example 121 rac-N4-(3,4-dihydro-3-oxo-2H-pyrido[3,2-b][1,4]oxazin-6-yl)-N2-[4-((2-dimethylaminomethyl)morpholino)phenyl]-5-fluoro-2,4-pyrimidinediamine (Compound 121)

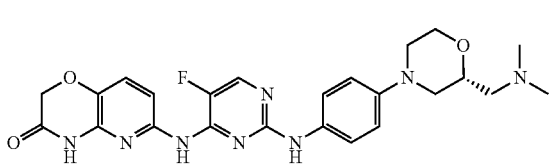 [SMILES: CN(C)C[C@@H]1CN(c2ccc(Nc3ncc(F)c(Nc4ccc5c(n4)NC(=O)CO5)n3)cc2)CCO1]

¹H NMR (DMSO-d₆): d 11.11 (s, 1H), 9.11 (s, 1H), 8.98 (s, 1H), 8.06 (d, 1H, J=3.5 Hz), 7.56 (d, 1H, J=8.5 Hz), 7.46 (d, 2H, J=9.1 Hz), 7.34 (d, 1H, J=8.5 Hz), 6.80 (d, 2H, J=9.1 Hz), 4.61 (s, 2H), 3.89 (d, 1H, J=9.6 Hz), 3.64-3.57 (m, 2H), 3.43 (d, 1H, J=12.3 Hz), 3.35 (d, 1H, J=12.3 Hz), 2.60-2.53 (m, 1H), 2.32-2.28 (m, 3H), 2.16 (s, 6H); LCMS: purity: 95%; MS (m/e): 495 (MH⁺)

Example 122

N4-(2,2-dimethyl-3,4-dihydro-3-oxo-2H-pyrido[3,2-b][1,4]oxazin-6-yl)-N2-[4-((3S)-3-methylmorpholino)phenyl]-5-fluoro-2,4-pyrimidinediamine (Compound 122)

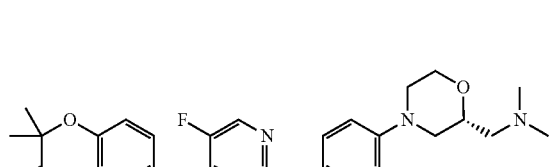

$^1$H NMR (DMSO-d$_6$): d 11.09 (s, 1H), 9.14 (s, 1H), 8.99 (s, 1H), 8.06 (d, 1H, J=3.5 Hz), 7.51 (d, 1H, J=8.5 Hz), 7.47 (d, 2H, J=8.8 Hz), 7.35 (d, 1H, J=8.5 Hz), 6.78 (d, 2H, J=8.8 Hz), 3.89 (d, 1H, J=11.7 Hz), 3.64-3.57 (m, 2H), 3.43 (d, 1H, J=11.4 Hz), 3.35 (d, 1H, J=11.4 Hz), 2.60-2.53 (m, 1H), 2.34-2.24 (m, 3H), 2.16 (s, 6H), 1.42 (s, 6H); LCMS: purity: 95%; MS (m/e): 523 (MH$^+$)

Example 123

5-Fluoro-N2-(4-morpholinophenyl)-N4-(3'-oxo-3',4'-dihydrospiro[cyclobutane-1,2'-pyrido[3,2-b][1,4]oxazine]-6-yl)-2,4-pyrimidinediamine (Compound 123)

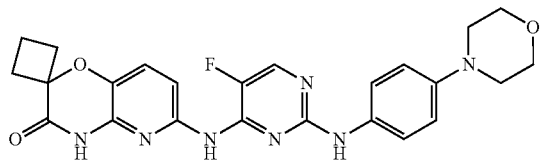 [SMILES: O=C1Nc2nc(Nc3nc(Nc4ccc(N5CCOCC5)cc4)ncc3F)ccc2OC12CCC2]

$^1$H NMR (DMSO-d$_6$): d 11.10 (s, 1H), 9.16 (s, 1H), 9.00 (s, 1H), 8.06 (d, 1H, J=3.2 Hz), 7.53 (d, 1H, J=8.5 Hz), 7.47 (d, 2H, J=9.1 Hz), 7.42 (d, 1H, J=8.5 Hz), 6.81 (d, 2H, J=9.1 Hz), 3.72-3.69 (m. 4H), 3.00-2.97 (m, 4H), 2.50-2.49 (m, 2H), 2.30-2.20 (app qt, 2H, J=9.4 Hz), 1.93-1.77 (m, 2H); LCMS: purity: 92%; MS (m/e): 478 (MH$^+$)

Example 124

N2-[4-(2,2-Dimethylmorpholino)phenyl]-5-fluoro-N4-(3'-oxo-3',4'-dihydrospiro[cyclobutane-1,2'-pyrido[3,2-b][1,4]oxazine]-6-yl)-2,4-pyrimidinediamine (Compound 124)

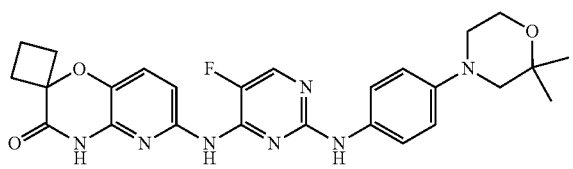 [SMILES: CC1(C)CN(c2ccc(Nc3ncc(F)c(Nc4ccc5c(n4)NC(=O)C4(CCC4)O5)n3)cc2)CCO1]

$^1$H NMR (DMSO-d$_6$): d 11.11 (s, 1H), 9.18 (s, 1H), 8.98 (s, 1H), 8.06 (d, 1H, J=3.2 Hz), 7.47-7.40 (m, 4H), 6.78 (d, 2H, J=8.8 Hz), 3.73-3.70 (m. 4H), 2.91-2.89 (m, 4H), 2.50-2.49 (m, 2H), 2.30-2.20 (app qt, 2H, J=9.4 Hz), 1.93-1.77 (m, 2H), 1.21 (s, 6H); LCMS: purity: 91%; MS (m/e): 506 (MH$^+$)

Example 125

N4-(3,4-dihydro-3-oxo-2H-pyrido[3,2-b][1,4]oxazin-6-yl)-5-fluoro-N2-[4-((2-hydroxyethyl)morpholino)phenyl]-2,4-pyrimidinediamine (Compound 125)

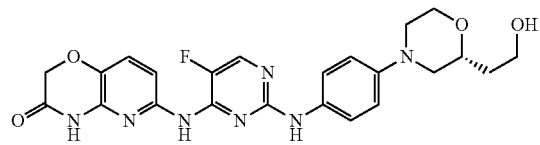 [SMILES: O=C1COc2ccc(Nc3nc(Nc4ccc(N5CCO[C@H](CCO)C5)cc4)ncc3F)nc2N1]

$^1$H NMR (DMSO-d$_6$): d 11.15 (s, 1H), 9.17 (s, 1H), 9.01 (s, 1H), 8.06 (d, 1H, J=3.5 Hz), 7.56 (d, 1H, J=8.5 Hz), 7.46 (d, 2H, J=9.1 Hz), 7.35 (d, 1H, J=8.5 Hz), 6.82 (d, 2H, J=9.1 Hz), 4.61 (s, 2H), 4.46 (t, 1H, J=4.9 Hz), 3.87 (d, 1H, J=11.1 Hz), 3.61-3.37 (m, 6H), 2.56 (t, 1H, J=11.1 Hz), 2.28 (t, 1H, J=11.1 Hz), 1.59 (qt, 2H, J=6.4 Hz); LCMS: purity: 96%; MS (m/e): 482 (MH$^+$)

Example 126

N4-(2,2-dimethyl-3,4-dihydro-3-oxo-2H-pyrido[3,2-b][1,4]oxazin-6-yl)-5-fluoro-N2-[4-((2-hydroxyethyl)morpholino)phenyl]-2,4-pyrimidinediamine (Compound 126)

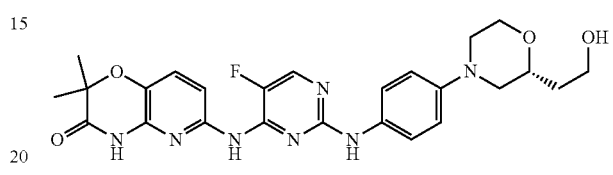

$^1$H NMR (DMSO-d$_6$): d 11.10 (s, 1H), 9.15 (s, 1H), 8.99 (s, 1H), 8.06 (d, 1H, J=3.5 Hz), 7.52 (d, 1H, J=8.5 Hz), 7.46 (d, 2H, J=8.8 Hz), 7.36 (d, 1H, J=8.5 Hz), 6.80 (d, 2H, J=8.8 Hz), 4.46 (t, 1H, J=4.9 Hz), 3.88 (d, 1H, J=11.1 Hz), 3.61-3.38 (m, 6H), 2.54 (t, 1H, J=11.1 Hz), 2.26 (t, 1H, J=11.1 Hz), 1.59 (qt, 2H, J=6.4 Hz), 1.41 (s, 6H); LCMS: purity: 98%; MS (m/e): 510 (MH$^+$)

Example 127

N4-(3,4-dihydro-3-oxo-2H-pyrido[3,2-b][1,4]oxazin-6-yl)-5-fluoro-N2-[4-((2-hydroxymethyl)morpholino)phenyl]-2,4-pyrimidinediamine (Compound 127)

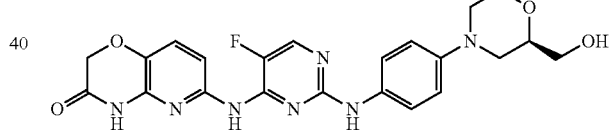

$^1$H NMR (DMSO-d$_6$): d 11.14 (s, 1H), 9.15 (s, 1H), 9.00 (s, 1H), 8.06 (d, 1H, J=3.5 Hz), 7.56 (d, 1H, J=8.5 Hz), 7.46 (d, 2H, J=9.1 Hz), 7.35 (d, 1H, J=8.5 Hz), 6.82 (d, 2H, J=9.1 Hz), 4.74 (br s, 1H), 4.61 (s, 2H), 3.90 (d, 1H, J=11.1 Hz), 3.64-3.38 (m, 5H), 2.56 (t, 1H, J=11.1 Hz), 2.31 (t, 1H, J=11.1 Hz); LCMS: purity: 96%; MS (m/e): 468 (MH$^+$)

Example 128

N4-(2,2-dimethyl-3,4-dihydro-3-oxo-2H-pyrido[3,2-b][1,4]oxazin-6-yl)-5-fluoro-N2-[4-((2-hydroxymethyl)morpholino)phenyl]-2,4-pyrimidinediamine (Compound 128)

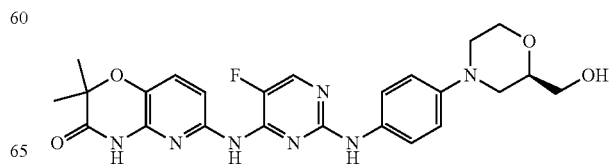

¹H NMR (DMSO-d₆): d 11.10 (s, 1H), 9.15 (s, 1H), 8.99 (s, 1H), 8.06 (d, 1H, J=3.5 Hz), 7.52 (d, 1H, J=8.5 Hz), 7.46 (d, 2H, J=8.8 Hz), 7.36 (d, 1H, J=8.5 Hz), 6.80 (d, 2H, J=8.8 Hz), 4.74 (br s, 1H), 3.90 (d, 1H, J=11.1 Hz), 3.64-3.36 (m, 5H), 2.56 (t, 1H, J=11.1 Hz), 2.30 (t, 1H, J=11.1 Hz), 1.41 (s, 6H); LCMS: purity: 98%; MS (m/e): 496 (MH⁺)

Example 129

N4-(3,4-dihydro-4-[(dihydrogen phosphonoxy)methyl]-3-oxo-2H-pyrido[3,2-b][1,4]oxazin-6-yl)-5-fluoro-N2-[4-(2,2-dimethylmorpholino)phenyl]-2,4-pyrimidinediamine disodium salt (Compound 129)

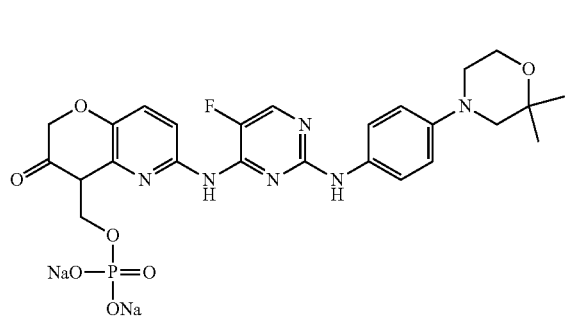

¹H NMR (D₂O): d 7.57 (s, 1H), 7.24 (d, 1H, J=8.2 Hz), 6.87 (d, 2H, J=7.9 Hz), 6.59 (d, 1H, J=8.2 Hz), 6.50 (d, 2H, J=7.9 Hz), 5.44 (s, 2H), 3.71 (s, 2H), 2.75 (s, 2H), 2.63 (s, 2H), 1.16 (s, 6H). LCMS: purity: 99%; MS (m/e): 576 (MH⁺−2Na+2H)

Example 130

N4-(2,2-dimethyl-3,4-dihydro-3-oxo-2H-pyrido[3,2-b][1,4]oxazin-6-yl)-5-fluoro-N2-[4-(2,2,3,3,5,5,6,6-d₈-morpholino)phenyl]-2,4-pyrimidinediamine (Compound 130)

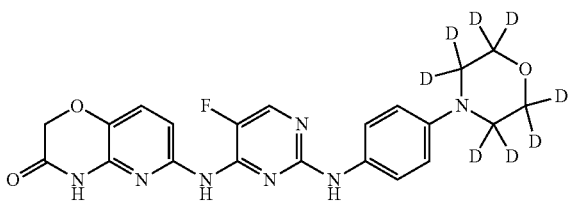 [SMILES: [2H]C1([2H])OC([2H])([2H])C([2H])([2H])N(c2ccc(Nc3ncc(F)c(Nc4ccc5c(n4)NC(=O)CO5)n3)cc2)C1([2H])[2H]]

¹H NMR (DMSO-d₆): d 11.13 (s, 1H), 9.12 (s, 1H), 8.95 (s, 1H), 8.06 (d, 1H, J=3.5 Hz), 7.57 (d, 1H, J=8.5 Hz), 7.46 (d, 2H, J=8.8 Hz), 7.35 (d, 1H, J=8.5 Hz), 6.80 (d, 2H, J=8.8 Hz), 4.62 (s, 2H); LCMS: purity: 97%; MS (m/e): 446 (MH⁺)

Example 131

N4-(2,2-dimethyl-3,4-dihydro-3-oxo-2H-pyrido[3,2-b][1,4]oxazin-6-yl)-5-fluoro-N2-[4-(2,2,3,3,5,5,6,6-d₈-morpholino)phenyl]-2,4-pyrimidinediamine (Compound 131)

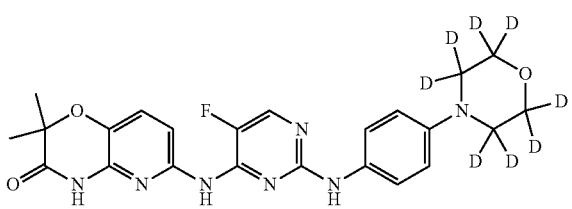 [SMILES: [2H]C1([2H])OC([2H])([2H])C([2H])([2H])N(c2ccc(Nc3ncc(F)c(Nc4ccc5c(n4)NC(=O)C(C)(C)O5)n3)cc2)C1([2H])[2H]]

¹H NMR (DMSO-d₆): d 11.09 (s, 1H), 9.11 (s, 1H), 8.99 (s, 1H), 8.06 (d, 1H, J=3.5 Hz), 7.56 (d, 1H, J=8.5 Hz), 7.46 (d, 2H, J=8.8 Hz), 7.36 (d, 1H, J=8.5 Hz), 6.80 (d, 2H, J=8.8 Hz), 1.41 (s, 6H); LCMS: purity: 93%; MS (m/e): 474 (MH⁺)

Example 132

N4-(2,2-dimethyl-3,4-dihydro-3-oxo-2H-pyrido[3,2-b][1,4]oxazin-6-yl)-5-fluoro-N2-[2-(pyridin-4-yl)-1H-benzo[d]imidazol-6-yl]-2,4-pyrimidinediamine (Compound 132)

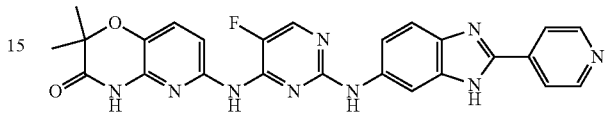

¹H NMR (DMSO-d₆): δ 8.71 (d, 1H, J=5.1 Hz), 8.11 (m, 4H), 7.72 (m, 1H), 7.41 (m, 4H), 1.41 (s, 6H); LCMS: purity: 99%; MS (m/e): 498 (MH⁺)

Example 133

N4-(2,2-dimethyl-3,4-dihydro-3-oxo-2H-pyrido[3,2-b][1,4]oxazin-6-yl)-5-fluoro-N2-(isoquinolin-7-yl)-2,4-pyrimidinediamine (Compound 133)

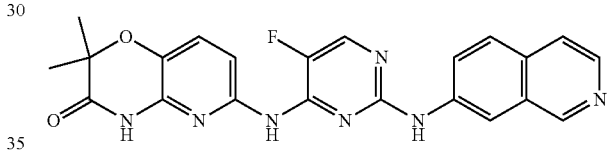

A mixture of 1.6 g 2-chloro-5-fluoro-N4-[2,2-dimethyl-3,4-dihydro-3-oxo-pyrido[3,2-b][1,4]oxazin-6-yl]-4-pyrimidineamine, 800 mg of 7-aminoisoquinoline, 320 mg of palladium acetate, 320 mg of rac-Binap and 3.68 g cesium carbonate in 32 mL of 1,4-dioxane and 8 mL of NMP was heated at reflux at 100° C. overnight under argon. The reaction was cooled, diluted with CH₂Cl₂/MeOH and filtered. The filtrate was diluted with water and the organic phase evaporated to give the crude product which was dissolved in acetone/MeOH and evaporated onto silica gel. The material was purified by flash chromatography eluting isocratically with CH₂Cl₂/2 N ammonia solution in MeOH 15:1 to yield 330 mg of the title compound. ¹H NMR (DMSO-d6): δ 8.91 (s, 1H), 8.48 (s, 1H), 8.28 (d, 1H), J=5.4 Hz), 8.16 (d, 1H, J=2.1 Hz), 7.82 (m, 2H), 7.68 (d, 1H, J=6 Hz), 7.51 (d, 1H, J=8.1 Hz), 7.30 (d, 1H, J=8.4 Hz), 1.43 (s, 6H); LCMS: purity: 99%; MS (m/e): 432 (MH⁺)

Example 134

N4-(2,2-dimethyl-3,4-dihydro-3-oxo-2H-pyrido[3,2-b][1,4]oxazin-6-yl)-5-fluoro-N2-(6-(tetrahydro-2H-pyran-4-ylamino)pyridin-3-yl))-2,4-pyrimidinediamine (Compound 134)

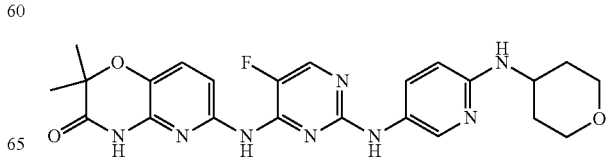

¹H NMR (DMSO-d₆, 300 MHz) 11.1 (s, 1H), 9.14 (m, 1H), 8.81 (m, 1H), 8.19 (m, 2H), 8.01 (m, 1H), 7.51 (m, 2H), 7.27 (m, 1H), 6.38 (m, 1H), 6.11 (m, 1H), 3.82 (m, 2H), 3.68 (m, 2H), 1.83 (m, 1H), 1.38 (m, 10H) ppm; MS (ES) 481.1 (M+H)

Example 135

N4-(2,2-dimethyl-3,4-dihydro-3-oxo-2H-pyrido[3,2-b][1,4]oxazin-6-yl)-5-fluoro-N2-[4-(4-hydroxycyclohexyl)aminopyrid-3-yl]-2,4-pyrimidinediamine (Compound 135)

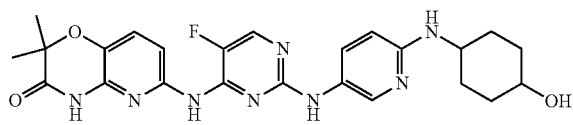 [SMILES: CC1(C)Oc2ccc(Nc3nc(Nc4ccc(NC5CCC(O)CC5)nc4)ncc3F)nc2NC1=O]

¹H NMR (DMSO-d₆, 300 MHz) 11.1 (s, 1H), 9.41 (m, 2H), 8.40 (m, 1H), 8.14 (m, 2H), 7.52 (m, 1H), 7.39 (m, 1H), 6.95 (m, 1H), 5.50 (m, 1H), 3.49 (m, 3H), 2.22 (m, 3H), 1.41 (s, 6H) ppm; MS (ES) 469.1 (M+H)

Example 136

(R)—N4-(2,2-dimethyl-3,4-dihydro-3-oxo-2H-pyrido[3,2-b][1,4]oxazin-6-yl)-5-fluoro-N2-[6-(3-fluoropyrrolidin-1-yl)pyrid-3-yl]-2,4-pyrimidinediamine (Compound 136)

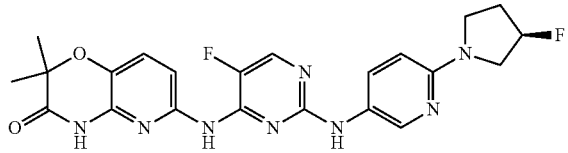 [SMILES: CC1(C)Oc2ccc(Nc3nc(Nc4ccc(N5CC[C@@H](F)C5)nc4)ncc3F)nc2NC1=O]

¹H NMR (DMSO-d₆, 300 MHz) 11.1 (s, 1H), 9.12 (m, 1H), 8.77 (m, 1H), 8.16 (m, 1H), 8.00 (m, 1H), 7.51 (m, 2H), 7.25 (m, 1H), 6.40 (m, 1H), 6.00 (m, 1H), 4.36 (bs, 1H), 3.66 (m, 2H), 1.56 (m, 8H), 1.41 (s, 6H) ppm; MS (ES) 495.1 (M+H)

Examples 137-159

| Cpd. No. | Structure Chemical Name |
|---|---|
| 137 | 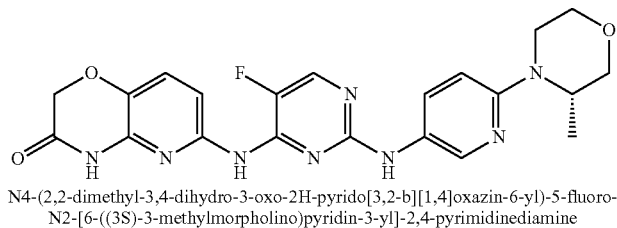<br>N4-(2,2-dimethyl-3,4-dihydro-3-oxo-2H-pyrido[3,2-b][1,4]oxazin-6-yl)-5-fluoro-N2-[6-((3S)-3-methylmorpholino)pyridin-3-yl]-2,4-pyrimidinediamine |
| 138 | 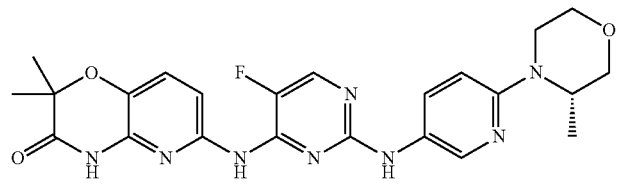 [SMILES: C[C@H]1COCCN1c1ccc(Nc2ncc(F)c(Nc3ccc4c(n3)NC(=O)C(C)(C)O4)n2)cn1]<br>N4-(2,2-dimethyl-3,4-dihydro-3-oxo-2H-pyrido[3,2-b][1,4]oxazin-6-yl)-5-fluoro-N2-[6-((3S)-3-methylmorpholino)pyridin-3-yl]-2,4-pyrimidinediamine |
| 139 | <br>N4-(2,2-dimethyl-3,4-dihydro-3-oxo-2H-pyrido[3,2-b][1,4]oxazin-6-yl)-5-fluoro-N2-[6-morpholinopyridin-3-yl]-2,4-pyrimidinediamine p-toluenesulfonic acid salt |
| 140 | 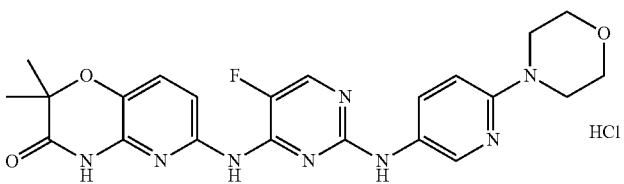 [SMILES: CC1(C)Oc2ccc(Nc3nc(Nc4ccc(N5CCOCC5)nc4)ncc3F)nc2NC1=O ; Cl]<br>N4-(2,2-dimethyl-3,4-dihydro-3-oxo-2H-pyrido[3,2-b][1,4]oxazin-6-yl)-5-fluoro-N2-[6-morpholinopyridin-3-yl]-2,4-pyrimidinediamine hydrochloric acid salt |

| Cpd. No. | Structure / Chemical Name |
|---|---|
| 141 | <br>N4-(2,2-dimethyl-3,4-dihydro-3-oxo-2H-pyrido[3,2-b][1,4]oxazin-6-yl)-5-fluoro-N2-[6-morpholinopyridin-3-yl]-2,4-pyrimidinediamine benzenesulfonic acid salt |
| 142 | 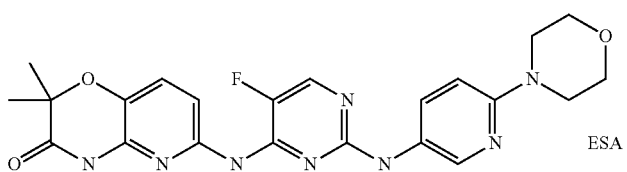<br>N4-(2,2-dimethyl-3,4-dihydro-3-oxo-2H-pyrido[3,2-b][1,4]oxazin-6-yl)-5-fluoro-N2-[6-morpholinopyridin-3-yl]-2,4-pyrimidinediamine ethanesulfonic acid salt |
| 143 | 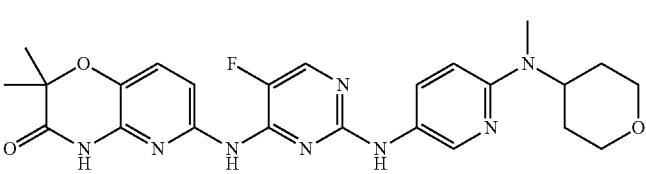 [SMILES: CN(c1ccc(Nc2ncc(F)c(Nc3ccc4c(n3)NC(=O)C(C)(C)O4)n2)cn1)C1CCOCC1]<br>N4-(2,2-dimethyl-3,4-dihydro-3-oxo-2H-pyrido[3,2-b][1,4]oxazin-6-yl)-5-fluoro-N2-[6-(methyl(tetrahydro-2H-pyran-4-yl)amino)pyridin-3-yl]-2,4-pyrimidinediamine |
| 144 | 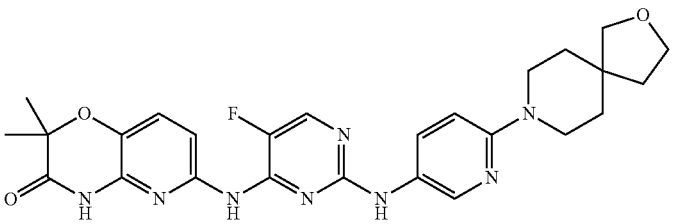<br>N4-(2,2-dimethyl-3,4-dihydro-3-oxo-2H-pyrido[3,2-b][1,4]oxazin-6-yl)-5-fluoro-N2-[6-(2-oxa-8-azaspiro[4.5]decan-8-yl)pyridin-3-yl]-2,4-pyrimidinediamine |
| 145 | 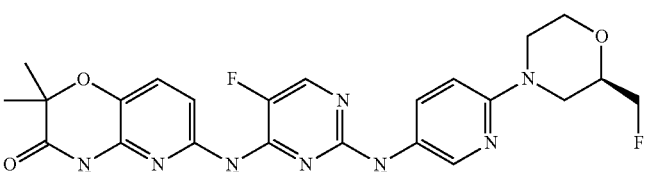<br>N4-(2,2-dimethyl-3,4-dihydro-3-oxo-2H-pyrido[3,2-b][1,4]oxazin-6-yl)-5-fluoro-N2-[6-((2R)-2-(fluoromethyl)morpholino)pyridin-3-yl]-2,4-pyrimidinediamine |
| 146 | 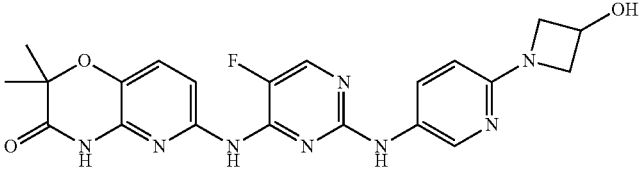 [SMILES: CC1(C)Oc2ccc(Nc3nc(Nc4ccc(N5CC(O)C5)nc4)ncc3F)nc2NC1=O]<br>N4-(2,2-dimethyl-3,4-dihydro-3-oxo-2H-pyrido[3,2-b][1,4]oxazin-6-yl)-5-fluoro-N2-[6-(3-hydroxyazetidin-1-yl)pyridin-3-yl]-2,4-pyrimidinediamine |

-continued

| Cpd. No. | Structure Chemical Name |
|---|---|
| 147 | 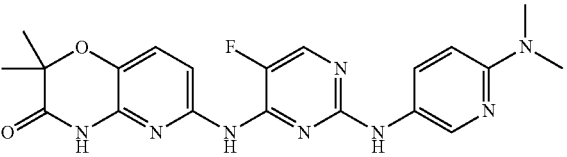<br>N4-(2,2-dimethyl-3,4-dihydro-3-oxo-2H-pyrido[3,2-b][1,4]oxazin-6-yl)-5-fluoro-N2-[6-(dimethylamino)pyridin-3-yl]-2,4-pyrimidinediamine |
| 148 | 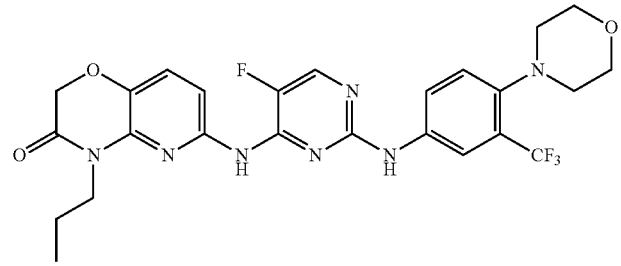 [SMILES: CCCN1C(=O)COc2ccc(Nc3nc(Nc4ccc(N5CCOCC5)c(C(F)(F)F)c4)ncc3F)nc21]<br>N4-(3,4-dihydro-3-oxo-4-propyl-2H-pyrido[3,2-b][1,4]oxazin-6-yl)-5-fluoro-N2-[4-morpholino-3-(trifluoromethyl)phenyl]-2,4-pyrimidinediamine |
| 149 | 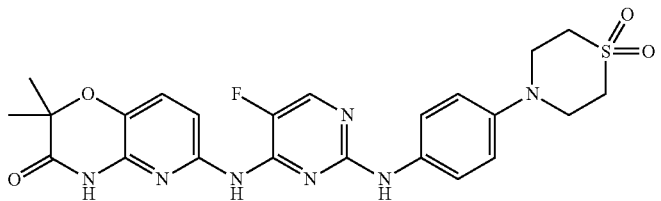 [SMILES: CC1(C)Oc2ccc(Nc3nc(Nc4ccc(N5CCS(=O)(=O)CC5)cc4)ncc3F)nc2NC1=O]<br>N4-(2,2-dimethyl-3,4-dihydro-3-oxo-2H-pyrido[3,2-b][1,4]oxazin-6-yl)-5-fluoro-N2-[4-(1,1-dioxidothiomorpholin-4-yl)phenyl]-2,4-pyrimidinediamine |
| 150 | 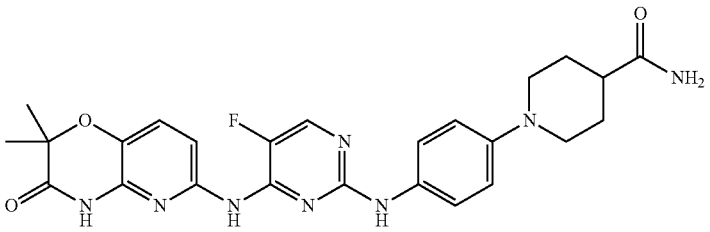 [SMILES: CC1(C)Oc2ccc(Nc3nc(Nc4ccc(N5CCC(C(N)=O)CC5)cc4)ncc3F)nc2NC1=O]<br>N4-(2,2-dimethyl-3,4-dihydro-3-oxo-2H-pyrido[3,2-b][1,4]oxazin-6-yl)-5-fluoro-N2-[4-(4-(aminocarbonyl)piperidin-1-yl)phenyl]-2,4-pyrimidinediamine |
| 151 | 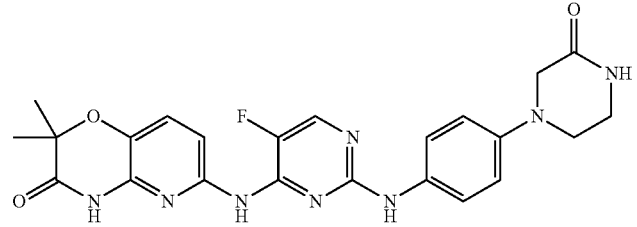 [SMILES: CC1(C)Oc2ccc(Nc3nc(Nc4ccc(N5CCNC(=O)C5)cc4)ncc3F)nc2NC1=O]<br>N4-(2,2-dimethyl-3,4-dihydro-3-oxo-2H-pyrido[3,2-b][1,4]oxazin-6-yl)-5-fluoro-N2-[4-(3-oxopiperazin-1-yl)phenyl]-2,4-pyrimidinediamine |
| 152 | 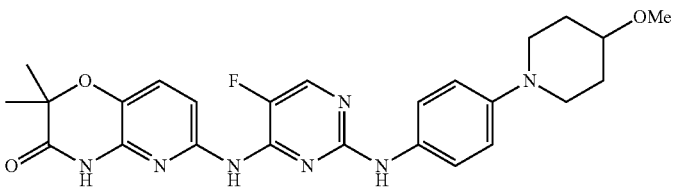 [SMILES: COC1CCN(c2ccc(Nc3ncc(F)c(Nc4ccc5c(n4)NC(=O)C(C)(C)O5)n3)cc2)CC1]<br>N4-(2,2-dimethyl-3,4-dihydro-3-oxo-2H-pyrido[3,2-b][1,4]oxazin-6-yl)-5-fluoro-N2-[4-(4-methoxypiperidin-1-yl)phenyl]-2,4-pyrimidinediamine |

| Cpd. No. | Structure Chemical Name |
|---|---|
| 153 | <br>N4-(2,2-dimethyl-3,4-dihydro-3-oxo-2H-pyrido[3,2-b][1,4]oxazin-6-yl)-5-fluoro-N2-[4-thiomorpholinophenyl]-2,4-pyrimidinediamine |
| 154 | 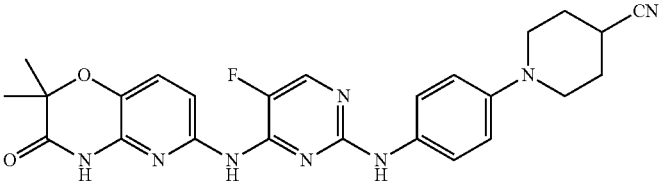 [SMILES: CC1(C)Oc2ccc(Nc3nc(Nc4ccc(N5CCC(C#N)CC5)cc4)ncc3F)nc2NC1=O]<br>N4-(2,2-dimethyl-3,4-dihydro-3-oxo-2H-pyrido[3,2-b][1,4]oxazin-6-yl)-5-fluoro-N2-[4-(4-cyanopiperidin-1-yl)phenyl]-2,4-pyrimidinediamine |
| 155 | 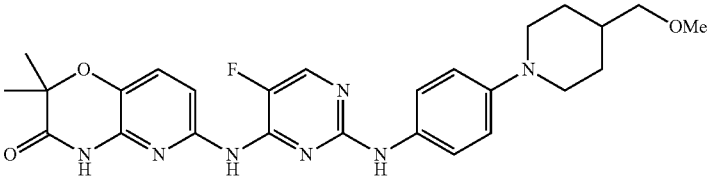 [SMILES: COCC1CCN(c2ccc(Nc3ncc(F)c(Nc4ccc5c(n4)NC(=O)C(C)(C)O5)n3)cc2)CC1]<br>N4-(2,2-dimethyl-3,4-dihydro-3-oxo-2H-pyrido[3,2-b][1,4]oxazin-6-yl)-5-fluoro-N2-[4-(4-(methoxymethyl)piperidin-1-yl)phenyl]-2,4-pyrimidinediamine |
| 156 | 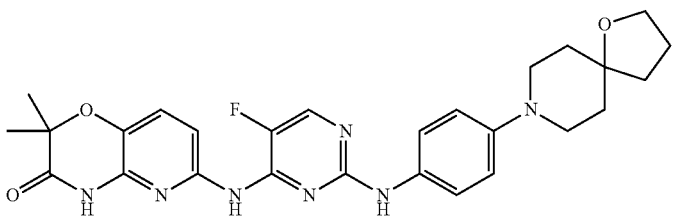 [SMILES: CC1(C)Oc2ccc(Nc3nc(Nc4ccc(N5CCC6(CCCO6)CC5)cc4)ncc3F)nc2NC1=O]<br>N4-(2,2-dimethyl-3,4-dihydro-3-oxo-2H-pyrido[3,2-b][1,4]oxazin-6-yl)-5-fluoro-N2-[4-(1-oxa-8-azaspiro[4.5]decan-8-yl)phenyl]-2,4-pyrimidinediamine |
| 157 | 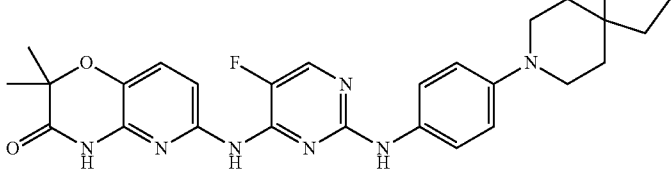<br>N4-(2,2-dimethyl-3,4-dihydro-3-oxo-2H-pyrido[3,2-b][1,4]oxazin-6-yl)-5-fluoro-N2-[4-(2-oxa-8-azaspiro[4.5]decan-8-yl)phenyl]-2,4-pyrimidinediamine |
| 158 | 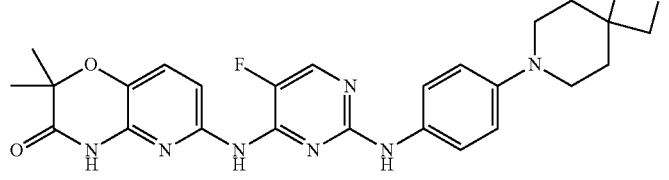<br>N4-(2,2-dimethyl-3,4-dihydro-3-oxo-2H-pyrido[3,2-b][1,4]oxazin-6-yl)-5-fluoro-N2-[4-(2-oxa-7-azaspiro[3.5]nonan-7-yl)phenyl]-2,4-pyrimidinediamine |

| Cpd. No. | Structure Chemical Name |
|---|---|
| 159 | 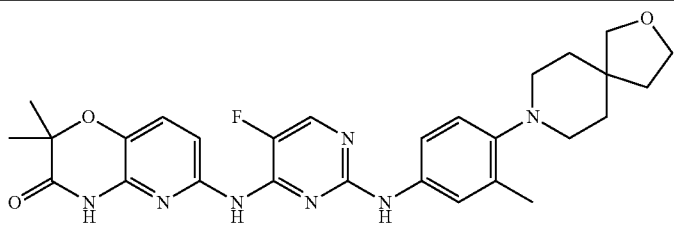<br>N4-(2,2-dimethyl-3,4-dihydro-3-oxo-2H-pyrido[3,2-b][1,4]oxazin-6-yl)-5-fluoro-N2-[3-methyl-4-(2-oxa-8-azaspiro[4.5]decan-8-yl)phenyl]-2,4-pyrimidinediamine |

Tryptase Release Assay of Exemplary Compounds

Compounds were assayed for inhibition of mast cell activation induced by FcγR cross-linking by measuring the activity of tryptase released upon degranulation as follows:

Human mast cells were cultured and differentiated from CD38-negative progenitor cell as described in U.S. Patent Publication No. 2005-234049, incorporated herein by reference. For example, 65 μL of various concentrations of the compound to be assayed were prepared in MT (137 mM NaCl, 2.7 mM KCl, 1.8 mM CaCl$_2$, 1.0 mM MgCl$_2$, 5.6 mM Glucose, 20 mM Hepes (pH 7.4), 0.1% Bovine Serum Albumin, (Sigma A4503)) containing 2% MeOH and 1% DMSO, or control buffer were added to duplicate 96-well V-bottom plates. Pelleted and re-suspended (in warm MT) CHMC cells (65 μL) were added to each 96-well plate, mixed and incubated for 1 hour at 37° C. 25 μl of 6× anti-IgG Rabbit anti-human IgG, Affinity purified (Bethyl Laboratories Cat No. A80-105A3) final concentration 1 μg/mL, was added to the test wells. MT (25 μL) was added to control wells. After a 60-minute incubation at 37° C., cells and cell debris were pelleted by centrifugation at 1000 rpm for 10 min and tryptase and leukotriene C$_4$ levels were measured.

To measure tryptase levels, 25 μL of supernatant from each well was transferred to a fresh 96-well black bottom plate, to which 100 μL of fresh tryptase substrate solution [(Z-Ala-Lys-Arg-AMC2TFA; Enzyme Systems Products, #AMC-246)] 1:2000 in tryptase assay buffer [0.1 M Hepes (pH 7.5), 10% w/v Glycerol, 10 μM Heparin (Sigma H-4898) 0.01% NaN$_3$] was added. After 30 minute incubation at room temperature, the optical density of the plates is measured at 355 nm/460 nm on a spectrophotometric plate reader. Table 1 provides the IC$_{50}$ values.

Compounds of the disclosure were assayed for their ability to inhibit mast cell activation induced by FcγR cross-linking by measuring the activity of tryptase released upon degranulation. The IC$_{50}$ values for the LD Tryptase assay are presented in Table 2, in which "0" is >100 μM; "A" is 1-100 μM; "B" is 0.5-1 μM; "C" is 0.1-0.5 μM; and "D" is less than 0.1 μM:

TABLE 2

| Compound No. | LD Tryptase CHMC |
|---|---|
| Compound 1 | D |
| Compound 2 | A |
| Compound 3 | D |
| Compound 4 | A |
| Compound 5 | C |
| Compound 6 | D |
| Compound 7 | C |
| Compound 8 | C |
| Compound 9 | C |
| Compound 10 | C |
| Compound 11 | D |
| Compound 12 | D |
| Compound 13 | D |
| Compound 14 | B |
| Compound 15 | A |
| Compound 16 | C |
| Compound 17 | C |
| Compound 18 | B |
| Compound 19 | A |
| Compound 21 | C |
| Compound 22 | C |
| Compound 23 | D |
| Compound 24 | D |
| Compound 25 | A |
| Compound 26 | D |
| Compound 27 | D |
| Compound 28 | 0 |
| Compound 29 | A |
| Compound 30 | A |
| Compound 31 | A |
| Compound 32 | D |
| Compound 33 | D |
| Compound 34 | D |
| Compound 35 | C |
| Compound 36 | C |
| Compound 37 | C |
| Compound 38 | D |
| Compound 39 | C |
| Compound 40 | C |
| Compound 41 | C |
| Compound 42 | C |
| Compound 43 | C |
| Compound 44 | C |
| Compound 45 | A |
| Compound 46 | D |
| Compound 47 | A |
| Compound 48 | C |
| Compound 49 | D |
| Compound 50 | D |
| Compound 51 | D |
| Compound 52 | D |
| Compound 53 | C |
| Compound 54 | A |
| Compound 55 | D |
| Compound 56 | C |
| Compound 57 | C |
| Compound 58 | A |
| Compound 59 | C |
| Compound 60 | C |
| Compound 61 | C |
| Compound 62 | B |
| Compound 63 | C |

TABLE 2-continued

| Compound No. | LD Tryptase CHMC |
|---|---|
| Compound 64 | C |
| Compound 65 | C |
| Compound 66 | B |
| Compound 67 | C |
| Compound 68 | C |
| Compound 69 | 0 |
| Compound 70 | B |
| Compound 71 | C |
| Compound 72 | C |
| Compound 73 | C |
| Compound 74 | A |
| Compound 75 | A |
| Compound 76 | C |
| Compound 77 | D |
| Compound 78 | A |
| Compound 79 | C |
| Compound 80 | D |
| Compound 81 | C |
| Compound 82 | C |
| Compound 83 | C |
| Compound 84 | C |
| Compound 85 | C |
| Compound 86 | A |
| Compound 87 | C |
| Compound 88 | C |
| Compound 89 | C |
| Compound 90 | C |
| Compound 91 | D |
| Compound 92 | D |
| Compound 93 | C |
| Compound 94 | C |
| Compound 95 | C |
| Compound 96 | C |
| Compound 97 | A |
| Compound 98 | B |
| Compound 99 | C |
| Compound 100 | C |
| Compound 101 | C |
| Compound 102 | C |
| Compound 103 | C |
| Compound 104 | C |
| Compound 105 | C |
| Compound 106 | D |
| Compound 107 | D |
| Compound 108 | C |
| Compound 109 | C |
| Compound 110 | A |
| Compound 111 | C |
| Compound 112 | B |
| Compound 113 | A |
| Compound 114 | A |
| Compound 115 | D |
| Compound 116 | D |
| Compound 117 | D |
| Compound 118 | D |
| Compound 119 | D |
| Compound 120 | C |
| Compound 121 | D |
| Compound 122 | C |
| Compound 123 | C |
| Compound 124 | A |
| Compound 125 | D |
| Compound 126 | C |
| Compound 127 | D |
| Compound 128 | D |
| Compound 129 | A |
| Compound 130 | D |
| Compound 131 | D |
| Compound 132 | D |
| Compound 133 | D |
| Compound 134 | D |
| Compound 135 | D |
| Compound 136 | D |
| Compound 137 | D |
| Compound 138 | C |
| Compound 139 | B |
| Compound 140 | B |
| Compound 141 | C |
| Compound 142 | C |
| Compound 143 | D |
| Compound 144 | C |
| Compound 145 | D |
| Compound 146 | A |
| Compound 147 | C |
| Compound 148 | D |
| Compound 149 | D |
| Compound 150 | C |
| Compound 151 | C |
| Compound 152 | D |
| Compound 153 | A |
| Compound 154 | C |
| Compound 155 | C |
| Compound 156 | C |
| Compound 157 | C |
| Compound 158 | C |
| Compound 159 | B |

Fluorescence Polarization Syk Kinase Assay

Compounds are tested for the ability to inhibit Syk kinase catalyzed phosphorylation of a peptide substrate in a biochemical fluorescence polarization assay with isolated Syk kinase.

Test compound stock solutions (10 mM) containing are serially diluted in DMSO starting from 2.5 mM and then further diluted to desired concentration of 50 µM (5×) to yield 2% DMSO concentration in kinase buffer (20 mM HEPES, pH 7.4, 5 mM $MgCl_2$, 2 mM $MnCl_2$, 1 mM DTT, 0.1 mg/mL acetylated Bovine Gamma Globulin). The assay is carried out in a black 96 well low volume plate (Molecular Devices, #42-000-0117) by transferring compound in 2% DMSO (0.4% DMSO final) pre-mixed with ATP/substrate (TK2 peptide) in kinase buffer at room temperature. Syk kinase (Millipore, #14-314) is added to a final reaction volume of 20 µL, and the reaction is incubated for 30 minutes at room temperature. Final enzyme reaction conditions are 20 mM HEPES, pH 7.4, 5 mM $MgCl_2$, 2 mM $MnCl_2$, 1 mM DTT, 0.1 mg/mL acetylated Bovine Gamma Globulin (Invitrogen, #P2255), 25 ng Syk, 2.5 µM ATP, 5 µM peptide substrate (Biotin-EGP-WLEEEEAYGWMDF-$CONH_2$, Anaspec, #60329-1). The reaction is stopped by addition of 20 µL of PTK quench mix containing EDTA (10 mM final)/anti-phosphotyrosine antibody (1× final)/fluorescent phosphopeptide tracer (0.5× final) diluted in FP dilution buffer to stop the reaction to a total volume of 40 µL according to the manufacturer's instructions (Invitrogen). The plate is incubated in the dark for additional 30 minutes at room temperature and then read on a Polarion fluorescence polarization plate reader (Tecan). Data are converted to amount of phosphopeptide present using a calibration curve generated by competition with the phosphopeptide competitor provided in the Tyrosine Kinase Assay Kit, Green (Invitrogen, #P2837).

CD63 Assay

Compounds are tested for the ability to inhibit allergen induced basophil degranulation. The BASOTEST® kit (Orpegen Pharma GmbH, #10-0500) is used in this assay. In a 5 mL FACS tube 105 µL of Heparinized whole blood, 25 µL, of test compound solution (in DMSO) are incubated at room temperature for 30-60 minutes. To induce degranulation, 20 µL stimulation buffer (Reagent B) is added, and the tube is incubated for 10 min in a 37° C. water bath. Then, 100 µL of anti-IgE (2 µg/mL) is added, or 100 L of washing solution (reagent A) is added (i.e., as a negative control). The tube is incubated for 20 min in a 37° C. water bath. Degranulation is then stopped by incubation on ice for 5 min. 20 µL of staining reagent (reagent F) is added, and the tube is incubated on ice in the dark for 20 min. 2 mL of room temperature lysing solution is added, and the tube is incubated at room temperature for 10 min. The tubes are spun down at 4° C. for 5 min at 1600 rpm, and the supernatant is discarded. 3 mL washing solution (reagent A) is added, and the tubes spun down at 4° C. for 5 min at 1600 rpm, and the supernatant is discarded. 200 µL washing solution is added to the remaining cell pellet, and the samples are incubated on ice in the dark until analysis (within 2 h). Analysis is performed using flow cytometry at 488 nm using the conditions specified in the BASOTEST® kit instructions to determine percentage of activated basophilic granulocytes.

Biochemical VEGFR Assay

Compounds are tested for the ability to inhibit VEGF2 in an ELISA assay. NUNC MAXISORP 96 well plates (#436110) are coated with 0.01 mg/mL NeutrAvidin in 1×PBS (100 µL/well) for 18-24 h at 4° C. Plates are then washed with 1×PBST using a plate washer, then blocked with 2% BSA in 1×PBST (100 µL/well) for 1 hr at room temperature. The NeutrAvidin-coated plates are again washed with 1×PBST using a plate washer.

Test compound solutions (4.8 µL/well) of various concentrations (in DMSO) are transferred to wells of a fresh uncoated 96-well plate, along with 115 µL/well of reaction solution (4700 parts kinase buffer (5772 parts water, 120 parts 1M HEPES (pH 7.4), 30 parts 1M $MgCl_2$, 12 parts 1M $MnCl_2$, 6 parts 1M DTT, 60 parts 1% Brij-35), 1.14 parts 10 mM ATP, 11.4 parts 1 mM TK2 peptide (AnaSpec, #60329-1)). The mixed test compound/reaction solutions are added to the wells of the NeutrAvidin-coated plates (50 µL/well). 6× enzyme solution (1000 parts kinase buffer, 0.6 parts KDR/VEGFR2 enzyme (50 µg/mL, Millipore, #14-630) is added to all wells except those designated as negative controls. The plates are incubated for 30 minutes on a shaker at room temperature.

Detection reagent is prepared by mixing 10000 parts 0.1% BSA in PBST with 1 part anti-pTyr mouse mAb (Cell Signaling, #9411) and 1 part HRP-goat anti-mouse IgG (Jackson Immunoresearch, #115-035-003). The detection reagent is added at 100 µL/well, and the plates are incubated for 60 minutes at room temperature, then washed with 1×PBST using a plate washer. Plates are developed by adding 100 L of ELISA Pico Chemi substrate (Fisher Scientific, #PI-37069), and read by chemiluminescence (0.1 s) using a Wallac 1420 counter.

Cellular VEGFR Assay

Compounds are tested for the ability to exhibit VEGF-induced phosphorylation of VEGFR in HUVEC cells.

96-well high binding opaque white plates (Pierce, #15042) are coated overnight with 5 µg/mL of mouse anti-human VEGFR2 mAb (R&D Systems, #MAB3572). The coated plates are then blocked with 2% BSA in PBS for 2 hours.

HUVEC cells (Cambrex, #CC-2519, cultured in complete medium and incubated in a humidified atmosphere of 5% $CO_2$ at 37° C.) are seeded at a density of 18-20K cells/well in 100 µL, complete medium (EGM-2 BulletKit, Cambrex, #CC-3162) in a 96-well clear bottom plate for 24 hours in a 37° C./5% $CO_2$ incubator. Cells are washed 1× with PBS. 100 µL, starvation medium (EBM2 media, Cambrex, #CC3156, containing 1% BSA and 0.2% FBS) is added and cells are returned to the incubator for 20-24 hours. Test compounds or control drugs are serially diluted in DMSO in a compound plate and further diluted 1:250 in starvation medium. 100 µL, of this 2× concentration is dosed to the cells. After a 1 hour pre-treatment, the cells are stimulated with 100 ng/mL recombinant human VEGF165 (R&D Systems, #293-VE) for 5 minutes. Immediately after stimulation, the cells are washed 1× with cold PBS and 33 µL, cold lysis buffer (9 ml RIPA buffer, Teknova, #R3792) containing a protease inhibitor tablet (Roche, #1697498), 1 mM NEM, 1 mM PMSF, 10 µM MG132, and 1 mM $NaVO_4$ and 1 mL 10× cell lysis buffer (Cell Signal Technology, #9803) is added. Plates are then placed on a rocker/shaker at 4° C. for 1 hour.

Phosphorylated VEGFR2 is determined by ELISA. After a wash with TBST, 30 µL/well of the cell lysate is transferred into the anti-human VEGFR2 mAb-coated plates (described above) containing 200 µL/well of 1% BSA in PBS, and incubated with shaking at 4° C. overnight. The plates are washed 4× with TBST and stained with 1:1000 diluted phospho-VEGFR2Rabbit mAb (Cell Signal Technology, 2478) in 0.2% BSA in TBST, and allowed to shake for 2 hours. Plates are washed 4× with TBST, and 1:5000 dilution anti-Rabbit HRP (Jackson ImmunoResearch, #111-035-144) in 0.2% BSA in TBST is added and the plates are placed on the shaker for another hour. A final 4× wash with TBST and SuperSignal ELISA Pico Substrate (Pierce, #37070a/b) was added at a 1:1:1 ratio of test compound, A, B and water for chemiluminescent detection of the HRP conjugate. The signal is read using a SpectraMax M5 plate reader.

The VEGF assay data are significant because, without being limited to any particular theory, Applicants currently believe that VEGF inhibition leads to elevated blood pressure (see Kamba et al., *British Journal of Cancer* 96:1788-1795 (2007); Roodhart et al. *Current Clinical Pharmacology* 3:132-143 (2008); Franklin et al. *JPET* 329:928-937 (2009)).

Cellular Ret Assay

Compounds are tested for the ability to inhibit Ret kinase in cells. SK-N-SH brain neuroblastoma cells (ATCC, #HTB-1, maintained and plated in DMEM (Cellgro Mediatech, #10-0, 3-CV) with 10% fetal bovine serum (JRH, #12106-500M) are seeded in 10 cm plates in 10 mL of culture media and allowed to reach 85% confluence by the next day. The medium is replaced with 5 mL of DMEM (without fetal bovine serum) containing DMSO or test compound (final 0.1% DMSO), and incubated at 37° C./5% $CO_2$ for 1 hour. SK-N-SH cells are then stimulated with 50 ng/mL of human recombinant GDNF (Peprotech, #450-10) for 10 minutes. Cells are washed once with cold 1×PBS and lysed with 500 µL, of 1% NP-40 lysis buffer (Tris HCl pH 7.4 with 150 mM NaCl, 1 mM NaVn, 1% Nonidet-P40 (Fisher Scientific, #PI-28324), protease inhibitor tablet (Roche, 1697498)). Cells are scraped off the plate in lysis buffer after sitting on ice for 10 minutes. The detergent-insoluble fraction is removed by centrifugation at 14,000 rpm for 10 minutes at 4° C. Ret is immunoprecipitated from the detergent-soluble cell lysate by rotation with 3 µL, of anti-Ret rabbit polyclonal antibody (Cell Signaling Technology, Cat#3220) and 15 µL, of protein A/G agarose (Fisher Scientific, #PI-20421) at 4° C. overnight.

The agarose is washed twice with lysis buffer and the Ret proteins are eluted by heating at 98° C. for 5 minutes in 1× NuPAGE LDS sample buffer (Invitrogen, #NP0007). The eluted proteins are separated by electrophoresis on a Tris-Bis gel (NuPAGE Bis-Tris 4-12% Gel, 1.0 mm, 15 well, Invitrogen, #NP0323BOX) and transferred to an Invitrolon PVDF membrane (pore size 0.45 µm, Invitrogen, #LC2005). The membrane is blocked for 1 hour in 1×TBST containing 5% milk. The membrane is probed overnight at 4° C. with anti-phosphotyrosine(4G10) mouse monoclonal antibody (Millipore Corporation, Cat#05-321, 1:5,000) in 1×TBST+5% milk.

After washing with 1×TBST for 2 hours with five buffer changes, the membrane is probed with Goat anti-Mouse IgG HRP antibody (Jackson Immunoresearch Labs, #115-035-146, 1:2000) in 1×TBST+5% milk for 1 hour at room temperature. The membrane is washed with TBST for 2 hours with five buffer changes, treated with ECL plus Western Blot detection reagent (GE Healthcare, formerly Amersham, #RPN2132) according to the instruction manual, and the chemiluminescent signal is detected on Kodak Biomax MR Film (VWR, #IB8701302).

Biochemical Ret Assay

Compounds are tested for the ability to inhibit Ret kinase in an ELISA-based assay. The assay is carried out in a Costar white 96 well plate (Fisher Scientific, #07-200-591) coated overnight with 0.01 mg/mL NeutrAvidin (Pierce, 100 μL/well) at 4° C. The pre-coated 96 well plate is blocked with 2% BSA in PBST buffer for at least 1 h at room temperature before starting the assay. Serially diluted test compound stock solution is prepared separately in DMSO solution starting from 300 μM, and 2 μL/well of this diluted compound (3% DMSO final concentration) is added directly to the NeutrAvidin coated assay plate containing 55.5 μL/well of kinase reaction buffer (20 mM HEPES, pH 7.4, 5 mM MgCl$_2$, 1 mM DTT, 0.01% Brij-35) pre-mixed with ATP and kinase substrate (TK2 peptide). Reaction is initiated by adding 2.5 μL/well Ret kinase (Millipore, #14-570) resulting in a final reaction volume of 60 μL. The reaction is allowed to continue for 30 minutes at room temperature. Final enzyme reaction conditions in 60 μL are 20 mM HEPES, pH 7.4, 5 mM MgCl$_2$, 1 mM DTT, 0.01% Brij-35, 0.15 ng Ret, 2 μM ATP, 2 μM peptide TK2 substrate (Biotin-EGPWLEEEEEAYGWMDF-CONH$_2$, Anaspec, #60329-1). After completing the reaction, the wells are washed three times with PBST and incubated for 1 h at room temperature with 100 μL/well of phosphopeptide detection antibody solution (mixture of 1:10000 diluted mouse anti-pTyr monoclonal antibody (Cell Signal Technology, #9411) and 1:10000 diluted goat HRP-conjugated anti-mouse IgG (Jackson Immunoresearch, #115-035-003)). The plate is washed three times with PBST, developed with supersignal ELISA pico chemiluminescent substrate (Pierce), and read on a SpectraMax M5 microplate reader (Molecular Devices).

Ret kinase is believed to be necessary for kidney development. Because more arthritis patients are women than men, any potential developmental toxicity, such as may be associated with Ret inhibition, is a serious limitation (see Clemens et al. *Birth defect Research* (Part A) 85:130-136 (2009)).

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

We claim:
1. A compound of formula:

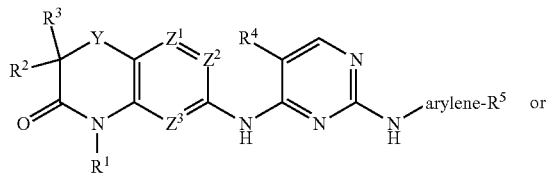

-continued

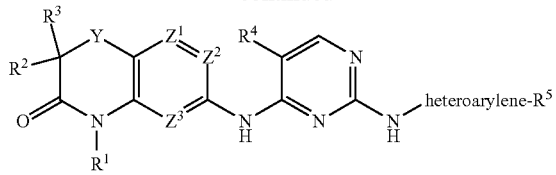

or a pharmaceutically acceptable salt thereof, wherein:
Y is oxygen or sulfur;
$Z^1$, $Z^2$, and $Z^3$ are independently selected from CH and N, provided that at least one of $Z^1$ $Z^2$ and $Z^3$ is N;
$R^1$ is hydrogen or $C_1$-$C_6$ alkyl;
$R^2$ and $R^3$ are independently selected from hydrogen, halogen, $C_1$-$C_6$ alkyl, and halo($C_1$-$C_6$ alkyl), or $R^2$ and $R^3$ together with the carbon to which they are attached form $C_3$-$C_6$ cycloalkyl;
$R^4$ is hydrogen, halogen, cyano, nitro, $C_1$-$C_6$ alkyl, or halo($C_1$-$C_6$ alkyl);
$R^5$ is $C_1$-$C_6$ alkyl, —N($R^7$)$_2$, aryl optionally substituted with 1, 2, 3, or 4 $R^6$ groups, heteroaryl optionally substituted with 1, 2, 3, or 4 $R^6$ groups, cycloalkyl optionally substituted with 1, 2, 3, 4, 5, 6, 7, or 8 $R^6$ groups, or heterocycloalkyl optionally substituted with 1, 2, 3, 4, 5, 6, 7, or 8 $R^6$ groups, in which
each $R^6$ is independently selected from deuterium, halogen, cyano, nitro, hydroxy, $C_1$-$C_6$ alkyl, $C_2$-$C_6$ alkenyl, $C_2$-$C_6$ alkynyl, halo($C_1$-$C_6$ alkyl), $C_1$-$C_6$ alkoxy, halo($C_1$-$C_6$ alkoxy), amino, ($C_1$-$C_6$ alkyl)amino, di($C_1$-$C_6$ alkyl)amino, hydroxy($C_1$-$C_6$ alkyl), ($C_1$-$C_6$ alkoxy)$C_1$-$C_6$ alkyl, amino($C_1$-$C_6$ alkyl), (($C_1$-$C_6$ alkyl)amino)($C_1$-$C_6$ alkyl), (di($C_1$-$C_6$ alkyl)amino)($C_1$-$C_6$ alkyl), —C(O)OH, —C(O)NH$_2$, $C_3$-$C_8$ cycloalkyl, aryl, heteroaryl, and heterocycloalkyl, or two $R^6$ groups form a spiro-fused $C_3$-$C_6$ cycloalkyl, a spiro-fused heterocycloalkyl, oxo, =CH$_2$, or =CH ($C_1$-$C_6$ alkyl); and
each $R_7$ is independently selected from hydrogen, $C_1$-$C_6$ alkyl, $C_2$-$C_6$ alkenyl, $C_2$-$C_6$ alkynyl, halo($C_1$-$C_6$ alkyl), hydroxy($C_1$-$C_6$ alkyl), ($C_1$-$C_6$ alkoxy)$C_1$-$C_6$ alkyl, aryl, heteroaryl, heterocycloalkyl, (aryl)$C_1$-$C_6$ alkyl, (heteroaryl)$C_1$-$C_6$ alkyl, and (heterocycloalkyl) $C_1$-$C_6$ alkyl;
wherein the arylene is further substituted with 0, 1, 2, 3, or 4 $R^9$, where each $R^9$ is independently selected from halogen, cyano, $C_1$-$C_6$ alkyl, halo($C_1$-$C_6$ alkyl), $C_1$-$C_6$ alkoxy, and halo($C_1$-$C_6$ alkoxy), or $R^9$ and $R^5$ together with the carbons to which they are attached form $C_5$-$C_{10}$ heterocycloalkyl; and
the heteroarylene is further substituted with 0, 1, 2, 3, or 4 $R^{10}$, where each $R^{10}$ is independently selected from halogen, cyano, $C_1$-$C_6$ alkyl, halo($C_1$-$C_6$ alkyl), $C_1$-$C_6$ alkoxy, and halo($C_1$-$C_6$ alkoxy), or $R^{10}$ and $R^5$ together with the carbons to which they are attached form $C_5$-$C_{10}$ heterocycloalkyl,
provided the compound is not
N4-(3,4-dihydro-3-oxo-2H-pyrido[3,2-b][1,4]oxazin-6-yl)-5-fluoro-N2-(4-morpholinophenyl)-2,4-pyrimidinediamine,
N4-(2,2-dimethyl-3,4-dihydro-3-oxo-2H-pyrido[3,2-b][1,4]oxazin-6-yl)-5-fluoro-N2-(4-morpholinophenyl)-2,4-pyrimidinediamine,
N4-(2,2-dimethyl-3,4-dihydro-3-oxo-2H-pyrido[3,2-b][1,4]oxazin-6-yl)-5-fluoro-N2-(4-(4-methylpiperazin-1-yl)phenyl)-2,4-pyrimidinediamine, or N4-(3,4-dihydro-3-oxo-2H-pyrido[3,2-b][1,4]oxazin-6-yl)-5-fluoro-N2-(4-ethoxycarbonylpiperazin-1-yl(phenyl))-2,4-pyrimidinediamine.

2. The compound according to claim 1, having the formula

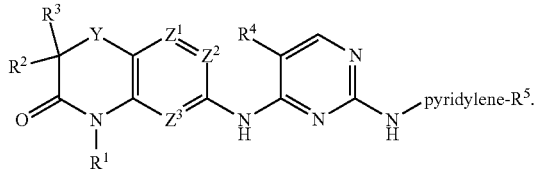

3. The compound according to claim 2, wherein the $R^5$ is substituted at the para position of the heteroarylene with respect to the pyrimidin-2-ylamine.

4. The compound according to claim 1, wherein $Z^1$ is carbon, $Z^2$ is carbon, and $Z^3$ is nitrogen.

5. The compound according to claim 1, wherein $Z^1$ is nitrogen, $Z^2$ is carbon, and $Z^3$ is carbon.

6. The compound according to claim 1, wherein $R^2$ and $R^3$ are independently selected from hydrogen and $C_1$-$C_6$ alkyl, or $R^2$ and $R^3$ together with the carbon to which they are attached form $C_3$-$C_6$ cycloalkyl.

7. The compound according to claim 1, wherein $R_1$ is hydrogen.

8. The compound according to claim 1, wherein $R^4$ is —F.

9. The compound according to claim 1, wherein $R^5$ is heterocycloalkyl optionally substituted with 1, 2, 3, 4, 5, 6, 7 or 8 $R^6$.

10. The compound according to claim 9, wherein the heterocycloalkyl is morpholinyl, thiomorpholinyl, piperidinyl, piperazinyl, pyrrolidinyl, oxazolidinyl, azetidinyl, tetrahydropyranyl, oxazepanyl, 2-oxa-5-azabicyclo[2.2.1]heptanyl, or 1,4-diazabicyclo[3.2.2]nonanyl.

11. The compound according to claim 1, wherein each $R^6$ is independently selected from hydroxy, $C_1$-$C_6$ alkyl, halo ($C_1$-$C_6$ alkyl), $C_1$-$C_6$ alkoxy, hydroxy($C_1$-$C_6$ alkyl), ($C_1$-$C_6$ alkoxy)$C_1$-$C_6$ alkyl, amino, ($C_1$-$C_6$ alkyl)amino, and di($C_1$-$C_6$ alkyl)amino.

12. The compound according to claim 1, wherein $R^5$ is —N($R^7$)$_2$, in which each $R^7$ is independently selected from hydrogen, $C_1$-$C_6$ alkyl, $C_2$-$C_6$ alkenyl, $C_2$-$C_6$ alkynyl, halo ($C_1$-$C_6$ alkyl), hydroxy($C_1$-$C_6$ alkyl), ($C_1$-$C_6$ alkoxy)$C_1$-$C_6$ alkyl, aryl, heteroaryl, heterocycloalkyl, (aryl)$C_1$-$C_6$ alkyl, (heteroaryl)$C_1$-$C_6$ alkyl, and (heterocycloalkyl)$C_1$-$C_6$ alkyl.

13. The compound according to claim 1, which is:
N4-(2,2-dimethyl-3,4-dihydro-3-oxo-2H-pyrido[3,2-b][1,4]oxazin-6-yl)-5-fluoro-N2-(4-morpholinophenyl)-2,4-pyrimidinediamine;
N4-(2,2-dimethyl-3,4-dihydro-3-oxo-2H-pyrido[3,2-b][1,4]oxazin-6-yl)-5-fluoro-N2-[3-methyl-4-morpholinophenyl]-2,4-pyrimidinediamine;
N4-(2,2-dimethyl-3,4-dihydro-3-oxo-2H-pyrido[3,2-b][1,4]oxazin-6-yl)-5-fluoro-N2-[3-methyl-4-((1S,4S)-5-oxa-2-aza-bicyclo[2.2.1]heptan-2-yl)phenyl]-2,4-pyrimidinediamine;
N4-(2,2-dimethyl-3,4-dihydro-3-oxo-2H-pyrido[3,2-b][1,4]oxazin-6-yl)-5-fluoro-N2-[3-difluoromethoxy-4-morpholinophenyl]-2,4-pyrimidinediamine;
N4-(2,2-dimethyl-3,4-dihydro-3-oxo-2H-pyrido[3,2-b][1,4]oxazin-6-yl)-5-fluoro-N2-[3-fluoro-4-morpholinophenyl]-2,4-pyrimidinediamine;
N4-(2,2-dimethyl-3,4-dihydro-3-oxo-2H-pyrido[3,2-b][1,4]oxazin-6-yl)-5-fluoro-N2-[3-methoxy-4-morpholinophenyl]-2,4-pyrimidinediamine;
N4-(2,2-dimethyl-3,4-dihydro-3-oxo-2H-pyrido[3,2-b][1,4]oxazin-6-yl)-5-fluoro-N2-[3-trifluoromethoxy-4-morpholinophenyl]-2,4-pyrimidinediamine;
N4-(2,2-dimethyl-3,4-dihydro-3-oxo-2H-pyrido[3,2-b][1,4]oxazin-6-yl)-5-fluoro-N2-[4-(4,4-difluoro-1-piperidinyl)phenyl]-2,4-pyrimidinediamine;
N4-(2,2-dimethyl-3,4-dihydro-3-oxo-2H-pyrido[3,2-b][1,4]oxazin-6-yl)-5-fluoro-N2-[3-fluoro-4-(4,4-difluoro-1-piperidinyl)phenyl]-2,4-pyrimidinediamine;
N4-(2,2-dimethyl-3,4-dihydro-3-oxo-2H-pyrido[3,2-b][1,4]oxazin-6-yl)-5-fluoro-N2-[3,5-difluoro-4-morpholinophenyl]-2,4-pyrimidinediamine;
N4-(3,4-dihydro-3-oxo-2H-pyrido[3,2-b][1,4]oxazin-6-yl)-5-fluoro-N2-[4-morpholino)phenyl]-2,4-pyrimidinediamine;
N4-(3,4-dihydro-3-oxo-2H-pyrido[3,2-b][1,4]oxazin-6-yl)-5-fluoro-N2-[3-methoxy-4-morpholinophenyl]-2,4-pyrimidinediamine;
N4-(3,4-dihydro-3-oxo-2H-pyrido[3,2-b][1,4]oxazin-6-yl)-5-fluoro-N2-[3-fluoro-4-morpholinophenyl]-2,4-pyrimidinediamine;
rac-Cis-N4-(3,4-dihydro-3-oxo-2H-pyrido[3,2-b][1,4]oxazin-6-yl)-5-fluoro-N2-[4-(2,6-dimethylmorpholino)phenyl]-2,4-pyrimidinediamine;
rac-Cis-N4-(2,2-dimethyl-3,4-dihydro-3-oxo-2H-pyrido[3,2-b][1,4]oxazin-6-yl)-5-fluoro-N2-[4-(2,6-dimethylmorpholino)phenyl]-2,4-pyrimidinediamine;
N4-(3,4-dihydro-3-oxo-2H-pyrido[3,2-b][1,4]oxazin-6-yl)-5-fluoro-N2-[4-((1S,4S)-5-oxa-2-aza-bicyclo[2.2.1]heptan-2-yl)phenyl]-2,4-pyrimidinediamine;
N4-(2,2-dimethyl-3,4-dihydro-3-oxo-2H-pyrido[3,2-b][1,4]oxazin-6-yl)-5-fluoro-N2-[4-((1S,4S)-5-oxa-2-aza-bicyclo[2.2.1]heptan-2-yl)phenyl]-2,4-pyrimidinediamine;
N4-(3,4-dihydro-3-oxo-2H-pyrido[3,2-b][1,4]oxazin-6-yl)-5-fluoro-N2-[4-(morpholin-2-one)phenyl]-2,4-pyrimidinediamine;
N4-(2,2-dimethyl-3,4-dihydro-3-oxo-2H-pyrido[3,2-b][1,4]oxazin-6-yl)-5-fluoro-N2-[4-(morpholin-2-one)phenyl]-2,4-pyrimidinediamine;
N4-(3,4-dihydro-3-oxo-2H-pyrido[3,2-b][1,4]oxazin-6-yl)-5-fluoro-N2-[4-(((2S)-2-ethoxymethyl)morpholino)phenyl]-2,4-pyrimidinediamine;
N4-(2,2-dimethyl-3,4-dihydro-3-oxo-2H-pyrido[3,2-b][1,4]oxazin-6-yl)-5-fluoro-N2-[4-(((2S)-2-ethoxymethyl)morpholino)phenyl]-2,4-pyrimidinediamine;
N4-(2,2-dimethyl-3,4-dihydro-3-oxo-2H-pyrido[3,2-b][1,4]oxazin-6-yl)-5-fluoro-N2-[4-homomorpholinophenyl]-2,4-pyrimidinediamine;
N4-(3,4-dihydro-3-oxo-2H-pyrido[3,2-b][1,4]oxazin-6-yl)-5-fluoro-N2-[4-homomorpholinophenyl]-2,4-pyrimidinediamine;
N4-(2,2-dimethyl-3,4-dihydro-3-oxo-2H-pyrido[3,2-b][1,4]oxazin-6-yl)-5-fluoro-N2-[3-(2-propoxy)-4-morpholinophenyl]-2,4-pyrimidinediamine;
N4-(3,4-dihydro-3-oxo-2H-pyrido[3,2-b][1,4]oxazin-6-yl)-5-fluoro-N2-[4-tetrahydropyranophenyl]-2,4-pyrimidinediamine;
N4-(2,2-dimethyl-3,4-dihydro-3-oxo-2H-pyrido[3,2-b][1,4]oxazin-6-yl)-5-fluoro-N2-[4-tetrahydropyranophenyl]-2,4-pyrimidinediamine;
N4-(2,2-dimethyl-3,4-dihydro-3-oxo-2H-pyrido[3,2-b][1,4]oxazin-6-yl)-5-fluoro-N2-[-3-methoxy-4-tetrahydropyranophenyl]-2,4-pyrimidinediamine;
N4-(3,4-dihydro-3-oxo-2H-pyrido[3,2-b][1,4]oxazin-6-yl)-5-fluoro-N2-[-3-methoxy-4-tetrahydropyranophenyl]-2,4-pyrimidinediamine;

N4-(2,2-dimethyl-3,4-dihydro-3-oxo-2H-pyrido[3,2-b]
[1,4]oxazin-6-yl)-5-fluoro-N2-[4-(4-hydroxypiperidin-
1-yl)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(piperidin-1-yl)phe-
nyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-((2S)-2-methylmor-
pholino)phenyl]-2,4-pyrimidinediamine;
N4-(3,4-dihydro-3-oxo-2H-pyrido[3,2-b][1,4]oxazin-6-
yl)-5-fluoro-N2-[6-((2S)-2-methylmorpholino)phe-
nyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-((3R)-2-methylmor-
pholino)phenyl]-2,4-pyrimidinediamine;
N4-(3,4-dihydro-3-oxo-2H-pyrido[3,2-b][1,4]oxazin-6-
yl)-5-fluoro-N2-[6-((3R)-2-methylmorpholino)phe-
nyl]-2,4-pyrimidinediamine;
N4-(3,4-dihydro-3-oxo-2H-pyrido[3,2-b][1,4]oxazin-6-
yl)-5-fluoro-N2-[4-(piperidin-1-yl)phenyl]-2,4-pyrim-
idinediamine;
N4-(3,4-dihydro-3-oxo-2H-pyrido[3,2-b][1,4]oxazin-6-
yl)-5-fluoro-N2-[1,2,4a,5-tetrahydro-4H-[1,4]oxazino
[3,4-c][1,4]benzoxazin-8-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(4-ethoxypiperidin-
1-yl)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(4-isopropoxypiperi-
din-1-yl)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(4-morpholinopip-
eridin-1-yl)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(4-(diethylamino)pi-
peridin-1-yl)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[3-fluoro-4-(3-(hy-
droxymethyl)morpholino)phenyl]-2,4-pyrimidinedi-
amine;
N4-(2,2-dimethyl-3,4-dihydro-3-oxo-2H-pyrido[3,2-b]
[1,4]oxazin-6-yl)-5-fluoro-N2-[4-(4-aminopiperidin-1-
yl)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(2-oxooxazolidin-3-
yl)phenyl]-2,4-pyrimidinediamine;
N4-(3,4-dihydro-3-oxo-2H-pyrido[3,2-b][1,4]oxazin-6-
yl)-N2-[4-(2,2-dimethylmorpholino)phenyl]-5-fluoro-
2,4-pyrimidinediamine;
N4-(2,2-dimethyl-3,4-dihydro-3-oxo-2H-pyrido[3,2-b]
[1,4]oxazin-6-yl)-N2-[4-(2,2-dimethylmorpholino)
phenyl]-5-fluoro-2,4-pyrimidinediamine;
N4-(3,4-dihydro-3-oxo-2H-pyrido[3,2-b][1,4]oxazin-6-
yl)-5-fluoro-N2-[4-((2R)-2-methylmorpholino)phe-
nyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-((2R)-2-methylmor-
pholino)phenyl]-2,4-pyrimidinediamine;
N4-(3,4-dihydro-3-oxo-2H-pyrido[3,2-b][1,4]oxazin-6-
yl)-5-fluoro-N2-[4-((3S)-3-methylmorpholino)phe-
nyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-((3S)-3-methylmor-
pholino)phenyl]-2,4-pyrimidinediamine;
rac-N4-(3,4-dihydro-3-oxo-2H-pyrido[3,2-b][1,4]oxazin-
6-yl)-N2-[4-((2-dimethylaminomethyl)morpholino)
phenyl]-5-fluoro-2,4-pyrimidinediamine;
N4-(2,2-dimethyl-3,4-dihydro-3-oxo-2H-pyrido[3,2-b]
[1,4]oxazin-6-yl)-N2-[4-((3S)-3-methylmorpholino)
phenyl]-5-fluoro-2,4-pyrimidinediamine;
5-Fluoro-N2-(4-morpholinophenyl)-N4-(3'-oxo-3',4'-di-
hydrospiro[cyclobutane-1,2'-pyrido[3,2-b][1,4]ox-
azine]-6-yl)-2,4-pyrimidinediamine;
N2-[4-(2,2-Dimethylmorpholino)phenyl]-5-fluoro-N4-
(3'-oxo-3',4'-dihydrospiro[cyclobutane-1,2'-pyrido[3,2-
b][1,4]oxazine]-6-yl)-2,4-pyrimidinediamine;
N4-(3,4-dihydro-3-oxo-2H-pyrido[3,2-b][1,4]oxazin-6-
yl)-5-fluoro-N2-[4-((2-hydroxyethyl)morpholino)phe-
nyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-((2-hydroxyethyl)
morpholino)phenyl]-2,4-pyrimidinediamine;
N4-(3,4-dihydro-3-oxo-2H-pyrido[3,2-b][1,4]oxazin-6-
yl)-5-fluoro-N2-[4-((2-hydroxymethyl)morpholino)
phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-((2-hydroxymethyl)
morpholino)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[2-(pyridin-4-yl)-1H-
benzo[d]imidazol-6-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-(isoquinolin-7-yl)-2,4-
pyrimidinediamine;
N4-(2,2-dimethyl-3,4-dihydro-3-oxo-2H-pyrido[3,2-b]
[1,4]oxazin-6-yl)-5-fluoro-N2-(6-(tetrahydro-2H-py-
ran-4-ylamino)pyridin-3-yl))-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(4-hydroxycyclo-
hexyl)aminopyrid-3-yl]-2,4-pyrimidinediamine;
(R)—N4-(2,2-dimethyl-3,4-dihydro-3-oxo-2H-pyrido[3,
2-b][1,4]oxazin-6-yl)-5-fluoro-N2-[6-(3-fluoropyrroli-
din-1-yl)pyrid-3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(2,2,3,3,5,5,6,6-d$_8$-
morpholino)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(2,2,3,3,5,5,6,6-d$_8$-
morpholino)phenyl]-2,4-pyrimidinediamine;
N4-(3,4-dihydro-3-oxo-4-propyl-2H-pyrido[3,2-b][1,4]
oxazin-6-yl)-5-fluoro-N2-[4-morpholino-3-(trifluo-
romethyl)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(1,1-dioxidothiomor-
pholin-4-yl)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(4-(aminocarbonyl)
piperidin-1-yl)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(3-oxopiperazin-1-
yl)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(4-methoxypiperi-
din-1-yl)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-thiomorpholinophe-
nyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(4-cyanopiperidin-1-
yl)phenyl]-2,4-pyrimidinediamine;
N4-(2,2-dimethyl-3,4-dihydro-3-oxo-2H-pyrido[3,2-b]
[1,4]oxazin-6-yl)-5-fluoro-N2-[4-(4-(methoxymethyl)
piperidin-1-yl)phenyl]-2,4-pyrimidinediamine;

N4-(2,2-dimethyl-3,4-dihydro-3-oxo-2H-pyrido[3,2-b][1,4]oxazin-6-yl)-5-fluoro-N2-[4-(1-oxa-8-azaspiro[4.5]decan-8-yl)phenyl]-2,4-pyrimidinediamine;

N4-(2,2-dimethyl-3,4-dihydro-3-oxo-2H-pyrido[3,2-b][1,4]oxazin-6-yl)-5-fluoro-N2-[4-(2-oxa-8-azaspiro[4.5]decan-8-yl)phenyl]-2,4-pyrimidinediamine;

N4-(2,2-dimethyl-3,4-dihydro-3-oxo-2H-pyrido[3,2-b][1,4]oxazin-6-yl)-5-fluoro-N2-[4-(2-oxa-7-azaspiro[3.5]nonan-7-yl)phenyl]-2,4-pyrimidinediamine;

N4-(2,2-dimethyl-3,4-dihydro-3-oxo-2H-pyrido[3,2-b][1,4]oxazin-6-yl)-5-fluoro-N2-[3-methyl-4-(2-oxa-8-azaspiro[4.5]decan-8-yl)phenyl]-2,4-pyrimidinediamine;

or a pharmaceutically acceptable salt thereof.

14. The compound according to claim 1, which is:

N4-(2,2-dimethyl-3,4-dihydro-3-oxo-2H-pyrido[3,2-b][1,4]oxazin-6-yl)-5-fluoro-N2-[6-morpholinopyridin-3-yl]-2,4-pyrimidinediamine;

N4-(3,4-dihydro-3-oxo-2H-pyrido[3,2-b][1,4]oxazin-6-yl)-5-fluoro-N2-[6-morpholinopyridin-3-yl]-2,4-pyrimidinediamine;

N4-(3,4-dihydro-3-oxo-2H-pyrido[3,2-b][1,4]oxazin-6-yl)-5-fluoro-N2-[6-((2R)-2-methylmorpholino)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-((2S)-2-methylmorpholino)pyridin-3-yl]-2,4-pyrimidinediamine;

N4-(2,2-Dimethyl-3-oxo-2H-pyrido[3,2-b][1,4]oxazin-6-yl)-5-fluoro-N2-[6-(2,2-dimethylmorpholino)pyridin-3-yl]-2,4-pyrimidinediamine;

N4-(3,4-dihydro-3-oxo-2H-pyrido[3,2-b][1,4]oxazin-6-yl)-5-fluoro-N2-[6-(2,2-dimethylmorpholino)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[5-fluoro-6-morpholinopyridin-3-yl]-2,4-pyrimidinediamine;

N4-(3,4-dihydro-3-oxo-2H-pyrido[3,2-b][1,4]oxazin-6-yl)-5-fluoro-N2-[5-methyl-6-morpholinopyridin-3-yl]-2,4-pyrimidinediamine;

N4-(3,4-dihydro-3-oxo-2H-pyrido[3,2-b][1,4]oxazin-6-yl)-5-fluoro-N2-[5-methyl-6-(2,2-dimethylmorpholino)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[5-methyl-6-morpholinopyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[5-methyl-6-(2,2-dimethylmorpholino)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[5-fluoro-6-(2,2-dimethylmorpholino)pyridin-3-yl]-2,4-pyrimidinediamine;

N4-(3,4-dihydro-3-oxo-2H-pyrido[3,2-b][1,4]oxazin-6-yl)-5-fluoro-N2-[5-fluoro-6-morpholinopyridin-3-yl]-2,4-pyrimidinediamine;

N4-(3,4-dihydro-3-oxo-2H-pyrido[3,2-b][1,4]oxazin-6-yl)-5-fluoro-N2-[5-fluoro-6-(2,2-dimethylmorpholino)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-(4-methylpiperazin-1-yl)pyridin-3-yl]-2,4-pyrimidinediamine;

N4-(3,4-dihydro-3-oxo-2H-pyrido[3,2-b][1,4]oxazin-6-yl)-5-fluoro-N2-[6-(4-methylpiperazin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-(homomorpholino)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[5-methoxy-6-morpholinopyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-tetrahydropyranopyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-((3R)-3-methylmorpholino)pyridin-3-yl]-2,4-pyrimidinediamine;

N4-(3,4-dihydro-3-oxo-2H-pyrido[3,2-b][1,4]oxazin-6-yl)-5-fluoro-N2-[6-((3R)-3-methylmorpholino)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-(4-hydroxypiperidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-(4-methoxypiperidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-(4-ethoxypiperidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-((3R)-3-hydroxypyrrolidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-((3R)-3-methoxypyrrolidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-((3R)-3-ethoxypyrrolidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-(3-methylenemorpholino)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-(3-(ethoxymethyl)morpholino)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-(4-morpholinopiperidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-(4-(diethylamino)piperidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-(1,4-diazabicyclo[3.2.2]nonan-4-yl)pyridin-3-yl]-2,4-pyrimidinediamine;

N4-(3,4-dihydro-3-oxo-2H-pyrido[3,2-b][1,4]oxazin-6-yl)-5-fluoro-N2-[6-((3S)-3-hydroxypyrrolidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-((3R)-3-hydroxypyrrolidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-((3R)-3-methoxypyrrolidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-(3-(diethylamino)pyrrolidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-(3-morpholinopyrrolidin-1-yl)pyridin-3-yl]-2,4-pyrimidinediamine;

N4-(2,2-dimethyl-3,4-dihydro-3-oxo-2H-pyrido[3,2-b][1,4]oxazin-6-yl)-5-fluoro-N2-[6-((3R)-3-(ethylamino)pyrrolidin-1-yl)pyridin-3-yl]-2,4-pyrimidinediamine;

N4-(2,2-dimethyl-3,4-dihydro-3-oxo-2H-pyrido[3,2-b]
[1,4]oxazin-6-yl)-5-fluoro-N2-[6-(3-methoxyazetidin-
1-yl)pyridin-3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-(3-(aminocarbonyl)
pyrrolidin-1-yl)pyridin-3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-((3S)-3-(hydroxym-
ethyl)pyrrolidin-1-yl)pyridin-3-yl]-2,4-pyrimidinedi-
amine;
N4-(2,2-dimethyl-3,4-dihydro-3-oxo-2H-pyrido[3,2-b]
[1,4]oxazin-6-yl)-5-fluoro-N2-[6-(2-oxooxazolidin-3-
yl)pyridin-3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-((4R)-4-isopropyl-2-
oxooxazolidin-3-yl)pyridin-3-yl]-2,4-pyrimidinedi-
amine;
N4-(2,2-dimethyl-3,4-dihydro-3-oxo-2H-pyrido[3,2-b]
[1,4]oxazin-6-yl)-5-fluoro-N2-[6-((4S)-4-isopropyl-2-
oxooxazolidin-3-yl)pyridin-3-yl]-2,4-pyrimidinedi-
amine;
N4-(2,2-dimethyl-3,4-dihydro-3-oxo-2H-pyrido[3,2-b]
[1,4]oxazin-6-yl)-5-fluoro-N2-[2,3'-bipyridin-5-yl]-2,
4-pyrimidinediamine;
N4-(2,2-dimethyl-3,4-dihydro-3-oxo-2H-pyrido[3,2-b]
[1,4]oxazin-6-yl)-5-fluoro-N2-[6-methylpyridin-3-yl]-
2,4-pyrimidinediamine;
N4-(2,2-dimethyl-3,4-dihydro-3-oxo-2H-pyrido[3,2-b]
[1,4]oxazin-6-yl)-5-fluoro-N2-[6-((1S,4S)-5-oxa-2-
aza-bicyclo[2.2.1]heptan-2-yl)pyridin-3-yl]-2,4-pyrim-
idinediamine;
N4-(3,4-dihydro-3-oxo-2H-pyrido[3,2-b][1,4]oxazin-6-
yl)-5-fluoro-N2-[6-((2S)-2-methylmorpholino)pyridin-
3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-((2S)-2-methylmor-
pholino)pyridin-3-yl]-2,4-pyrimidinediamine;
rac-Cis-N4-(3,4-dihydro-3-oxo-2H-pyrido[3,2-b][1,4]ox-
azin-6-yl)-N2-[6-(2,6-dimethylmorpholino)pyridin-3-
yl]-5-fluoro-2,4-pyrimidinediamine;
rac-Cis-N4-(2,2-dimethyl-3,4-dihydro-3-oxo-2H-pyrido
[3,2-b][1,4]oxazin-6-yl)-N2-[6-(2,6-dimethylmor-
pholino)pyridin-3-yl]-5-fluoro-2,4-pyrimidinediamine;
N4-(3,4-dihydro-3-oxo-2H-pyrido[3,2-b][1,4]oxazin-6-
yl)-5-fluoro-N2-[6-(2-methoxyethyl)methylamino)py-
ridin-3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-(2-methoxyethyl)
methylamino)pyridin-3-yl]-2,4-pyrimidinediamine;
N4-(3,4-dihydro-3-oxo-2H-pyrido[3,2-b][1,4]oxazin-6-
yl)-N2-[6-(((2S)-2-ethoxymethyl)morpholino)pyridin-
3-yl]-5-fluoro-2,4-pyrimidinediamine;
N4-(2,2-dimethyl-3,4-dihydro-3-oxo-2H-pyrido[3,2-b]
[1,4]oxazin-6-yl)-N2-[6-(((2S)-2-ethoxymethyl)mor-
pholino)pyridin-3-yl]-5-fluoro-2,4-pyrimidinediamine;
N4-(3,4-dihydro-3-oxo-2H-pyrido[3,2-b][1,4]oxazin-6-
yl)-N2-[6-(((2R)-2-ethoxymethyl)morpholino)pyridin-
3-yl]-5-fluoro-2,4-pyrimidinediamine;
N4-(2,2-dimethyl-3,4-dihydro-3-oxo-2H-pyrido[3,2-b]
[1,4]oxazin-6-yl)-N2-[6-(((2R)-2-ethoxymethyl)mor-
pholino)pyridin-3-yl]-5-fluoro-2,4-pyrimidinediamine;
rac-N4-(3,4-dihydro-3-oxo-2H-pyrido[3,2-b][1,4]oxazin-
6-yl)-N2-[6-(2,5-dimethylmorpholino)pyridin-3-yl]-5-
fluoro-2,4-pyrimidinediamine;
rac-N4-(2,2-dimethyl-3,4-dihydro-3-oxo-2H-pyrido[3,2-
b][1,4]oxazin-6-yl)-5-N2-[6-(2,5-dimethylmor-
pholino)pyridin-3-yl]-5-fluoro-2,4-pyrimidinediamine;
N4-(3,4-dihydro-3-oxo-2H-pyrido[3,2-b][1,4]oxazin-6-
yl)-5-fluoro-N2-[6-(2,2,3,3,5,5,6,6-$d_8$-morpholino)py-
ridin-3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-(2,2,3,3,5,5,6,6-$d_8$-
morpholino)pyridin-3-yl]-2,4-pyrimidinediamine;
N4-(3,4-dihydro-3-oxo-2H-pyrido[3,2-b][1,4]oxazin-6-
yl)-5-fluoro-N2-[6-(((S)-methyl(tetrahydrofuran-2-yl)
methyl)amino)pyridin-3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-(((S)-methyl(tetrahy-
drofuran-2-yl)methyl)amino)pyridin-3-yl]-2,4-pyrim-
idinediamine;
N4-(3,4-dihydro-3-oxo-2H-pyrido[3,2-b][1,4]oxazin-6-
yl)-5-fluoro-N2-[6-(((R)-methyl(tetrahydrofuran-2-yl)
methyl)amino)pyridin-3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-(((R)-methyl(tet-
rahydrofuran-2-yl)methyl)amino)pyridin-3-yl]-2,4-py-
rimidinediamine;
N4-(2,2-dimethyl-3,4-dihydro-3-oxo-2H-pyrido[3,2-b]
[1,4]oxazin-6-yl)-5-fluoro-N2-[6-((3S)-3-methylmor-
pholino)pyridin-3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-((3S)-3-methylmor-
pholino)pyridin-3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-(methyl(tetrahydro-
2H-pyran-4-yl)amino)pyridin-3-yl]-2,4-pyrimidinedi-
amine;
N4-(2,2-dimethyl-3,4-dihydro-3-oxo-2H-pyrido[3,2-b]
[1,4]oxazin-6-yl)-5-fluoro-N2-[6-(2-oxa-8-azaspiro
[4.5]decan-8-yl)pyridin-3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-((2R)-2-(fluorom-
ethyl)morpholino)pyridin-3-yl]-2,4-pyrimidinedi-
amine;
N4-(2,2-dimethyl-3,4-dihydro-3-oxo-2H-pyrido[3,2-b]
[1,4]oxazin-6-yl)-5-fluoro-N2-[6-(3-hydroxyazetidin-
1-yl)pyridin-3-yl]-2,4-pyrimidinediamine;
N4-(2,2-dimethyl-3,4-dihydro-3-oxo-2H-pyrido[3,2-b]
[1,4]oxazin-6-yl)-5-fluoro-N2-[6-(dimethylamino)py-
ridin-3-yl]-2,4-pyrimidinediamine;
or a pharmaceutically acceptable salt thereof.

15. A pharmaceutically acceptable salt of a compound according to claim 1.

16. A pharmaceutical composition comprising a compound or salt according to claim 1 and an acceptable carrier, excipient and/or diluent.

17. A method of inhibiting cell degranulation in a subject, comprising administering to the subject a pharmaceutically effective amount of a compound or salt according to claim 1 effective to inhibit degranulation.

18. A method of inhibiting an activity of a Syk kinase in a subject, comprising administering to the subject a pharmaceutically effective amount of a compound or salt according to claim 1 effective to inhibit the Syk kinase activity.

19. A method of inhibiting an Fc receptor signal transduction cascade in a subject, comprising administering to the subject a pharmaceutically effective amount of a compound or salt according to claim 1 effective to inhibit the Fc receptor signal transduction cascade.

20. The method according to claim 19 in which the Fc receptor is selected from FcαRI, FcγRI, FcγRIII and FcεRI.

21. A method of inhibiting Syk kinase in a cell comprising contacting a Syk kinase or a cell comprising a Syk kinase with a compound or salt according to claim 1.

22. A method of inhibiting degranulation of a cell comprising contacting a cell that degranulates with a compound or salt according to claim 1.

23. A method of inhibiting the Fc receptor signaling cascade comprising contacting a cell expressing an Fc receptor with a compound or salt according to claim 1.

24. A method of inhibiting the Syk-dependent signal transduction cascade comprising contacting a Syk-dependent receptor or a cell expressing a Syk-dependent receptor with a compound or salt according to claim 1.

* * * * *